(12) United States Patent
Estes

(10) Patent No.: US 12,064,591 B2
(45) Date of Patent: *Aug. 20, 2024

(54) INFUSION PUMP SYSTEM AND METHOD

(71) Applicant: Insulet Corporation, Acton, MA (US)

(72) Inventor: Mark C. Estes, Malibu, CA (US)

(73) Assignee: Insulet Corporation, Acton, MA (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/445,819

(22) Filed: Aug. 24, 2021

(65) Prior Publication Data

US 2021/0379280 A1 Dec. 9, 2021

Related U.S. Application Data

(60) Continuation of application No. 15/893,145, filed on Feb. 9, 2018, now Pat. No. 11,147,914, which is a
(Continued)

(51) Int. Cl.
*A61M 5/142* (2006.01)
*A61M 5/145* (2006.01)
(Continued)

(52) U.S. Cl.
CPC .... *A61M 5/14244* (2013.01); *A61M 5/14546* (2013.01); *A61M 5/14566* (2013.01); *A61M 5/158* (2013.01); *G16H 10/60* (2018.01); *G16H 20/17* (2018.01); *G16H 40/63* (2018.01); *G16H 40/67* (2018.01); *G16Z 99/00* (2019.02); *A61M 2005/14208* (2013.01); *A61M 2005/14268* (2013.01); *A61M 5/1456* (2013.01); *A61M 2005/1586* (2013.01);
(Continued)

(58) Field of Classification Search
CPC .......... A61M 5/14244; A61M 5/14546; A61M 5/14566; A61M 2005/14208; A61M 2005/14268; A61M 2205/3515; A61M 2205/3569; A61M 2205/3576; A61M 5/1456
See application file for complete search history.

(56) References Cited

U.S. PATENT DOCUMENTS

| 303,013 | A | 8/1884 | Horton |
| 445,545 | A | 2/1891 | Crane |

(Continued)

FOREIGN PATENT DOCUMENTS

| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)
(Continued)

*Primary Examiner* — William R Carpenter
*Assistant Examiner* — William R Frehe
(74) *Attorney, Agent, or Firm* — TraskBritt

(57) ABSTRACT

Some embodiments of an infusion pump system may be configured to wirelessly communicate with other devices using near field communication (NFC). In particular embodiments, by incorporating near field communication capabilities into the infusion pump system, user communications with the infusion pump system can be enhanced and simplified.

10 Claims, 6 Drawing Sheets

Related U.S. Application Data division of application No. 15/383,176, filed on Dec. 19, 2016, now Pat. No. 10,207,047, which is a continuation of application No. 13/946,330, filed on Jul. 19, 2013, now Pat. No. 9,561,324.

(51) Int. Cl.
| | | |
|---|---|---|
| *A61M 5/158* | (2006.01) | |
| *G16H 10/60* | (2018.01) | |
| *G16H 20/17* | (2018.01) | |
| *G16H 40/63* | (2018.01) | |
| *G16H 40/67* | (2018.01) | |
| *G16Z 99/00* | (2019.01) | |

(52) U.S. Cl.
CPC .............. *A61M 2205/3515* (2013.01); *A61M 2205/3569* (2013.01); *A61M 2205/3576* (2013.01); *G05B 2219/31197* (2013.01)

(56) References Cited

U.S. PATENT DOCUMENTS

| | | |
|---|---|---|
| 588,583 A | 8/1897 | Lade |
| 1,441,508 A | 1/1923 | Marius et al. |
| 2,283,925 A | 5/1942 | Harvey |
| 2,605,765 A | 8/1952 | Kollsman |
| 2,797,149 A | 6/1957 | Skeggs |
| 2,886,529 A | 5/1959 | Guillaud |
| 3,413,573 A | 11/1968 | Nathanson et al. |
| 3,574,114 A | 4/1971 | Monforte |
| 3,614,554 A | 10/1971 | Shield et al. |
| 3,631,847 A | 1/1972 | Hobbs |
| 3,634,039 A | 1/1972 | Brondy |
| 3,688,764 A | 9/1972 | Reed |
| 3,812,843 A | 5/1974 | Wootten et al. |
| 3,841,328 A | 10/1974 | Jensen |
| 3,885,662 A | 5/1975 | Schaefer |
| 3,886,938 A | 6/1975 | Szabo et al. |
| 3,963,380 A | 6/1976 | Thomas et al. |
| 3,983,077 A | 9/1976 | Fuller et al. |
| 4,055,175 A | 10/1977 | Clemens et al. |
| 4,077,405 A | 3/1978 | Haerten et al. |
| 4,108,177 A | 8/1978 | Pistor |
| 4,146,029 A | 3/1979 | Ellinwood, Jr. |
| 4,151,845 A | 5/1979 | Clemens |
| 4,231,368 A | 11/1980 | Becker |
| 4,235,234 A | 11/1980 | Martin et al. |
| 4,245,634 A | 1/1981 | Albisser et al. |
| 4,265,241 A | 5/1981 | Portner et al. |
| 4,268,150 A | 5/1981 | Chen |
| 4,295,176 A | 10/1981 | Wittwer |
| 4,300,554 A | 11/1981 | Hessberg et al. |
| 4,313,439 A | 2/1982 | Babb et al. |
| 4,368,980 A | 1/1983 | Aldred et al. |
| 4,373,527 A | 2/1983 | Fischell |
| 4,398,908 A | 8/1983 | Siposs |
| 4,400,683 A | 8/1983 | Eda et al. |
| 4,403,984 A | 9/1983 | Ash et al. |
| 4,424,720 A | 1/1984 | Bucchianeri |
| 4,435,173 A | 3/1984 | Siposs et al. |
| 4,443,218 A | 4/1984 | DeCant et al. |
| 4,464,170 A | 8/1984 | Clemens et al. |
| 4,469,481 A | 9/1984 | Kobayashi |
| 4,475,901 A | 10/1984 | Kraegen et al. |
| 4,493,704 A | 1/1985 | Beard et al. |
| 4,498,843 A | 2/1985 | Schneider et al. |
| 4,507,115 A | 3/1985 | Kambara et al. |
| 4,523,170 A | 6/1985 | Huth, III |
| 4,526,568 A | 7/1985 | Clemens et al. |
| 4,526,569 A | 7/1985 | Bernardi |
| 4,529,401 A | 7/1985 | Leslie et al. |
| 4,551,134 A | 11/1985 | Slavik et al. |
| 4,552,561 A | 11/1985 | Eckenhoff et al. |
| 4,559,033 A | 12/1985 | Stephen et al. |
| 4,559,037 A | 12/1985 | Franetzki et al. |
| 4,562,751 A | 1/1986 | Nason et al. |
| 4,564,054 A | 1/1986 | Gustavsson |
| 4,573,968 A | 3/1986 | Parker |
| 4,585,439 A | 4/1986 | Michel |
| 4,601,707 A | 7/1986 | Albisser et al. |
| 4,624,661 A | 11/1986 | Arimond |
| 4,633,878 A | 1/1987 | Bombardieri |
| 4,634,427 A | 1/1987 | Hannula et al. |
| 4,646,038 A | 2/1987 | Wanat |
| 4,652,260 A | 3/1987 | Fenton et al. |
| 4,657,529 A | 4/1987 | Prince et al. |
| 4,668,220 A | 5/1987 | Hawrylenko |
| 4,678,408 A | 7/1987 | Nason et al. |
| 4,681,569 A | 7/1987 | Coble et al. |
| 4,684,368 A | 8/1987 | Kenyon |
| 4,685,903 A | 8/1987 | Cable et al. |
| 4,731,726 A | 3/1988 | Allen, III |
| 4,734,092 A | 3/1988 | Millerd |
| 4,743,243 A | 5/1988 | Vaillancourt |
| 4,749,109 A | 6/1988 | Kamen |
| 4,755,169 A | 7/1988 | Sarnoff et al. |
| 4,755,173 A | 7/1988 | Konopka et al. |
| 4,759,120 A | 7/1988 | Bernstein |
| 4,768,506 A | 9/1988 | Parker et al. |
| 4,781,688 A | 11/1988 | Thoma et al. |
| 4,781,693 A | 11/1988 | Martinez et al. |
| 4,808,161 A | 2/1989 | Kamen |
| 4,838,857 A | 6/1989 | Strowe et al. |
| 4,850,817 A | 7/1989 | Nason et al. |
| 4,854,170 A | 8/1989 | Brimhall et al. |
| 4,859,492 A | 8/1989 | Rogers et al. |
| 4,880,770 A | 11/1989 | Mir et al. |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,900,292 A | 2/1990 | Berry et al. |
| 4,902,278 A | 2/1990 | Maget et al. |
| 4,919,596 A | 4/1990 | Slate et al. |
| 4,925,444 A | 5/1990 | Orkin et al. |
| 4,940,527 A | 7/1990 | Kazlauskas et al. |
| 4,944,659 A | 7/1990 | Labbe et al. |
| 4,967,201 A | 10/1990 | Rich, III |
| 4,969,874 A | 11/1990 | Michel et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,007,458 A | 4/1991 | Marcus et al. |
| 5,029,591 A | 7/1991 | Teves |
| 5,045,064 A | 9/1991 | Idriss |
| 5,061,424 A | 10/1991 | Karimi et al. |
| 5,062,841 A | 11/1991 | Siegel |
| 5,084,749 A | 1/1992 | Losee et al. |
| 5,088,981 A | 2/1992 | Howson et al. |
| 5,088,990 A | 2/1992 | Hivale et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,130,675 A | 7/1992 | Sugawara |
| 5,134,079 A | 7/1992 | Cusack et al. |
| 5,139,999 A | 8/1992 | Gordon et al. |
| 5,153,827 A | 10/1992 | Coutre et al. |
| 5,154,973 A | 10/1992 | Imagawa et al. |
| 5,165,406 A | 11/1992 | Wong |
| 5,176,632 A | 1/1993 | Bernardi |
| 5,176,662 A | 1/1993 | Bartholomew et al. |
| 5,178,609 A | 1/1993 | Ishikawa |
| 5,189,609 A | 2/1993 | Tivig et al. |
| 5,190,522 A | 3/1993 | Wojcicki et al. |
| 5,198,824 A | 3/1993 | Poradish |
| 5,205,819 A | 4/1993 | Ross et al. |
| 5,207,642 A | 5/1993 | Orkin et al. |
| 5,209,230 A | 5/1993 | Swedlow et al. |
| 5,213,483 A | 5/1993 | Flaherty et al. |
| 5,217,754 A | 6/1993 | Santiago-Aviles et al. |
| 5,219,377 A | 6/1993 | Poradish |
| 5,225,763 A | 7/1993 | Krohn et al. |

(56) References Cited

U.S. PATENT DOCUMENTS

| | | | |
|---|---|---|---|
| 5,232,439 | A | 8/1993 | Campbell et al. |
| 5,237,993 | A | 8/1993 | Skrabal |
| 5,244,463 | A | 9/1993 | Cordner et al. |
| 5,250,027 | A | 10/1993 | Lewis et al. |
| 5,254,096 | A | 10/1993 | Rondelet et al. |
| 5,257,980 | A | 11/1993 | Van et al. |
| 5,261,882 | A | 11/1993 | Sealfon |
| 5,263,198 | A | 11/1993 | Geddes et al. |
| 5,272,485 | A | 12/1993 | Mason et al. |
| 5,273,517 | A | 12/1993 | Barone et al. |
| 5,281,202 | A | 1/1994 | Weber et al. |
| 5,281,808 | A | 1/1994 | Kunkel |
| 5,299,571 | A | 4/1994 | Mastrototaro |
| 5,308,982 | A | 5/1994 | Ivaldi et al. |
| 5,314,412 | A | 5/1994 | Rex |
| 5,335,994 | A | 8/1994 | Weynant |
| 5,338,157 | A | 8/1994 | Blomquist |
| 5,342,180 | A | 8/1994 | Daoud |
| 5,342,298 | A | 8/1994 | Michaels et al. |
| 5,346,476 | A | 9/1994 | Elson |
| 5,349,575 | A | 9/1994 | Park |
| 5,364,342 | A | 11/1994 | Beuchat et al. |
| 5,377,674 | A | 1/1995 | Kuestner |
| 5,380,665 | A | 1/1995 | Cusack et al. |
| 5,385,539 | A | 1/1995 | Maynard |
| 5,389,078 | A | 2/1995 | Zalesky et al. |
| 5,395,340 | A | 3/1995 | Lee |
| 5,403,797 | A | 4/1995 | Ohtani et al. |
| 5,411,487 | A | 5/1995 | Castagna |
| 5,411,889 | A | 5/1995 | Hoots et al. |
| 5,421,812 | A | 6/1995 | Langley et al. |
| 5,427,988 | A | 6/1995 | Sengupta et al. |
| 5,433,710 | A | 7/1995 | Vanantwerp et al. |
| 5,456,945 | A | 10/1995 | McMillan et al. |
| 5,468,727 | A | 11/1995 | Phillips et al. |
| 5,478,610 | A | 12/1995 | Desu et al. |
| 5,505,709 | A | 4/1996 | Funderburk et al. |
| 5,505,828 | A | 4/1996 | Wong et al. |
| 5,507,288 | A | 4/1996 | Boecker et al. |
| 5,513,382 | A | 4/1996 | Agahi-Kesheh et al. |
| 5,527,288 | A | 6/1996 | Gross et al. |
| 5,533,389 | A | 7/1996 | Kamen et al. |
| 5,535,445 | A | 7/1996 | Gunton |
| 5,540,772 | A | 7/1996 | McMillan et al. |
| 5,543,773 | A | 8/1996 | Evans et al. |
| 5,545,143 | A | 8/1996 | Fischell et al. |
| 5,551,850 | A | 9/1996 | Williamson et al. |
| 5,554,123 | A | 9/1996 | Herskowitz |
| 5,558,640 | A | 9/1996 | Pfeiler et al. |
| 5,569,186 | A | 10/1996 | Lord et al. |
| 5,582,593 | A | 12/1996 | Hultman |
| 5,584,053 | A | 12/1996 | Kommrusch et al. |
| 5,584,813 | A | 12/1996 | Livingston et al. |
| 5,590,387 | A | 12/1996 | Schmidt et al. |
| 5,609,572 | A | 3/1997 | Lang |
| 5,614,252 | A | 3/1997 | McMillan et al. |
| 5,625,365 | A | 4/1997 | Tom et al. |
| 5,626,566 | A | 5/1997 | Petersen et al. |
| 5,635,433 | A | 6/1997 | Sengupta |
| 5,637,095 | A | 6/1997 | Nason et al. |
| 5,656,032 | A | 8/1997 | Kriesel et al. |
| 5,665,065 | A | 9/1997 | Colman et al. |
| 5,665,070 | A | 9/1997 | McPhee |
| 5,672,167 | A | 9/1997 | Athayde et al. |
| 5,678,539 | A | 10/1997 | Schubert et al. |
| 5,685,844 | A | 11/1997 | Marttila |
| 5,685,859 | A | 11/1997 | Kornerup |
| 5,693,018 | A | 12/1997 | Kriesel et al. |
| 5,697,899 | A | 12/1997 | Hillman et al. |
| 5,700,695 | A | 12/1997 | Yassinzadeh et al. |
| 5,703,364 | A | 12/1997 | Rosenthal |
| 5,707,459 | A | 1/1998 | Itoyama et al. |
| 5,707,715 | A | 1/1998 | Derochemont et al. |
| 5,713,875 | A | 2/1998 | Tanner, II |
| 5,714,123 | A | 2/1998 | Sohrab |
| 5,716,343 | A | 2/1998 | Kriesel et al. |
| 5,718,562 | A | 2/1998 | Lawless et al. |
| 5,722,397 | A | 3/1998 | Eppstein |
| 5,741,216 | A | 4/1998 | Hemmingsen et al. |
| 5,741,228 | A | 4/1998 | Lambrecht et al. |
| 5,746,217 | A | 5/1998 | Erickson et al. |
| 5,747,350 | A | 5/1998 | Sattler |
| 5,747,870 | A | 5/1998 | Pedder |
| 5,748,827 | A | 5/1998 | Holl et al. |
| 5,755,682 | A | 5/1998 | Knudson et al. |
| 5,758,643 | A | 6/1998 | Wong et al. |
| 5,759,923 | A | 6/1998 | McMillan et al. |
| 5,764,189 | A | 6/1998 | Lohninger |
| 5,766,155 | A | 6/1998 | Hyman et al. |
| 5,771,567 | A | 6/1998 | Pierce et al. |
| 5,772,635 | A | 6/1998 | Dastur et al. |
| 5,776,103 | A | 7/1998 | Kriesel et al. |
| 5,779,676 | A | 7/1998 | Kriesel et al. |
| 5,785,688 | A | 7/1998 | Joshi et al. |
| 5,797,881 | A | 8/1998 | Gadot |
| 5,800,397 | A | 9/1998 | Wilson et al. |
| 5,800,405 | A | 9/1998 | McPhee |
| 5,800,420 | A | 9/1998 | Gross et al. |
| 5,801,057 | A | 9/1998 | Smart et al. |
| 5,804,048 | A | 9/1998 | Wong et al. |
| 5,807,075 | A | 9/1998 | Jacobsen et al. |
| 5,816,306 | A | 10/1998 | Giacomel |
| 5,817,007 | A | 10/1998 | Fodgaard et al. |
| 5,820,622 | A | 10/1998 | Gross et al. |
| 5,822,715 | A | 10/1998 | Worthington et al. |
| 5,823,951 | A | 10/1998 | Messerschmidt |
| 5,839,467 | A | 11/1998 | Saaski et al. |
| 5,840,020 | A | 11/1998 | Heinonen et al. |
| D403,313 | S | 12/1998 | Peppel |
| 5,848,991 | A | 12/1998 | Gross et al. |
| 5,851,197 | A | 12/1998 | Marano et al. |
| 5,852,803 | A | 12/1998 | Ashby et al. |
| 5,854,608 | A | 12/1998 | Leisten |
| 5,858,001 | A | 1/1999 | Tsals et al. |
| 5,858,005 | A | 1/1999 | Kriesel |
| 5,858,239 | A | 1/1999 | Kenley et al. |
| 5,859,621 | A | 1/1999 | Leisten |
| 5,865,806 | A | 2/1999 | Howell |
| 5,871,470 | A | 2/1999 | McWha |
| 5,873,731 | A | 2/1999 | Prendergast |
| 5,879,310 | A | 3/1999 | Sopp et al. |
| 5,889,459 | A | 3/1999 | Hattori et al. |
| 5,891,097 | A | 4/1999 | Saito et al. |
| 5,892,489 | A | 4/1999 | Kanba et al. |
| 5,893,838 | A | 4/1999 | Daoud et al. |
| 5,897,530 | A | 4/1999 | Jackson |
| 5,902,253 | A | 5/1999 | Pfeiffer et al. |
| 5,903,421 | A | 5/1999 | Furutani et al. |
| 5,906,597 | A | 5/1999 | McPhee |
| 5,911,716 | A | 6/1999 | Rake et al. |
| 5,914,941 | A | 6/1999 | Janky |
| 5,919,167 | A | 7/1999 | Mulhauser et al. |
| 5,925,018 | A | 7/1999 | Ungerstedt |
| 5,928,201 | A | 7/1999 | Poulsen et al. |
| 5,931,814 | A | 8/1999 | Alex et al. |
| 5,932,175 | A | 8/1999 | Knute et al. |
| 5,933,121 | A | 8/1999 | Rainhart et al. |
| 5,935,099 | A | 8/1999 | Peterson et al. |
| 5,945,963 | A | 8/1999 | Leisten |
| 5,947,911 | A | 9/1999 | Wong et al. |
| 5,947,934 | A | 9/1999 | Hansen et al. |
| 5,951,530 | A | 9/1999 | Steengaard et al. |
| 5,957,889 | A | 9/1999 | Poulsen et al. |
| 5,957,890 | A | 9/1999 | Mann et al. |
| 5,961,492 | A | 10/1999 | Kriesel et al. |
| 5,965,848 | A | 10/1999 | Altschul et al. |
| 5,971,941 | A | 10/1999 | Simons et al. |
| 5,984,894 | A | 11/1999 | Poulsen et al. |
| 5,984,897 | A | 11/1999 | Petersen et al. |
| 5,993,423 | A | 11/1999 | Choi |
| 5,997,475 | A | 12/1999 | Bortz |
| 5,997,501 | A | 12/1999 | Gross et al. |
| 6,003,736 | A | 12/1999 | Ljunggren |
| 6,005,151 | A | 12/1999 | Herrmann et al. |

(56) References Cited

U.S. PATENT DOCUMENTS

| | | | |
|---|---|---|---|
| 6,010,485 A | 1/2000 | Buch-Rasmussen et al. |
| 6,017,318 A | 1/2000 | Gauthier et al. |
| 6,019,747 A | 2/2000 | McPhee |
| 6,023,251 A | 2/2000 | Koo et al. |
| 6,024,539 A | 2/2000 | Blomquist |
| 6,027,826 A | 2/2000 | Derochemont et al. |
| 6,028,568 A | 2/2000 | Asakura et al. |
| 6,031,445 A | 2/2000 | Marty et al. |
| 6,032,059 A | 2/2000 | Henning et al. |
| 6,033,377 A | 3/2000 | Rasmussen et al. |
| 6,036,924 A | 3/2000 | Simons et al. |
| 6,040,578 A | 3/2000 | Malin et al. |
| 6,040,805 A | 3/2000 | Huynh et al. |
| 6,045,537 A | 4/2000 | Klitmose |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| 6,056,728 A | 5/2000 | Von Schuckmann |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,074,372 A | 6/2000 | Hansen |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,106,498 A | 8/2000 | Friedli et al. |
| 6,110,149 A | 8/2000 | Klitgaard et al. |
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,595 A | 10/2000 | Amano et al. |
| 6,126,637 A | 10/2000 | Kriesel et al. |
| 6,127,061 A | 10/2000 | Shun et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | De et al. |
| 6,154,176 A | 11/2000 | Fathy et al. |
| 6,156,014 A | 12/2000 | Petersen et al. |
| 6,157,041 A | 12/2000 | Thomas et al. |
| 6,161,028 A | 12/2000 | Braig et al. |
| 6,162,639 A | 12/2000 | Douglas |
| 6,171,276 B1 | 1/2001 | Lippe et al. |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |
| 6,226,082 B1 | 5/2001 | Roe |
| 6,231,540 B1 | 5/2001 | Smedegaard |
| 6,233,471 B1 | 5/2001 | Berner et al. |
| 6,244,776 B1 | 6/2001 | Wiley |
| 6,248,067 B1 | 6/2001 | Causey et al. |
| 6,248,090 B1 | 6/2001 | Jensen et al. |
| 6,248,093 B1 | 6/2001 | Moberg |
| 6,251,113 B1 | 6/2001 | Appelbaum et al. |
| 6,261,065 B1 | 7/2001 | Nayak et al. |
| 6,262,798 B1 | 7/2001 | Shepherd et al. |
| 6,266,020 B1 | 7/2001 | Chang |
| 6,269,340 B1 | 7/2001 | Ford et al. |
| 6,270,455 B1 | 8/2001 | Brown |
| 6,271,045 B1 | 8/2001 | Douglas et al. |
| 6,277,098 B1 | 8/2001 | Klitmose et al. |
| 6,280,381 B1 | 8/2001 | Malin et al. |
| 6,285,448 B1 | 9/2001 | Kuenstner |
| 6,292,440 B1 | 9/2001 | Lee |
| 6,300,894 B1 | 10/2001 | Lynch et al. |
| 6,302,855 B1 | 10/2001 | Lav et al. |
| 6,302,869 B1 | 10/2001 | Klitgaard |
| 6,309,370 B1 | 10/2001 | Haim et al. |
| 6,312,888 B1 | 11/2001 | Wong et al. |
| 6,320,547 B1 | 11/2001 | Fathy et al. |
| 6,323,549 B1 | 11/2001 | DeRochemont et al. |
| 6,334,851 B1 | 1/2002 | Hayes et al. |
| 6,363,609 B1 | 4/2002 | Pickren |
| 6,368,314 B1 | 4/2002 | Kipfer et al. |
| 6,375,627 B1 | 4/2002 | Mauze et al. |
| 6,375,638 B2 | 4/2002 | Nason et al. |
| 6,379,301 B1 | 4/2002 | Worthington et al. |
| 6,379,339 B1 | 4/2002 | Klitgaard et al. |
| 6,381,496 B1 | 4/2002 | Meadows et al. |
| 6,397,098 B1 | 5/2002 | Uber et al. |
| 6,402,689 B1 | 6/2002 | Scarantino et al. |
| 6,404,098 B1 | 6/2002 | Kayama et al. |
| 6,413,244 B1 | 7/2002 | Bestetti et al. |
| 6,427,088 B1 | 7/2002 | Bowman et al. |
| D461,241 S | 8/2002 | Moberg et al. |
| D461,891 S | 8/2002 | Moberg |
| 6,434,528 B1 | 8/2002 | Sanders |
| 6,436,072 B1 | 8/2002 | Kullas et al. |
| 6,461,329 B1 | 10/2002 | Van et al. |
| 6,461,331 B1 | 10/2002 | Van Antwerp |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,491,684 B1 | 12/2002 | Joshi et al. |
| 6,492,949 B1 | 12/2002 | Breglia et al. |
| 6,496,149 B1 | 12/2002 | Birnbaum et al. |
| 6,501,415 B1 | 12/2002 | Mana et al. |
| 6,508,788 B2 | 1/2003 | Preuthun |
| 6,512,937 B2 | 1/2003 | Blank et al. |
| 6,520,936 B1 | 2/2003 | Mann |
| 6,524,280 B2 | 2/2003 | Hansen et al. |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,533,183 B2 | 3/2003 | Aasmul et al. |
| 6,537,249 B2 | 3/2003 | Kriesell et al. |
| 6,537,251 B2 | 3/2003 | Klitmose |
| 6,537,268 B1 | 3/2003 | Gibson et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,544,229 B1 | 4/2003 | Danby et al. |
| 6,546,268 B1 | 4/2003 | Ishikawa et al. |
| 6,546,269 B1 | 4/2003 | Kurnik |
| 6,547,764 B2 | 4/2003 | Larsen et al. |
| 6,551,276 B1 | 4/2003 | Mann et al. |
| 6,552,693 B1 | 4/2003 | Leisten |
| 6,553,841 B1 | 4/2003 | Blouch |
| 6,554,798 B1 | 4/2003 | Mann et al. |
| 6,554,800 B1 | 4/2003 | Nezhadian et al. |
| 6,556,850 B1 | 4/2003 | Braig et al. |
| D474,778 S | 5/2003 | Barnes |
| 6,558,320 B1 | 5/2003 | Causey et al. |
| 6,558,345 B1 | 5/2003 | Houben et al. |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,011 B1 | 5/2003 | Buch-Rasmussen et al. |
| 6,562,014 B2 | 5/2003 | Lin et al. |
| 6,564,105 B2 | 5/2003 | Starkweather et al. |

(56) References Cited

U.S. PATENT DOCUMENTS

| | | |
|---|---|---|
| 6,569,115 B1 | 5/2003 | Barker et al. |
| 6,569,125 B2 | 5/2003 | Jepson et al. |
| 6,569,126 B1 | 5/2003 | Poulsen et al. |
| 6,571,128 B2 | 5/2003 | Lebel et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,577,899 B2 | 6/2003 | Lebel et al. |
| 6,580,934 B1 | 6/2003 | Braig et al. |
| 6,582,404 B1 | 6/2003 | Klitgaard et al. |
| 6,583,699 B2 | 6/2003 | Yokoyama |
| 6,585,644 B2 | 7/2003 | Lebel et al. |
| 6,585,699 B2 | 7/2003 | Ljunggreen et al. |
| 6,587,199 B1 | 7/2003 | Luu |
| 6,589,229 B1 | 7/2003 | Connelly et al. |
| 6,595,956 B1 | 7/2003 | Gross et al. |
| 6,599,281 B1 | 7/2003 | Struys et al. |
| 6,605,067 B1 | 8/2003 | Larsen |
| 6,605,072 B2 | 8/2003 | Struys et al. |
| 6,611,419 B1 | 8/2003 | Chakravorty |
| 6,613,019 B2 | 9/2003 | Munk |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,641,533 B2 | 11/2003 | Causey et al. |
| 6,642,908 B2 | 11/2003 | Pleva et al. |
| 6,645,142 B2 | 11/2003 | Braig et al. |
| 6,648,821 B2 | 11/2003 | Lebel et al. |
| 6,650,303 B2 | 11/2003 | Kim et al. |
| 6,650,951 B1 | 11/2003 | Jones et al. |
| 6,653,091 B1 | 11/2003 | Dunn et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,662,030 B2 | 12/2003 | Khalil et al. |
| 6,663,602 B2 | 12/2003 | Moeller |
| 6,668,196 B1 | 12/2003 | Villegas et al. |
| 6,669,663 B1 | 12/2003 | Thompson |
| 6,669,668 B1 | 12/2003 | Kleeman et al. |
| 6,669,669 B2 | 12/2003 | Flaherty et al. |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,685,674 B2 | 2/2004 | Douglas et al. |
| 6,686,406 B2 | 2/2004 | Tomomatsu et al. |
| 6,687,546 B2 | 2/2004 | Ebel et al. |
| 6,689,100 B2 | 2/2004 | Connelly et al. |
| 6,690,192 B1 | 2/2004 | Wing |
| 6,690,336 B1 | 2/2004 | Leisten et al. |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,702,779 B2 | 3/2004 | Connelly et al. |
| 6,715,516 B2 | 4/2004 | Ohms et al. |
| 6,716,198 B2 | 4/2004 | Larsen |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,723,077 B2 | 4/2004 | Pickup et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,446 B2 | 5/2004 | Lebel et al. |
| 6,733,890 B2 | 5/2004 | Imanaka et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,741,148 B2 | 5/2004 | Killen et al. |
| 6,742,249 B2 | 6/2004 | Derochemont et al. |
| 6,743,744 B1 | 6/2004 | Kim et al. |
| 6,744,350 B2 | 6/2004 | Blomquist |
| 6,749,587 B2 | 6/2004 | Flaherty |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,752,785 B2 | 6/2004 | Van et al. |
| 6,752,787 B1 | 6/2004 | Causey et al. |
| 6,753,745 B2 | 6/2004 | Killen et al. |
| 6,753,814 B2 | 6/2004 | Killen et al. |
| 6,758,810 B2 | 7/2004 | Lebel et al. |
| 6,758,835 B2 | 7/2004 | Close et al. |
| 6,761,286 B2 | 7/2004 | Py et al. |
| 6,762,237 B2 | 7/2004 | Glatkowski et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,787,181 B2 | 9/2004 | Uchiyama et al. |
| 6,791,496 B1 | 9/2004 | Killen et al. |
| 6,796,957 B2 | 9/2004 | Carpenter et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Ebel et al. |
| 6,826,031 B2 | 11/2004 | Nagai et al. |
| 6,827,702 B2 | 12/2004 | Lebel et al. |
| 6,830,558 B2 | 12/2004 | Flaherty et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,852,104 B2 | 2/2005 | Blomquist |
| 6,853,288 B2 | 2/2005 | Ahn et al. |
| 6,854,620 B2 | 2/2005 | Ramey |
| 6,854,653 B2 | 2/2005 | Eilersen |
| 6,855,129 B2 | 2/2005 | Jensen et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,878,871 B2 | 4/2005 | Scher et al. |
| 6,883,778 B1 | 4/2005 | Newton et al. |
| 6,890,291 B2 | 5/2005 | Robinson et al. |
| 6,893,415 B2 | 5/2005 | Madsen et al. |
| 6,899,695 B2 | 5/2005 | Herrera |
| 6,899,699 B2 | 5/2005 | Enggaard |
| 6,905,989 B2 | 6/2005 | Ellis et al. |
| 6,906,674 B2 | 6/2005 | McKinzie et al. |
| 6,914,566 B2 | 7/2005 | Beard |
| 6,919,119 B2 | 7/2005 | Kalkan et al. |
| 6,922,590 B1 | 7/2005 | Whitehurst |
| 6,923,763 B1 | 8/2005 | Kovatchev et al. |
| 6,925,393 B1 | 8/2005 | Kalatz et al. |
| 6,928,298 B2 | 8/2005 | Furutani et al. |
| 6,936,006 B2 | 8/2005 | Sabra |
| 6,936,029 B2 | 8/2005 | Mann et al. |
| 6,943,430 B2 | 9/2005 | Kwon |
| 6,943,731 B2 | 9/2005 | Killen et al. |
| 6,945,961 B2 | 9/2005 | Miller et al. |
| 6,948,918 B2 | 9/2005 | Hansen |
| 6,949,081 B1 | 9/2005 | Chance |
| 6,950,708 B2 | 9/2005 | Bowman et al. |
| 6,958,809 B2 | 10/2005 | Sterling et al. |
| 6,960,192 B1 | 11/2005 | Flaherty et al. |

(56) References Cited

U.S. PATENT DOCUMENTS

| | | |
|---|---|---|
| 6,963,259 B2 | 11/2005 | Killen et al. |
| 6,979,326 B2 | 12/2005 | Mann et al. |
| 6,989,891 B2 | 1/2006 | Braig et al. |
| 6,990,366 B2 | 1/2006 | Say et al. |
| 6,997,911 B2 | 2/2006 | Klitmose |
| 6,997,920 B2 | 2/2006 | Mann et al. |
| 7,002,436 B2 | 2/2006 | Ma et al. |
| 7,005,078 B2 | 2/2006 | Van et al. |
| 7,008,399 B2 | 3/2006 | Larsen et al. |
| 7,008,404 B2 | 3/2006 | Nakajima |
| 7,009,180 B2 | 3/2006 | Sterling et al. |
| 7,014,625 B2 | 3/2006 | Bengtsson |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,029,455 B2 | 4/2006 | Flaherty |
| 7,043,288 B2 | 5/2006 | Davis et al. |
| 7,047,637 B2 | 5/2006 | DeRochemont et al. |
| 7,054,836 B2 | 5/2006 | Christensen et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,066,910 B2 | 6/2006 | Bauhahn et al. |
| 7,070,580 B2 | 7/2006 | Nielsen |
| 7,096,124 B2 | 8/2006 | Sterling et al. |
| 7,098,803 B2 | 8/2006 | Mann et al. |
| 7,104,972 B2 | 9/2006 | Moller et al. |
| 7,109,878 B2 | 9/2006 | Mann et al. |
| 7,115,205 B2 | 10/2006 | Robinson et al. |
| 7,116,949 B2 | 10/2006 | Irie et al. |
| 7,123,964 B2 | 10/2006 | Betzold et al. |
| 7,128,727 B2 | 10/2006 | Flaherty et al. |
| 7,133,329 B2 | 11/2006 | Skyggebjerg et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |
| 7,172,572 B2 | 2/2007 | Diamond et al. |
| 7,179,226 B2 | 2/2007 | Crothall et al. |
| 7,190,988 B2 | 3/2007 | Say et al. |
| 7,204,823 B2 | 4/2007 | Estes et al. |
| 7,220,240 B2 | 5/2007 | Struys et al. |
| 7,230,316 B2 | 6/2007 | Yamazaki et al. |
| 7,232,423 B2 | 6/2007 | Mernoee |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,405,698 B2 | 7/2008 | De Rochemont |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van et al. |
| 7,494,481 B2 | 2/2009 | Moberg et al. |
| 7,500,949 B2 | 3/2009 | Gottlieb et al. |
| 7,509,156 B2 | 3/2009 | Flanders |
| D590,415 S | 4/2009 | Ball et al. |
| 7,522,124 B2 | 4/2009 | Smith et al. |
| 7,547,281 B2 | 6/2009 | Hayes et al. |
| 7,553,281 B2 | 6/2009 | Hellwig et al. |
| 7,553,512 B2 | 6/2009 | Kodas et al. |
| 7,564,887 B2 | 7/2009 | Wang et al. |
| 7,569,030 B2 | 8/2009 | Lebel et al. |
| 7,569,050 B2 | 8/2009 | Moberg et al. |
| 7,570,980 B2 | 8/2009 | Ginsberg |
| 7,591,801 B2 | 9/2009 | Brauker et al. |
| 7,595,623 B2 | 9/2009 | Bennett |
| 7,597,682 B2 | 10/2009 | Moberg |
| 7,608,042 B2 | 10/2009 | Goldberger et al. |
| 7,641,649 B2 | 1/2010 | Moberg et al. |
| 7,651,845 B2 | 1/2010 | Doyle et al. |
| 7,652,901 B2 | 1/2010 | Kirchmeier et al. |
| 7,654,982 B2 | 2/2010 | Carlisle et al. |
| 7,670,288 B2 | 3/2010 | Sher |
| 7,680,529 B2 | 3/2010 | Kroll |
| D614,634 S | 4/2010 | Nilsen |
| 7,708,717 B2 | 5/2010 | Estes et al. |
| 7,714,794 B2 | 5/2010 | Tavassoli Hozouri |
| 7,734,323 B2 | 6/2010 | Blomquist et al. |
| 7,763,917 B2 | 7/2010 | De Rochemont |
| 7,766,829 B2 | 8/2010 | Sloan et al. |
| 7,771,391 B2 | 8/2010 | Carter |
| 7,785,258 B2 | 8/2010 | Braig et al. |
| 7,785,313 B2 | 8/2010 | Mastrototaro |
| 7,789,859 B2 | 9/2010 | Estes et al. |
| 7,794,426 B2 | 9/2010 | Briones et al. |
| 7,806,853 B2 | 10/2010 | Wittmann et al. |
| 7,806,854 B2 | 10/2010 | Damiano et al. |
| 7,812,774 B2 | 10/2010 | Friman et al. |
| 7,815,602 B2 | 10/2010 | Mann et al. |
| 7,819,843 B2 | 10/2010 | Mann et al. |
| 7,828,528 B2 | 11/2010 | Estes et al. |
| 7,850,641 B2 | 12/2010 | Lebel et al. |
| 7,904,061 B1 | 3/2011 | Zaffino et al. |
| 7,918,825 B2 | 4/2011 | O'Connor et al. |
| 7,938,797 B2 | 5/2011 | Estes |
| 7,938,801 B2 | 5/2011 | Hawkins et al. |
| 7,946,985 B2 | 5/2011 | Mastrototaro et al. |
| D640,269 S | 6/2011 | Chen |
| 7,959,598 B2 | 6/2011 | Estes |
| 7,967,812 B2 | 6/2011 | Jasperson et al. |
| 7,972,296 B2 | 7/2011 | Braig et al. |
| 7,976,492 B2 | 7/2011 | Brauker et al. |
| 8,029,459 B2 | 10/2011 | Rush et al. |
| 8,062,249 B2 | 11/2011 | Wilinska et al. |
| 8,065,096 B2 | 11/2011 | Moberg et al. |
| 8,066,805 B2 | 11/2011 | Zuercher et al. |
| 8,069,690 B2 | 12/2011 | DeSantolo et al. |
| 8,105,268 B2 | 1/2012 | Lebel et al. |
| 8,114,023 B2 | 2/2012 | Ward et al. |
| 8,114,489 B2 | 2/2012 | Nemat-Nasser et al. |
| 8,152,789 B2 | 4/2012 | Starkweather et al. |
| 8,178,457 B2 | 5/2012 | De Rochemont |
| 8,182,461 B2 | 5/2012 | Pope et al. |
| 8,193,873 B2 | 6/2012 | Kato et al. |
| 8,206,296 B2 | 6/2012 | Jennewine |
| 8,206,350 B2 | 6/2012 | Mann et al. |
| 8,208,984 B2 | 6/2012 | Blomquist et al. |
| 8,221,345 B2 | 7/2012 | Blomquist |
| 8,221,385 B2 | 7/2012 | Estes |
| 8,226,556 B2 | 7/2012 | Hayes et al. |
| 8,246,540 B2 | 8/2012 | Ginsberg |
| 8,251,907 B2 | 8/2012 | Sterling et al. |
| 8,262,616 B2 | 9/2012 | Grant et al. |
| 8,267,893 B2 | 9/2012 | Moberg et al. |
| 8,267,921 B2 | 9/2012 | Yodfat et al. |
| 8,273,052 B2 | 9/2012 | Damiano et al. |
| D669,165 S | 10/2012 | Sims et al. |
| 8,282,626 B2 | 10/2012 | Wenger et al. |
| 8,287,487 B2 | 10/2012 | Estes |
| 8,318,154 B2 | 11/2012 | Frost et al. |
| 8,348,844 B2 | 1/2013 | Kunjan et al. |
| 8,348,886 B2 | 1/2013 | Kanderian et al. |
| 8,348,923 B2 | 1/2013 | Kanderian et al. |
| 8,350,657 B2 | 1/2013 | DeRochemont |
| 8,352,011 B2 | 1/2013 | Van et al. |
| 8,354,294 B2 | 1/2013 | De et al. |
| 8,372,039 B2 | 2/2013 | Mernoe et al. |
| D677,685 S | 3/2013 | Simmons et al. |
| 8,417,311 B2 | 4/2013 | Rule |

(56) References Cited

U.S. PATENT DOCUMENTS

| | | |
|---|---|---|
| 8,430,847 B2 | 4/2013 | Mernoe et al. |
| 8,439,834 B2 | 5/2013 | Schmelzeisen-Redeker et al. |
| 8,439,897 B2 | 5/2013 | Yodfat et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,460,231 B2 | 6/2013 | Brauker et al. |
| 8,467,972 B2 | 6/2013 | Rush |
| 8,467,980 B2 | 6/2013 | Campbell et al. |
| 8,475,409 B2 | 7/2013 | Tsoukalis |
| 8,478,557 B2 | 7/2013 | Hayter et al. |
| 8,480,655 B2 | 7/2013 | Jasperson et al. |
| D688,686 S | 8/2013 | Rhee et al. |
| 8,547,239 B2 | 10/2013 | Peatfield et al. |
| 8,548,544 B2 | 10/2013 | Kircher et al. |
| 8,548,552 B2 | 10/2013 | Tsoukalis |
| 8,551,045 B2 | 10/2013 | Sie et al. |
| 8,560,082 B2 | 10/2013 | Wei |
| 8,560,131 B2 | 10/2013 | Haueter et al. |
| 8,562,558 B2 | 10/2013 | Kamath et al. |
| 8,562,587 B2 | 10/2013 | Kovatchev et al. |
| 8,568,713 B2 | 10/2013 | Frost et al. |
| D693,837 S | 11/2013 | Bouchier |
| 8,579,854 B2 | 11/2013 | Budiman et al. |
| 8,579,879 B2 | 11/2013 | Palerm et al. |
| 8,585,591 B2 | 11/2013 | Sloan et al. |
| 8,585,593 B2 | 11/2013 | Kovatchev et al. |
| 8,585,637 B2 | 11/2013 | Wilinska et al. |
| 8,585,638 B2 | 11/2013 | Blomquist |
| 8,593,819 B2 | 11/2013 | De Rochemont |
| D695,757 S | 12/2013 | Ray et al. |
| 8,597,274 B2 | 12/2013 | Sloan et al. |
| 8,615,366 B2 | 12/2013 | Galley et al. |
| 8,622,988 B2 | 1/2014 | Hayter |
| 8,679,016 B2 | 3/2014 | Mastrototaro et al. |
| 8,679,060 B2 | 3/2014 | Mernoe et al. |
| 8,690,820 B2 | 4/2014 | Cinar et al. |
| 8,694,115 B2 | 4/2014 | Goetz et al. |
| 8,706,691 B2 | 4/2014 | McDaniel et al. |
| 8,715,839 B2 | 5/2014 | De Rochemont |
| 8,718,949 B2 | 5/2014 | Blomquist et al. |
| 8,721,585 B2 | 5/2014 | Brauker et al. |
| 8,727,982 B2 | 5/2014 | Jennewine |
| 8,734,422 B2 | 5/2014 | Hayter |
| 8,734,428 B2 | 5/2014 | Blomquist |
| 8,747,315 B2 | 6/2014 | Brauker et al. |
| 8,762,070 B2 | 6/2014 | Doyle et al. |
| 8,771,222 B2 | 7/2014 | Kanderian et al. |
| 8,777,896 B2 | 7/2014 | Starkweather et al. |
| 8,777,924 B2 | 7/2014 | Kanderian et al. |
| 8,784,364 B2 | 7/2014 | Kamen et al. |
| 8,784,369 B2 | 7/2014 | Starkweather et al. |
| 8,784,370 B2 | 7/2014 | Lebel et al. |
| 8,790,294 B2 | 7/2014 | Estes |
| D710,879 S | 8/2014 | Elston et al. |
| 8,795,224 B2 | 8/2014 | Starkweather et al. |
| 8,795,252 B2 | 8/2014 | Hayter |
| 8,808,230 B2 | 8/2014 | Rotstein |
| 8,810,394 B2 | 8/2014 | Kalpin |
| D714,822 S | 10/2014 | Capua et al. |
| D715,315 S | 10/2014 | Wood |
| D715,815 S | 10/2014 | Bortman et al. |
| 8,852,141 B2 | 10/2014 | Mhatre et al. |
| 8,876,755 B2 | 11/2014 | Taub et al. |
| 8,882,741 B2 | 11/2014 | Brauker et al. |
| D718,779 S | 12/2014 | Hang et al. |
| D720,366 S | 12/2014 | Hiltunen et al. |
| 8,903,501 B2 | 12/2014 | Perryman |
| 8,919,180 B2 | 12/2014 | Gottlieb et al. |
| 8,920,401 B2 | 12/2014 | Brauker et al. |
| D720,765 S | 1/2015 | Xie et al. |
| 8,926,585 B2 | 1/2015 | Brauker et al. |
| 8,939,935 B2 | 1/2015 | O'Connor et al. |
| 8,945,094 B2 | 2/2015 | Nordh |
| 8,956,291 B2 | 2/2015 | Valk et al. |
| 8,956,321 B2 | 2/2015 | DeJournett |
| 8,977,504 B2 | 3/2015 | Hovorka |
| 8,992,475 B2 | 3/2015 | Mann et al. |
| D726,760 S | 4/2015 | Yokota et al. |
| D727,928 S | 4/2015 | Allison et al. |
| D730,378 S | 5/2015 | Xiong et al. |
| 9,034,323 B2 | 5/2015 | Frost et al. |
| D733,175 S | 6/2015 | Bae |
| 9,050,413 B2 | 6/2015 | Brauker et al. |
| 9,056,165 B2 | 6/2015 | Steil et al. |
| 9,056,168 B2 | 6/2015 | Kircher et al. |
| 9,061,097 B2 | 6/2015 | Holt et al. |
| D734,356 S | 7/2015 | Xiong et al. |
| 9,078,963 B2 | 7/2015 | Estes |
| 9,089,305 B2 | 7/2015 | Hovorka |
| D736,811 S | 8/2015 | Teichner et al. |
| D737,305 S | 8/2015 | Scazafavo et al. |
| D737,831 S | 9/2015 | Lee |
| D737,832 S | 9/2015 | Lim et al. |
| D738,901 S | 9/2015 | Amin |
| D740,301 S | 10/2015 | Soegiono et al. |
| D740,308 S | 10/2015 | Kim et al. |
| D740,311 S | 10/2015 | Drozd et al. |
| D741,354 S | 10/2015 | Lee et al. |
| D741,359 S | 10/2015 | Ji-Hye et al. |
| 9,149,233 B2 | 10/2015 | Kamath et al. |
| 9,155,843 B2 | 10/2015 | Brauker et al. |
| 9,171,343 B1 | 10/2015 | Fischell et al. |
| D743,431 S | 11/2015 | Pal et al. |
| D743,991 S | 11/2015 | Pal et al. |
| 9,180,224 B2 | 11/2015 | Moseley et al. |
| 9,180,244 B2 | 11/2015 | Anderson et al. |
| 9,192,716 B2 | 11/2015 | Jugl et al. |
| D744,514 S | 12/2015 | Shin et al. |
| D744,517 S | 12/2015 | Pal et al. |
| D745,032 S | 12/2015 | Pal et al. |
| D745,034 S | 12/2015 | Pal et al. |
| D745,035 S | 12/2015 | Pal et al. |
| D746,827 S | 1/2016 | Jung et al. |
| D746,828 S | 1/2016 | Arai et al. |
| D747,352 S | 1/2016 | Lee et al. |
| 9,233,204 B2 | 1/2016 | Booth et al. |
| D749,097 S | 2/2016 | Zou et al. |
| D749,118 S | 2/2016 | Wang |
| 9,247,901 B2 | 2/2016 | Kamath et al. |
| D751,100 S | 3/2016 | Lindn et al. |
| D752,604 S | 3/2016 | Zhang |
| D753,134 S | 4/2016 | Vazquez |
| D754,718 S | 4/2016 | Zhou |
| 9,314,566 B2 | 4/2016 | Wenger et al. |
| 9,320,471 B2 | 4/2016 | Hayes et al. |
| D755,193 S | 5/2016 | Sun et al. |
| D755,799 S | 5/2016 | Finnis et al. |
| D755,820 S | 5/2016 | Wang |
| D756,387 S | 5/2016 | Chang et al. |
| D757,032 S | 5/2016 | Sabia et al. |
| D757,035 S | 5/2016 | Raskin et al. |
| 9,333,298 B2 | 5/2016 | Kim et al. |
| D758,391 S | 6/2016 | Suarez |
| D758,422 S | 6/2016 | Zhao |
| D759,032 S | 6/2016 | Amin et al. |
| D759,078 S | 6/2016 | Iwamoto |
| D759,678 S | 6/2016 | Jung et al. |
| D759,687 S | 6/2016 | Chang et al. |
| D761,812 S | 7/2016 | Motamedi |
| D763,308 S | 8/2016 | Wang et al. |
| D763,868 S | 8/2016 | Lee et al. |
| D765,110 S | 8/2016 | Liang |
| D765,124 S | 8/2016 | Minks-Brown et al. |
| 9,402,950 B2 | 8/2016 | Dilanni et al. |
| 9,415,157 B2 | 8/2016 | Mann et al. |
| D765,707 S | 9/2016 | Gomez |
| D766,286 S | 9/2016 | Lee et al. |
| D767,586 S | 9/2016 | Kwon et al. |
| D768,154 S | 10/2016 | Kim et al. |
| D768,188 S | 10/2016 | Li et al. |
| D768,660 S | 10/2016 | Wielgosz |
| D768,685 S | 10/2016 | Lee et al. |
| D769,315 S | 10/2016 | Scotti |

(56) References Cited

U.S. PATENT DOCUMENTS

| | | |
|---|---|---|
| 9,474,855 B2 | 10/2016 | McCann et al. |
| D770,507 S | 11/2016 | Umezawa et al. |
| D770,515 S | 11/2016 | Cho et al. |
| D771,073 S | 11/2016 | Choi et al. |
| D771,076 S | 11/2016 | Butcher et al. |
| D771,690 S | 11/2016 | Yin et al. |
| D772,911 S | 11/2016 | Lee et al. |
| 9,480,796 B2 | 11/2016 | Starkweather et al. |
| 9,486,172 B2 | 11/2016 | Cobelli et al. |
| 9,486,571 B2 | 11/2016 | Rosinko |
| 9,486,578 B2 | 11/2016 | Finan et al. |
| D773,531 S | 12/2016 | Toth et al. |
| D775,184 S | 12/2016 | Song et al. |
| D775,196 S | 12/2016 | Huang et al. |
| 9,520,649 B2 | 12/2016 | De Rochemont |
| D775,658 S | 1/2017 | Luo et al. |
| D776,126 S | 1/2017 | Lai et al. |
| D776,687 S | 1/2017 | Wick et al. |
| D777,191 S | 1/2017 | Polimeni |
| D777,758 S | 1/2017 | Kisselev et al. |
| 9,561,324 B2 | 2/2017 | Estes |
| 9,579,456 B2 | 2/2017 | Budiman et al. |
| D781,323 S | 3/2017 | Green et al. |
| D781,781 S | 3/2017 | Schimmoeller, Jr. |
| D781,877 S | 3/2017 | Ko et al. |
| D781,878 S | 3/2017 | Butcher et al. |
| D781,879 S | 3/2017 | Butcher et al. |
| D781,903 S | 3/2017 | Reichle et al. |
| D781,905 S | 3/2017 | Nakaguchi et al. |
| D782,506 S | 3/2017 | Kim et al. |
| D783,672 S | 4/2017 | Rajasankar et al. |
| D785,010 S | 4/2017 | Bachman et al. |
| D785,656 S | 5/2017 | Bramer et al. |
| D786,278 S | 5/2017 | Motamedi |
| D786,898 S | 5/2017 | Hall |
| D788,126 S | 5/2017 | Evnin et al. |
| 9,656,017 B2 | 5/2017 | Greene |
| D788,621 S | 6/2017 | Shallice et al. |
| D788,652 S | 6/2017 | Mutsuro et al. |
| D789,402 S | 6/2017 | Dye et al. |
| D789,967 S | 6/2017 | Kaplan et al. |
| D789,982 S | 6/2017 | Christiana et al. |
| D790,560 S | 6/2017 | Inose et al. |
| D791,781 S | 7/2017 | Donarski et al. |
| D791,805 S | 7/2017 | Segars |
| D791,812 S | 7/2017 | Bistoni et al. |
| D793,412 S | 8/2017 | Chaudhri et al. |
| D795,886 S | 8/2017 | Ng et al. |
| D795,891 S | 8/2017 | Kohan et al. |
| D795,900 S | 8/2017 | Bischoff et al. |
| D795,906 S | 8/2017 | Butrick |
| D795,927 S | 8/2017 | Bischoff et al. |
| 9,743,224 B2 | 8/2017 | San et al. |
| D796,530 S | 9/2017 | McMillan et al. |
| D796,540 S | 9/2017 | McLean et al. |
| D797,116 S | 9/2017 | Chapman et al. |
| D797,763 S | 9/2017 | Kim et al. |
| D797,774 S | 9/2017 | Park et al. |
| D797,797 S | 9/2017 | Gandhi et al. |
| D798,310 S | 9/2017 | Golden et al. |
| D798,311 S | 9/2017 | Golden et al. |
| D799,536 S | 10/2017 | Eder |
| D800,765 S | 10/2017 | Stoksik |
| D800,769 S | 10/2017 | Hennessy et al. |
| D801,383 S | 10/2017 | Park et al. |
| D802,011 S | 11/2017 | Friedman et al. |
| D802,088 S | 11/2017 | Bos et al. |
| D803,232 S | 11/2017 | Leigh et al. |
| D803,242 S | 11/2017 | Mizono et al. |
| D804,502 S | 12/2017 | Amini et al. |
| D805,525 S | 12/2017 | Dascola et al. |
| D806,716 S | 1/2018 | Pahwa et al. |
| D807,376 S | 1/2018 | Mizono et al. |
| D807,400 S | 1/2018 | Lagreca |
| D807,910 S | 1/2018 | Graham et al. |
| D807,918 S | 1/2018 | Cohen et al. |
| D807,919 S | 1/2018 | Cohen et al. |
| D808,423 S | 1/2018 | Jiang et al. |
| D808,974 S | 1/2018 | Chiappone et al. |
| D808,983 S | 1/2018 | Narinedhat et al. |
| 9,857,090 B2 | 1/2018 | Golden et al. |
| 9,878,097 B2 | 1/2018 | Estes |
| D810,116 S | 2/2018 | McLean et al. |
| D810,771 S | 2/2018 | Gandhi et al. |
| 9,889,254 B2 | 2/2018 | Haenggi |
| 9,907,515 B2 | 3/2018 | Doyle et al. |
| D815,131 S | 4/2018 | Thompson et al. |
| D816,090 S | 4/2018 | Stonecipher et al. |
| D817,339 S | 5/2018 | Nanjappan et al. |
| D818,491 S | 5/2018 | Timmer et al. |
| D819,057 S | 5/2018 | Huang |
| D819,059 S | 5/2018 | O'Toole |
| 9,968,729 B2 | 5/2018 | Estes |
| 9,980,140 B1 | 5/2018 | Spencer et al. |
| 9,984,773 B2 | 5/2018 | Gondhalekar et al. |
| D820,311 S | 6/2018 | Cabrera et al. |
| D820,862 S | 6/2018 | Alfonzo et al. |
| D822,034 S | 7/2018 | Clymer et al. |
| D822,677 S | 7/2018 | Weaver et al. |
| D822,684 S | 7/2018 | Clausen-Stuck et al. |
| D822,692 S | 7/2018 | Loychik et al. |
| D823,862 S | 7/2018 | Chung et al. |
| D824,400 S | 7/2018 | Chang et al. |
| D824,951 S | 8/2018 | Kolbrener et al. |
| D826,956 S | 8/2018 | Pillalamarri et al. |
| D826,957 S | 8/2018 | Pillalamarri et al. |
| D828,381 S | 9/2018 | Lee et al. |
| D829,732 S | 10/2018 | Jeffrey et al. |
| D830,374 S | 10/2018 | Leonard et al. |
| D830,384 S | 10/2018 | Lepine et al. |
| D830,385 S | 10/2018 | Lepine et al. |
| D830,407 S | 10/2018 | Kisielius et al. |
| D831,033 S | 10/2018 | Leonard et al. |
| D833,469 S | 11/2018 | Coleman et al. |
| D834,601 S | 11/2018 | Felt |
| D835,132 S | 12/2018 | Ito et al. |
| D835,145 S | 12/2018 | Cashner et al. |
| D835,147 S | 12/2018 | Kisielius et al. |
| D835,651 S | 12/2018 | Bao |
| D835,666 S | 12/2018 | Saleh et al. |
| D836,123 S | 12/2018 | Pillalamarri et al. |
| D837,807 S | 1/2019 | Baber et al. |
| D838,731 S | 1/2019 | Pillalamarri et al. |
| D840,418 S | 2/2019 | Saad et al. |
| D840,419 S | 2/2019 | Saad et al. |
| D844,022 S | 3/2019 | Amin |
| D845,317 S | 4/2019 | Wellmeier et al. |
| 10,248,839 B2 | 4/2019 | Levy et al. |
| D848,459 S | 5/2019 | Li |
| D851,099 S | 6/2019 | Uppala et al. |
| D851,658 S | 6/2019 | Pillalamarri et al. |
| 10,335,464 B1 | 7/2019 | Michelich et al. |
| 10,449,294 B1 | 10/2019 | Estes |
| D865,795 S | 11/2019 | Koo |
| D872,746 S | 1/2020 | Laborde |
| 10,545,132 B2 | 1/2020 | Guthrie et al. |
| D874,471 S | 2/2020 | Pillalamarri et al. |
| D875,114 S | 2/2020 | Clediere |
| 10,569,015 B2 | 2/2020 | Estes |
| 10,583,250 B2 | 3/2020 | Mazlish et al. |
| D880,498 S | 4/2020 | Shahidi et al. |
| D888,070 S | 6/2020 | Yusupov et al. |
| 10,737,015 B2 | 8/2020 | Estes |
| 10,737,024 B2 | 8/2020 | Schmid |
| D904,426 S | 12/2020 | Paul |
| D911,353 S | 2/2021 | Sanchez et al. |
| D914,031 S | 3/2021 | Ding et al. |
| D916,729 S | 4/2021 | Gabriel et al. |
| D916,870 S | 4/2021 | Hemsley |
| D916,878 S | 4/2021 | Kim et al. |
| 10,987,468 B2 | 4/2021 | Mazlish et al. |
| D918,261 S | 5/2021 | Ramamurthy et al. |
| D920,351 S | 5/2021 | Zhang |
| D923,033 S | 6/2021 | Smith et al. |

(56) References Cited

U.S. PATENT DOCUMENTS

| | | |
|---|---|---|
| D927,533 S | 8/2021 | Clymer |
| 11,147,914 B2 * | 10/2021 | Estes .................... A61M 5/158 |
| D938,447 S | 12/2021 | Holland |
| 11,197,964 B2 | 12/2021 | Sjolund et al. |
| 11,260,169 B2 | 3/2022 | Estes |
| D954,078 S | 6/2022 | Rahate et al. |
| 2001/0003542 A1 | 6/2001 | Kita |
| 2001/0021803 A1 | 9/2001 | Blank et al. |
| 2001/0034023 A1 | 10/2001 | Stanton et al. |
| 2001/0034502 A1 | 10/2001 | Moberg et al. |
| 2001/0041869 A1 | 11/2001 | Causey et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |
| 2001/0056258 A1 | 12/2001 | Evans |
| 2001/0056262 A1 | 12/2001 | Cabiri et al. |
| 2002/0004651 A1 | 1/2002 | Ljunggreen et al. |
| 2002/0007154 A1 | 1/2002 | Hansen et al. |
| 2002/0010401 A1 | 1/2002 | Bushmakin et al. |
| 2002/0010423 A1 | 1/2002 | Gross et al. |
| 2002/0013784 A1 | 1/2002 | Swanson |
| 2002/0016534 A1 | 2/2002 | Trepagnier et al. |
| 2002/0016568 A1 | 2/2002 | Lebel et al. |
| 2002/0032402 A1 | 3/2002 | Daoud et al. |
| 2002/0040208 A1 | 4/2002 | Flaherty et al. |
| 2002/0046315 A1 | 4/2002 | Miller et al. |
| 2002/0047768 A1 | 4/2002 | Duffy |
| 2002/0055845 A1 | 5/2002 | Jeda et al. |
| 2002/0070983 A1 | 6/2002 | Kozub et al. |
| 2002/0072720 A1 | 6/2002 | Hague et al. |
| 2002/0091358 A1 | 7/2002 | Klitmose |
| 2002/0107476 A1 | 8/2002 | Mann et al. |
| 2002/0123740 A1 | 9/2002 | Flaherty et al. |
| 2002/0126036 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0156462 A1 | 10/2002 | Stultz |
| 2002/0161288 A1 | 10/2002 | Shin et al. |
| 2002/0164973 A1 | 11/2002 | Janik et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |
| 2003/0023152 A1 | 1/2003 | Abbink et al. |
| 2003/0034124 A1 | 2/2003 | Sugaya et al. |
| 2003/0040715 A1 | 2/2003 | D'Antonio et al. |
| 2003/0050621 A1 | 3/2003 | Lebel et al. |
| 2003/0055380 A1 | 3/2003 | Flaherty |
| 2003/0060692 A1 | 3/2003 | L. Ruchti et al. |
| 2003/0065308 A1 | 4/2003 | Lebel et al. |
| 2003/0086073 A1 | 5/2003 | Braig et al. |
| 2003/0086074 A1 | 5/2003 | Braig et al. |
| 2003/0086075 A1 | 5/2003 | Braig et al. |
| 2003/0088238 A1 | 5/2003 | Poulsen et al. |
| 2003/0090649 A1 | 5/2003 | Sterling et al. |
| 2003/0100040 A1 | 5/2003 | Bonnecaze et al. |
| 2003/0104982 A1 | 6/2003 | Wittmann et al. |
| 2003/0121055 A1 | 6/2003 | Kaminski et al. |
| 2003/0122647 A1 | 7/2003 | Ou |
| 2003/0125672 A1 | 7/2003 | Adair et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0161744 A1 | 8/2003 | Vilks et al. |
| 2003/0163097 A1 | 8/2003 | Fleury et al. |
| 2003/0170436 A1 | 9/2003 | Sumi et al. |
| 2003/0175806 A1 | 9/2003 | Rule et al. |
| 2003/0195404 A1 | 10/2003 | Knobbe et al. |
| 2003/0198558 A1 | 10/2003 | Nason et al. |
| 2003/0199825 A1 | 10/2003 | Flaherty |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0216683 A1 | 11/2003 | Shekalim |
| 2003/0216686 A1 | 11/2003 | Lynch et al. |
| 2003/0220605 A1 | 11/2003 | Bowman et al. |
| 2003/0221621 A1 | 12/2003 | Pokharna et al. |
| 2003/0236498 A1 | 12/2003 | Gross et al. |
| 2004/0001027 A1 | 1/2004 | Killen et al. |
| 2004/0006316 A1 | 1/2004 | Patton |
| 2004/0010207 A1 | 1/2004 | Flaherty et al. |
| 2004/0019325 A1 | 1/2004 | Shekalim |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064096 A1 | 4/2004 | Flaherty et al. |
| 2004/0064259 A1 | 4/2004 | Haaland et al. |
| 2004/0068224 A1 | 4/2004 | Couvillon et al. |
| 2004/0068230 A1 | 4/2004 | Estes et al. |
| 2004/0069004 A1 | 4/2004 | Gist et al. |
| 2004/0069044 A1 | 4/2004 | Lavi et al. |
| 2004/0078028 A1 | 4/2004 | Flaherty et al. |
| 2004/0087894 A1 | 5/2004 | Flaherty |
| 2004/0087904 A1 | 5/2004 | Langley et al. |
| 2004/0092865 A1 | 5/2004 | Flaherty et al. |
| 2004/0092878 A1 | 5/2004 | Flaherty |
| 2004/0097796 A1 | 5/2004 | Berman et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0127844 A1 | 7/2004 | Flaherty |
| 2004/0133166 A1 | 7/2004 | Moberg et al. |
| 2004/0147034 A1 | 7/2004 | Gore et al. |
| 2004/0153032 A1 | 8/2004 | Garribotto et al. |
| 2004/0158207 A1 | 8/2004 | Hunn et al. |
| 2004/0171983 A1 | 9/2004 | Sparks et al. |
| 2004/0176720 A1 | 9/2004 | Kipfer |
| 2004/0176727 A1 | 9/2004 | Shekalim |
| 2004/0187952 A1 | 9/2004 | Jones |
| 2004/0203357 A1 | 10/2004 | Nassimi |
| 2004/0204673 A1 | 10/2004 | Flaherty |
| 2004/0204744 A1 | 10/2004 | Penner et al. |
| 2004/0204868 A1 | 10/2004 | Maynard et al. |
| 2004/0215492 A1 | 10/2004 | Choi |
| 2004/0220551 A1 | 11/2004 | Flaherty et al. |
| 2004/0235446 A1 | 11/2004 | Flaherty et al. |
| 2004/0241736 A1 | 12/2004 | Hendee et al. |
| 2004/0249308 A1 | 12/2004 | Forssell |
| 2004/0260233 A1 | 12/2004 | Garibotto et al. |
| 2005/0003470 A1 | 1/2005 | Nelson et al. |
| 2005/0010165 A1 | 1/2005 | Hickle |
| 2005/0020980 A1 | 1/2005 | Inoue et al. |
| 2005/0021005 A1 | 1/2005 | Flaherty et al. |
| 2005/0021104 A1 | 1/2005 | DiLorenzo |
| 2005/0022274 A1 | 1/2005 | Campbell et al. |
| 2005/0033148 A1 | 2/2005 | Haueter et al. |
| 2005/0038332 A1 | 2/2005 | Saidara et al. |
| 2005/0049179 A1 | 3/2005 | Davidson et al. |
| 2005/0065464 A1 | 3/2005 | Talbot et al. |
| 2005/0065760 A1 | 3/2005 | Murtfeldt et al. |
| 2005/0075624 A1 | 4/2005 | Miesel |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0101933 A1 | 5/2005 | Marrs et al. |
| 2005/0105095 A1 | 5/2005 | Pesach et al. |
| 2005/0107743 A1 | 5/2005 | Fangrow |
| 2005/0113745 A1 | 5/2005 | Stultz |
| 2005/0124866 A1 | 6/2005 | Elaz et al. |
| 2005/0134609 A1 | 6/2005 | Yu |
| 2005/0137530 A1 | 6/2005 | Campbell et al. |
| 2005/0137573 A1 | 6/2005 | McLaughlin |
| 2005/0160858 A1 | 7/2005 | Mernoe |
| 2005/0171503 A1 | 8/2005 | Van et al. |
| 2005/0171512 A1 | 8/2005 | Flaherty |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0192561 A1 | 9/2005 | Mernoe |
| 2005/0197621 A1 | 9/2005 | Poulsen et al. |
| 2005/0203360 A1 | 9/2005 | Brauker et al. |

(56) References Cited

U.S. PATENT DOCUMENTS

| | | |
|---|---|---|
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0240544 A1 | 10/2005 | Kil et al. |
| 2005/0245878 A1 | 11/2005 | Mernoe et al. |
| 2005/0251097 A1 | 11/2005 | Mernoe |
| 2005/0261660 A1 | 11/2005 | Choi |
| 2005/0262451 A1 | 11/2005 | Remignanti et al. |
| 2005/0267402 A1 | 12/2005 | Stewart et al. |
| 2005/0272640 A1 | 12/2005 | Doyle et al. |
| 2005/0273059 A1 | 12/2005 | Mernoe et al. |
| 2005/0277890 A1 | 12/2005 | Stewart et al. |
| 2005/0277912 A1 | 12/2005 | John |
| 2006/0009727 A1 | 1/2006 | O'Mahony et al. |
| 2006/0036214 A1 | 2/2006 | Mogensen et al. |
| 2006/0041229 A1 | 2/2006 | Garibotto et al. |
| 2006/0042633 A1 | 3/2006 | Bishop et al. |
| 2006/0064053 A1 | 3/2006 | Bollish et al. |
| 2006/0069351 A9 | 3/2006 | Safabash et al. |
| 2006/0069382 A1 | 3/2006 | Pedersen |
| 2006/0074381 A1 | 4/2006 | Malave et al. |
| 2006/0075269 A1 | 4/2006 | Liong et al. |
| 2006/0079765 A1 | 4/2006 | Neer et al. |
| 2006/0079809 A1 | 4/2006 | Goldberger et al. |
| 2006/0086994 A1 | 4/2006 | Viefers et al. |
| 2006/0095014 A1 | 5/2006 | Ethelfeld |
| 2006/0100494 A1 | 5/2006 | Kroll |
| 2006/0125654 A1 | 6/2006 | Liao et al. |
| 2006/0134323 A1 | 6/2006 | O'Brien |
| 2006/0134491 A1 | 6/2006 | Hilchenko et al. |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0167350 A1 | 7/2006 | Monfre et al. |
| 2006/0173410 A1 | 8/2006 | Moberg et al. |
| 2006/0178633 A1 | 8/2006 | Garibotto et al. |
| 2006/0184104 A1 | 8/2006 | Cheney et al. |
| 2006/0184119 A1 | 8/2006 | Remde et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0200073 A1 | 9/2006 | Radmer et al. |
| 2006/0204535 A1 | 9/2006 | Johnson |
| 2006/0206054 A1 | 9/2006 | Shekalim |
| 2006/0214511 A1 | 9/2006 | Dayan |
| 2006/0229531 A1 | 10/2006 | Goldberger et al. |
| 2006/0247574 A1 | 11/2006 | Maule et al. |
| 2006/0247581 A1 | 11/2006 | Pedersen et al. |
| 2006/0253085 A1 | 11/2006 | Geismar et al. |
| 2006/0253086 A1 | 11/2006 | Moberg et al. |
| 2006/0258973 A1 | 11/2006 | Volt |
| 2006/0258976 A1 | 11/2006 | Shturman et al. |
| 2006/0264835 A1 | 11/2006 | Nielsen et al. |
| 2006/0264890 A1 | 11/2006 | Moberg et al. |
| 2006/0264894 A1 | 11/2006 | Moberg et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060870 A1 | 3/2007 | Tolle et al. |
| 2007/0060872 A1 | 3/2007 | Hall et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0078818 A1 | 4/2007 | Zivitz et al. |
| 2007/0079836 A1 | 4/2007 | Reghabi et al. |
| 2007/0083160 A1 | 4/2007 | Hall et al. |
| 2007/0088271 A1 | 4/2007 | Richards |
| 2007/0093750 A1 | 4/2007 | Jan et al. |
| 2007/0093786 A1 | 4/2007 | Goldsmith et al. |
| 2007/0100222 A1 | 5/2007 | Mastrototaro et al. |
| 2007/0100635 A1 | 5/2007 | Mahajan et al. |
| 2007/0106135 A1 | 5/2007 | Sloan et al. |
| 2007/0106218 A1 | 5/2007 | Yodfat et al. |
| 2007/0112298 A1 | 5/2007 | Mueller et al. |
| 2007/0116601 A1 | 5/2007 | Patton |
| 2007/0118364 A1 | 5/2007 | Wise et al. |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0129690 A1 | 6/2007 | Rosenblatt et al. |
| 2007/0142720 A1 | 6/2007 | Ridder et al. |
| 2007/0142776 A9 | 6/2007 | Kovelman et al. |
| 2007/0155307 A1 | 7/2007 | Ng et al. |
| 2007/0156092 A1 | 7/2007 | Estes et al. |
| 2007/0156094 A1 | 7/2007 | Safabash et al. |
| 2007/0166170 A1 | 7/2007 | Nason et al. |
| 2007/0166453 A1 | 7/2007 | Van et al. |
| 2007/0167905 A1 | 7/2007 | Estes et al. |
| 2007/0167912 A1 | 7/2007 | Causey et al. |
| 2007/0169607 A1 | 7/2007 | Keller et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0179444 A1 | 8/2007 | Causey et al. |
| 2007/0191702 A1 | 8/2007 | Yodfat et al. |
| 2007/0191716 A1 | 8/2007 | Goldberger et al. |
| 2007/0197163 A1 | 8/2007 | Robertson |
| 2007/0219432 A1 | 9/2007 | Thompson |
| 2007/0219480 A1 | 9/2007 | Kamen et al. |
| 2007/0225675 A1 | 9/2007 | Robinson et al. |
| 2007/0233521 A1 | 10/2007 | Wehba et al. |
| 2007/0239116 A1 | 10/2007 | Follman et al. |
| 2007/0244381 A1 | 10/2007 | Robinson et al. |
| 2007/0248238 A1 | 10/2007 | Abreu |
| 2007/0249007 A1 | 10/2007 | Rosero |
| 2007/0252774 A1 | 11/2007 | Qi et al. |
| 2007/0255250 A1 | 11/2007 | Moberg et al. |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0282299 A1 | 12/2007 | Hellwig |
| 2007/0287931 A1 | 12/2007 | Dilorenzo |
| 2007/0287985 A1 | 12/2007 | Estes et al. |
| 2007/0293843 A1 | 12/2007 | Ireland et al. |
| 2008/0009824 A1 | 1/2008 | Moberg et al. |
| 2008/0015422 A1 | 1/2008 | Wessel |
| 2008/0027574 A1 | 1/2008 | Thomas |
| 2008/0031481 A1 | 2/2008 | Warren et al. |
| 2008/0033272 A1 | 2/2008 | Gough et al. |
| 2008/0033320 A1 | 2/2008 | Racchini et al. |
| 2008/0045891 A1 | 2/2008 | Maule et al. |
| 2008/0051697 A1 | 2/2008 | Mounce et al. |
| 2008/0051698 A1 | 2/2008 | Mounce et al. |
| 2008/0051714 A1 | 2/2008 | Moberg et al. |
| 2008/0051716 A1 | 2/2008 | Stutz |
| 2008/0051730 A1 | 2/2008 | Bikovsky |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0077081 A1 | 3/2008 | Mounce et al. |
| 2008/0078400 A1 | 4/2008 | Martens et al. |
| 2008/0097289 A1 | 4/2008 | Steil et al. |
| 2008/0097326 A1 | 4/2008 | Moberg et al. |
| 2008/0097375 A1 | 4/2008 | Bikovsky |
| 2008/0097381 A1 | 4/2008 | Moberg et al. |
| 2008/0103022 A1 | 5/2008 | Dvorak et al. |
| 2008/0109050 A1 | 5/2008 | John |
| 2008/0114304 A1 | 5/2008 | Nalesso et al. |
| 2008/0125700 A1 | 5/2008 | Moberg et al. |
| 2008/0125701 A1 | 5/2008 | Moberg et al. |
| 2008/0129535 A1 | 6/2008 | Thompson et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |

(56) References Cited

U.S. PATENT DOCUMENTS

| | | |
|---|---|---|
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0177149 A1 | 7/2008 | Weinert et al. |
| 2008/0183060 A1 | 7/2008 | Steil et al. |
| 2008/0188796 A1 | 8/2008 | Steil et al. |
| 2008/0198012 A1 | 8/2008 | Kamen |
| 2008/0200838 A1 | 8/2008 | Goldberger et al. |
| 2008/0201325 A1 | 8/2008 | Doniger et al. |
| 2008/0206067 A1 | 8/2008 | De et al. |
| 2008/0208113 A1 | 8/2008 | Damiano et al. |
| 2008/0208627 A1 | 8/2008 | Skyggebjerg |
| 2008/0214919 A1 | 9/2008 | Harmon et al. |
| 2008/0215035 A1 | 9/2008 | Yodfat et al. |
| 2008/0228056 A1 | 9/2008 | Blomquist et al. |
| 2008/0234630 A1 | 9/2008 | Iddan et al. |
| 2008/0249386 A1 | 10/2008 | Besterman et al. |
| 2008/0255516 A1 | 10/2008 | Yodfat et al. |
| 2008/0269585 A1 | 10/2008 | Ginsberg |
| 2008/0269683 A1 | 10/2008 | Bikovsky |
| 2008/0269687 A1 | 10/2008 | Chong et al. |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2008/0294094 A1 | 11/2008 | Mhatre et al. |
| 2008/0294109 A1 | 11/2008 | Estes et al. |
| 2008/0294142 A1 | 11/2008 | Patel et al. |
| 2008/0300572 A1 | 12/2008 | Rankers et al. |
| 2008/0306434 A1 | 12/2008 | Dobbles et al. |
| 2008/0306444 A1 | 12/2008 | Brister et al. |
| 2008/0312512 A1 | 12/2008 | Brukalo et al. |
| 2008/0312634 A1 | 12/2008 | Helmerson et al. |
| 2008/0319381 A1 | 12/2008 | Yodfat et al. |
| 2008/0319383 A1 | 12/2008 | Byland et al. |
| 2008/0319384 A1 | 12/2008 | Yodfat et al. |
| 2008/0319394 A1 | 12/2008 | Yodfat et al. |
| 2008/0319414 A1 | 12/2008 | Yodfat et al. |
| 2008/0319416 A1 | 12/2008 | Yodfat et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0036760 A1 | 2/2009 | Hayter |
| 2009/0036870 A1 | 2/2009 | Mounce et al. |
| 2009/0043240 A1 | 2/2009 | Robinson et al. |
| 2009/0043291 A1 | 2/2009 | Thompson |
| 2009/0048584 A1 | 2/2009 | Thompson |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0076453 A1 | 3/2009 | Mejlhede et al. |
| 2009/0076849 A1 | 3/2009 | Diller |
| 2009/0082728 A1 | 3/2009 | Bikovsky |
| 2009/0093756 A1 | 4/2009 | Minaie et al. |
| 2009/0099507 A1 | 4/2009 | Koops |
| 2009/0099521 A1 | 4/2009 | Gravesen et al. |
| 2009/0105573 A1 | 4/2009 | Malecha |
| 2009/0105636 A1 | 4/2009 | Hayter et al. |
| 2009/0112333 A1 | 4/2009 | Sahai |
| 2009/0118664 A1 | 5/2009 | Estes et al. |
| 2009/0131861 A1 | 5/2009 | Braig et al. |
| 2009/0143916 A1 | 6/2009 | Boll et al. |
| 2009/0156922 A1 | 6/2009 | Goldberger et al. |
| 2009/0156924 A1 | 6/2009 | Shariati et al. |
| 2009/0156990 A1 | 6/2009 | Wenger et al. |
| 2009/0163781 A1 | 6/2009 | Say et al. |
| 2009/0164190 A1 | 6/2009 | Hayter |
| 2009/0177142 A1 | 7/2009 | Blomquist et al. |
| 2009/0177154 A1 | 7/2009 | Blomquist |
| 2009/0192722 A1 | 7/2009 | Shariati et al. |
| 2009/0198191 A1 | 8/2009 | Chong et al. |
| 2009/0198215 A1 | 8/2009 | Chong et al. |
| 2009/0198350 A1 | 8/2009 | Thiele |
| 2009/0212966 A1 | 8/2009 | Panduro |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2009/0326472 A1 | 12/2009 | Carter et al. |
| 2010/0010330 A1 | 1/2010 | Rankers et al. |
| 2010/0017141 A1 | 1/2010 | Campbell et al. |
| 2010/0036326 A1 | 2/2010 | Matusch |
| 2010/0057040 A1 | 3/2010 | Hayter |
| 2010/0057041 A1 | 3/2010 | Hayter |
| 2010/0064243 A1 | 3/2010 | Buck et al. |
| 2010/0077198 A1 | 3/2010 | Buck et al. |
| 2010/0094078 A1 | 4/2010 | Weston |
| 2010/0094251 A1* | 4/2010 | Estes ............ A61B 34/10 604/504 |
| 2010/0114026 A1 | 5/2010 | Karratt et al. |
| 2010/0121167 A1 | 5/2010 | McGarraugh |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0165795 A1 | 7/2010 | Elder et al. |
| 2010/0168538 A1 | 7/2010 | Keenan et al. |
| 2010/0168820 A1 | 7/2010 | Maniak et al. |
| 2010/0174228 A1 | 7/2010 | Buckingham et al. |
| 2010/0174229 A1 | 7/2010 | Hsu et al. |
| 2010/0174266 A1 | 7/2010 | Estes |
| 2010/0179409 A1 | 7/2010 | Kamath et al. |
| 2010/0185183 A1 | 7/2010 | Alme et al. |
| 2010/0211003 A1 | 8/2010 | Sundar et al. |
| 2010/0211005 A1* | 8/2010 | Edwards ............ A61P 19/02 604/82 |
| 2010/0241066 A1 | 9/2010 | Hansen et al. |
| 2010/0249530 A1 | 9/2010 | Rankers et al. |
| 2010/0262117 A1 | 10/2010 | Magni et al. |
| 2010/0262434 A1 | 10/2010 | Shaya |
| 2010/0273738 A1 | 10/2010 | Valcke et al. |
| 2010/0286601 A1 | 11/2010 | Yodfat et al. |
| 2010/0286653 A1 | 11/2010 | Kubel et al. |
| 2010/0298685 A1 | 11/2010 | Hayter et al. |
| 2010/0298765 A1 | 11/2010 | Budiman et al. |
| 2010/0324382 A1 | 12/2010 | Cantwell et al. |
| 2010/0324977 A1 | 12/2010 | Dragt |
| 2010/0325864 A1 | 12/2010 | Briones et al. |
| 2011/0009813 A1 | 1/2011 | Rankers |
| 2011/0015511 A1 | 1/2011 | Bousamra et al. |
| 2011/0021584 A1 | 1/2011 | Berggren et al. |
| 2011/0028817 A1 | 2/2011 | Jin et al. |
| 2011/0040247 A1 | 2/2011 | Mandro et al. |
| 2011/0049394 A1 | 3/2011 | De Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071464 A1 | 3/2011 | Palerm |
| 2011/0071765 A1 | 3/2011 | Yodfat et al. |
| 2011/0098637 A1 | 4/2011 | Hill |
| 2011/0098674 A1 | 4/2011 | Vicente et al. |
| 2011/0105955 A1 | 5/2011 | Yudovsky et al. |
| 2011/0106050 A1 | 5/2011 | Yodfat et al. |
| 2011/0118699 A1 | 5/2011 | Yodfat et al. |
| 2011/0124996 A1 | 5/2011 | Reinke et al. |
| 2011/0130716 A1 | 6/2011 | Estes et al. |
| 2011/0144586 A1 | 6/2011 | Michaud et al. |
| 2011/0160652 A1 | 6/2011 | Yodfat et al. |
| 2011/0163880 A1 | 7/2011 | Halff et al. |
| 2011/0178472 A1 | 7/2011 | Cabiri |
| 2011/0190694 A1 | 8/2011 | Lanier et al. |
| 2011/0199194 A1 | 8/2011 | Waldock et al. |
| 2011/0202005 A1 | 8/2011 | Yodfat et al. |
| 2011/0218495 A1 | 9/2011 | Remde |
| 2011/0224523 A1 | 9/2011 | Budiman |
| 2011/0230833 A1 | 9/2011 | Landman et al. |
| 2011/0251509 A1 | 10/2011 | Beyhan et al. |
| 2011/0313390 A1 | 12/2011 | Roy et al. |
| 2011/0313680 A1 | 12/2011 | Doyle et al. |

(56) References Cited

U.S. PATENT DOCUMENTS

| | | |
|---|---|---|
| 2011/0316562 A1 | 12/2011 | Cefai et al. |
| 2011/0319813 A1 | 12/2011 | Kamen et al. |
| 2012/0003935 A1 | 1/2012 | Lydon et al. |
| 2012/0010594 A1 | 1/2012 | Holt et al. |
| 2012/0016304 A1 | 1/2012 | Patel et al. |
| 2012/0029468 A1 | 2/2012 | Diperna et al. |
| 2012/0030393 A1 | 2/2012 | Ganesh et al. |
| 2012/0046606 A1 | 2/2012 | Arefieg |
| 2012/0053556 A1 | 3/2012 | Lee |
| 2012/0065894 A1 | 3/2012 | Tubb et al. |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0124521 A1 | 5/2012 | Guo |
| 2012/0150446 A1 | 6/2012 | Chang et al. |
| 2012/0150556 A1 | 6/2012 | Galasso et al. |
| 2012/0172694 A1 | 7/2012 | Desborough et al. |
| 2012/0172802 A1 | 7/2012 | Blomquist |
| 2012/0185267 A1 | 7/2012 | Kamen et al. |
| 2012/0190955 A1 | 7/2012 | Rao et al. |
| 2012/0197207 A1 | 8/2012 | Stefanski |
| 2012/0203085 A1 | 8/2012 | Rebec |
| 2012/0203178 A1 | 8/2012 | Tverskoy |
| 2012/0203467 A1 | 8/2012 | Kamath et al. |
| 2012/0209208 A1 | 8/2012 | Stefanski |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0227737 A1 | 9/2012 | Mastrototaro et al. |
| 2012/0232520 A1 | 9/2012 | Sloan et al. |
| 2012/0238851 A1* | 9/2012 | Kamen ............ A61M 5/14244 604/151 |
| 2012/0238853 A1 | 9/2012 | Arefieg |
| 2012/0238999 A1 | 9/2012 | Estes et al. |
| 2012/0245448 A1 | 9/2012 | Shariati et al. |
| 2012/0245556 A1 | 9/2012 | Kovatchev et al. |
| 2012/0245855 A1 | 9/2012 | Kamath et al. |
| 2012/0246106 A1 | 9/2012 | Atlas et al. |
| 2012/0250449 A1 | 10/2012 | Nakano |
| 2012/0259191 A1 | 10/2012 | Shariati et al. |
| 2012/0271655 A1 | 10/2012 | Knobel et al. |
| 2012/0277668 A1 | 11/2012 | Chawla |
| 2012/0277723 A1 | 11/2012 | Skladnev et al. |
| 2012/0282111 A1 | 11/2012 | Nip et al. |
| 2012/0283694 A1 | 11/2012 | Yodfat et al. |
| 2012/0289931 A1 | 11/2012 | Robinson et al. |
| 2012/0295550 A1 | 11/2012 | Wilson et al. |
| 2012/0302991 A1 | 11/2012 | Blomquist et al. |
| 2012/0323590 A1* | 12/2012 | Udani ................ G06Q 10/103 348/40 |
| 2012/0330270 A1 | 12/2012 | Colton |
| 2013/0030358 A1 | 1/2013 | Yodfat et al. |
| 2013/0046281 A1 | 2/2013 | Javitt |
| 2013/0053818 A1 | 2/2013 | Estes |
| 2013/0053819 A1 | 2/2013 | Estes |
| 2013/0053820 A1 | 2/2013 | Estes et al. |
| 2013/0102867 A1 | 4/2013 | Desborough et al. |
| 2013/0116649 A1 | 5/2013 | Breton et al. |
| 2013/0138205 A1 | 5/2013 | Kushwaha et al. |
| 2013/0158503 A1 | 6/2013 | Kanderian et al. |
| 2013/0159456 A1 | 6/2013 | Daoud et al. |
| 2013/0165041 A1 | 6/2013 | Bukovjan et al. |
| 2013/0172695 A1 | 7/2013 | Nielsen et al. |
| 2013/0172710 A1 | 7/2013 | Mears et al. |
| 2013/0178791 A1 | 7/2013 | Javitt |
| 2013/0204186 A1 | 8/2013 | Moore et al. |
| 2013/0204202 A1* | 8/2013 | Trombly ............ A61M 5/16877 604/207 |
| 2013/0218126 A1 | 8/2013 | Hayter et al. |
| 2013/0231642 A1 | 9/2013 | Doyle et al. |
| 2013/0237932 A1 | 9/2013 | Thueer et al. |
| 2013/0245545 A1 | 9/2013 | Arnold et al. |
| 2013/0245563 A1 | 9/2013 | Mercer et al. |
| 2013/0245604 A1 | 9/2013 | Kouyoumjian et al. |
| 2013/0253284 A1* | 9/2013 | Fraier .................... G16H 50/80 600/300 |
| 2013/0253418 A1 | 9/2013 | Kamath et al. |
| 2013/0253472 A1 | 9/2013 | Cabiri |
| 2013/0261406 A1 | 10/2013 | Rebec et al. |
| 2013/0275139 A1 | 10/2013 | Coleman |
| 2013/0281965 A1* | 10/2013 | Kamen ................ G16H 20/17 604/67 |
| 2013/0296792 A1 | 11/2013 | Cabiri |
| 2013/0296823 A1 | 11/2013 | Melker et al. |
| 2013/0297334 A1 | 11/2013 | Galasso et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | O'Connor et al. |
| 2013/0338629 A1 | 12/2013 | Agrawal et al. |
| 2013/0338630 A1 | 12/2013 | Agrawal et al. |
| 2013/0345663 A1 | 12/2013 | Agrawal et al. |
| 2013/0346858 A1 | 12/2013 | Neyrinck |
| 2014/0005633 A1 | 1/2014 | Finan |
| 2014/0018730 A1 | 1/2014 | Stephan |
| 2014/0025015 A1 | 1/2014 | Cross et al. |
| 2014/0031759 A1 | 1/2014 | Kouyoumjian et al. |
| 2014/0032549 A1 | 1/2014 | McDaniel et al. |
| 2014/0039383 A1 | 2/2014 | Dobbles et al. |
| 2014/0052091 A1 | 2/2014 | Dobbles et al. |
| 2014/0052092 A1 | 2/2014 | Dobbles et al. |
| 2014/0052093 A1 | 2/2014 | Dobbles et al. |
| 2014/0052094 A1 | 2/2014 | Dobbles et al. |
| 2014/0052095 A1 | 2/2014 | Dobbles et al. |
| 2014/0066859 A1 | 3/2014 | Ogawa et al. |
| 2014/0066884 A1 | 3/2014 | Keenan et al. |
| 2014/0066885 A1 | 3/2014 | Keenan et al. |
| 2014/0066886 A1 | 3/2014 | Roy et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0066890 A1 | 3/2014 | Sloan et al. |
| 2014/0066892 A1 | 3/2014 | Keenan et al. |
| 2014/0074033 A1 | 3/2014 | Sonderegger et al. |
| 2014/0088428 A1 | 3/2014 | Yang et al. |
| 2014/0088557 A1 | 3/2014 | Mernoe et al. |
| 2014/0094766 A1 | 4/2014 | Estes et al. |
| 2014/0107607 A1 | 4/2014 | Estes |
| 2014/0108046 A1 | 4/2014 | Echeverria et al. |
| 2014/0114278 A1 | 4/2014 | Dobbles et al. |
| 2014/0121635 A1 | 5/2014 | Hayter |
| 2014/0127048 A1 | 5/2014 | Diianni et al. |
| 2014/0128705 A1 | 5/2014 | Mazlish |
| 2014/0128803 A1 | 5/2014 | Dobbles et al. |
| 2014/0128839 A1 | 5/2014 | Diianni et al. |
| 2014/0129951 A1 | 5/2014 | Amin et al. |
| 2014/0135880 A1 | 5/2014 | Baumgartner et al. |
| 2014/0142508 A1 | 5/2014 | Diianni et al. |
| 2014/0146202 A1 | 5/2014 | Boss et al. |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0228627 A1 | 8/2014 | Soffer et al. |
| 2014/0228668 A1 | 8/2014 | Wakizaka et al. |
| 2014/0230021 A1 | 8/2014 | Birtwhistle et al. |
| 2014/0235981 A1 | 8/2014 | Hayter |
| 2014/0249500 A1 | 9/2014 | Estes |
| 2014/0276553 A1 | 9/2014 | Rosinko et al. |
| 2014/0276554 A1 | 9/2014 | Finan et al. |
| 2014/0276555 A1 | 9/2014 | Morales |
| 2014/0276556 A1 | 9/2014 | Saint et al. |
| 2014/0276583 A1 | 9/2014 | Chen et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0323959 A1 | 10/2014 | Ebel et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025471 A1 | 1/2015 | Enggaard |

(56) References Cited

U.S. PATENT DOCUMENTS

| | | |
|---|---|---|
| 2015/0025495 A1 | 1/2015 | Peyser |
| 2015/0025503 A1 | 1/2015 | Searle et al. |
| 2015/0030641 A1 | 1/2015 | Anderson et al. |
| 2015/0041498 A1 | 2/2015 | Kakiuchi et al. |
| 2015/0045737 A1 | 2/2015 | Stefanski |
| 2015/0073337 A1 | 3/2015 | Saint et al. |
| 2015/0080789 A1 | 3/2015 | Estes et al. |
| 2015/0120317 A1 | 4/2015 | Mayou et al. |
| 2015/0120323 A1 | 4/2015 | Galasso et al. |
| 2015/0134265 A1 | 5/2015 | Kohlbrecher et al. |
| 2015/0134353 A1 | 5/2015 | Ferrell et al. |
| 2015/0136336 A1 | 5/2015 | Huang |
| 2015/0148774 A1 | 5/2015 | Yao |
| 2015/0157794 A1 | 6/2015 | Roy et al. |
| 2015/0164414 A1 | 6/2015 | Matthews |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217051 A1 | 8/2015 | Mastrototaro et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0265768 A1 | 9/2015 | Vazquez et al. |
| 2015/0301691 A1 | 10/2015 | Qin |
| 2015/0306314 A1 | 10/2015 | Doyle et al. |
| 2015/0314062 A1 | 11/2015 | Blomquist et al. |
| 2015/0320933 A1 | 11/2015 | Estes |
| 2015/0328402 A1 | 11/2015 | Nogueira et al. |
| 2015/0331995 A1 | 11/2015 | Zhao et al. |
| 2015/0351671 A1 | 12/2015 | Vanslyke et al. |
| 2015/0351672 A1 | 12/2015 | Vanslyke et al. |
| 2015/0351683 A1 | 12/2015 | Brauker et al. |
| 2015/0352282 A1 | 12/2015 | Mazlish |
| 2015/0352283 A1 | 12/2015 | Galasso |
| 2015/0356250 A1 | 12/2015 | Polimeni |
| 2015/0366945 A1 | 12/2015 | Greene |
| 2016/0000998 A1 | 1/2016 | Estes |
| 2016/0015891 A1 | 1/2016 | Papiorek |
| 2016/0019352 A1 | 1/2016 | Cohen et al. |
| 2016/0030669 A1 | 2/2016 | Harris et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0082188 A1 | 3/2016 | Blomquist et al. |
| 2016/0089494 A1 | 3/2016 | Guerrini |
| 2016/0158438 A1 | 6/2016 | Monirabbasi et al. |
| 2016/0162662 A1 | 6/2016 | Monirabbasi et al. |
| 2016/0175520 A1 | 6/2016 | Palerm et al. |
| 2016/0213841 A1 | 7/2016 | Geismar et al. |
| 2016/0220181 A1 | 8/2016 | Rigoard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0256629 A1 | 9/2016 | Grosman et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0007882 A1 | 1/2017 | Werner |
| 2017/0021096 A1 | 1/2017 | Cole et al. |
| 2017/0049386 A1 | 2/2017 | Abraham et al. |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0182248 A1 | 6/2017 | Rosinko |
| 2017/0188943 A1 | 7/2017 | Braig et al. |
| 2017/0189614 A1 | 7/2017 | Mazlish et al. |
| 2017/0189625 A1 | 7/2017 | Cirillo et al. |
| 2017/0203036 A1 | 7/2017 | Mazlish et al. |
| 2017/0216524 A1 | 8/2017 | Haider et al. |
| 2017/0239415 A1 | 8/2017 | Hwang et al. |
| 2017/0258987 A1 | 9/2017 | Caspers |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0347971 A1 | 12/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrsio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |
| 2022/0105270 A1 | 4/2022 | Doyle et al. |
| 2022/0126027 A1 | 4/2022 | Narayanaswami |

FOREIGN PATENT DOCUMENTS

| | | |
|---|---|---|
| CA | 1040271 A | 10/1978 |
| CA | 2543545 A1 | 5/2005 |
| CA | 3026851 A1 | 2/2020 |
| CN | 1297140 A | 5/2001 |
| CN | 1859943 A | 11/2006 |
| CN | 101208699 A | 6/2008 |
| DE | 4200595 A1 | 7/1993 |
| DE | 19627619 | 1/1998 |
| DE | 19756872 A1 | 7/1999 |
| DE | 19912459 A1 | 9/2000 |
| DE | 10236669 A1 | 2/2004 |
| DE | 202005012358 U1 | 10/2005 |
| DK | 200401893 | 12/2004 |
| EP | 0026056 A1 | 4/1981 |
| EP | 0062974 A1 | 10/1982 |
| EP | 0098592 A2 | 1/1984 |
| EP | 0275213 A2 | 7/1988 |
| EP | 0341049 A2 | 11/1989 |
| EP | 0496141 A1 | 7/1992 |
| EP | 0496305 A2 | 7/1992 |
| EP | 0549341 A1 | 6/1993 |
| EP | 0580723 A1 | 2/1994 |
| EP | 0612004 A1 | 8/1994 |
| EP | 0721358 A1 | 7/1996 |

(56) References Cited

FOREIGN PATENT DOCUMENTS

| | | |
|---|---|---|
| EP | 0867196 A2 | 9/1998 |
| EP | 0939451 A1 | 9/1999 |
| EP | 1045146 A2 | 10/2000 |
| EP | 1136698 A1 | 9/2001 |
| EP | 1376759 A2 | 1/2004 |
| EP | 1177802 B1 | 9/2004 |
| EP | 1491144 A1 | 12/2004 |
| EP | 1495775 A1 | 1/2005 |
| EP | 1527792 A1 | 5/2005 |
| EP | 1571582 A2 | 9/2005 |
| EP | 0801578 B1 | 7/2006 |
| EP | 1754498 A1 | 2/2007 |
| EP | 1818664 A1 | 8/2007 |
| EP | 1824536 A1 | 8/2007 |
| EP | 1951340 A1 | 8/2008 |
| EP | 2139382 A1 | 1/2010 |
| EP | 2397181 A1 | 12/2011 |
| EP | 2468338 A1 | 6/2012 |
| EP | 2666520 A1 | 11/2013 |
| EP | 2695573 A2 | 2/2014 |
| EP | 2703024 A1 | 3/2014 |
| EP | 2764881 A1 | 8/2014 |
| EP | 2830499 A1 | 2/2015 |
| EP | 2897071 A1 | 7/2015 |
| EP | 2943149 A1 | 11/2015 |
| EP | 3177344 A1 | 6/2017 |
| EP | 3193979 A1 | 7/2017 |
| EP | 3314548 A1 | 5/2018 |
| EP | 3607985 A1 | 2/2020 |
| FR | 2096275 A5 | 2/1972 |
| FR | 2585252 A1 | 1/1987 |
| GB | 0747701 | 4/1956 |
| GB | 1125897 A | 9/1968 |
| GB | 2218831 A | 11/1989 |
| GB | 2443261 A | 4/2008 |
| JP | 51-125993 A | 11/1976 |
| JP | 02-131777 A | 5/1990 |
| JP | 09-504974 A | 5/1997 |
| JP | 11-010036 A | 1/1999 |
| JP | 2000-513974 A | 10/2000 |
| JP | 2002-085556 A | 3/2002 |
| JP | 2002-507459 A | 3/2002 |
| JP | 2002-523149 A | 7/2002 |
| JP | 2003-531691 A | 10/2003 |
| JP | 2004-283378 A | 10/2004 |
| JP | 2005-326943 A | 11/2005 |
| JP | 2007-525276 A | 9/2007 |
| JP | 2008-513142 A | 5/2008 |
| JP | 2010-502361 A | 1/2010 |
| JP | 2010-524639 A | 7/2010 |
| JP | 2012-527981 A | 11/2012 |
| JP | 2017-516548 A | 6/2017 |
| JP | 2017-525451 A | 9/2017 |
| JP | 2018-153569 A | 10/2018 |
| JP | 2019-525276 A | 9/2019 |
| NO | 01/72360 A1 | 10/2001 |
| TW | 200740148 A | 10/2007 |
| TW | M452390 U | 5/2013 |
| WO | 86/06796 A1 | 11/1986 |
| WO | 90/15928 A1 | 12/1990 |
| WO | 97/21457 A1 | 6/1997 |
| WO | 98/00193 A1 | 1/1998 |
| WO | 98/04301 A1 | 2/1998 |
| WO | 98/11927 A1 | 3/1998 |
| WO | 98/55073 A1 | 12/1998 |
| WO | 98/57683 A1 | 12/1998 |
| WO | 99/07425 A1 | 2/1999 |
| WO | 99/10040 A1 | 3/1999 |
| WO | 99/10049 A1 | 3/1999 |
| WO | 99/21596 A1 | 5/1999 |
| WO | 99/39118 A1 | 8/1999 |
| WO | 99/48546 A1 | 9/1999 |
| WO | 99/56803 A1 | 11/1999 |
| WO | 99/62576 A1 | 12/1999 |
| WO | 00/30705 A1 | 6/2000 |
| WO | 00/32258 A1 | 6/2000 |
| WO | 00/48112 A2 | 8/2000 |
| WO | 01/54753 A2 | 8/2001 |
| WO | 01/72354 A2 | 10/2001 |
| WO | 01/78812 A1 | 10/2001 |
| WO | 01/91822 A1 | 12/2001 |
| WO | 01/91833 A1 | 12/2001 |
| WO | 02/15954 A1 | 2/2002 |
| WO | 02/26282 A2 | 4/2002 |
| WO | 02/40083 A2 | 5/2002 |
| WO | 02/43866 A2 | 6/2002 |
| WO | 02/57627 A1 | 7/2002 |
| WO | 02/68015 A2 | 9/2002 |
| WO | 02/76535 A1 | 10/2002 |
| WO | 02/81012 A2 | 10/2002 |
| WO | 02/82990 A1 | 10/2002 |
| WO | 02/84336 A2 | 10/2002 |
| WO | 2002/100469 A2 | 12/2002 |
| WO | 03/16882 A1 | 2/2003 |
| WO | 03/23728 A1 | 3/2003 |
| WO | 03/26728 A1 | 3/2003 |
| WO | 03/26726 A1 | 4/2003 |
| WO | 03/39362 A1 | 5/2003 |
| WO | 03/45233 A1 | 6/2003 |
| WO | 03/97133 A1 | 11/2003 |
| WO | 2003/103763 A1 | 12/2003 |
| WO | 2004/041330 A2 | 5/2004 |
| WO | 2004/043250 A1 | 5/2004 |
| WO | 2004/056412 A2 | 7/2004 |
| WO | 2004/092715 A1 | 10/2004 |
| WO | 2004/093648 A2 | 11/2004 |
| WO | 2004/110526 A1 | 12/2004 |
| WO | 2005/002652 A2 | 1/2005 |
| WO | 2005/011779 A1 | 2/2005 |
| WO | 2005/011799 A1 | 2/2005 |
| WO | 2005/039673 A2 | 5/2005 |
| WO | 2005/051170 A2 | 6/2005 |
| WO | 2005/072794 A2 | 8/2005 |
| WO | 2005/072795 A2 | 8/2005 |
| WO | 2005/082436 A1 | 9/2005 |
| WO | 2005/110601 A1 | 11/2005 |
| WO | 2005/113036 A1 | 12/2005 |
| WO | 2006/053007 A2 | 5/2006 |
| WO | 2006/061354 A1 | 6/2006 |
| WO | 2006/067217 A2 | 6/2006 |
| WO | 2006/075016 A1 | 7/2006 |
| WO | 2006/097453 A1 | 9/2006 |
| WO | 2006/105792 A1 | 10/2006 |
| WO | 2006/105793 A1 | 10/2006 |
| WO | 2006/105794 A1 | 10/2006 |
| WO | 2007/005219 A1 | 1/2007 |
| WO | 2007/056247 A2 | 5/2007 |
| WO | 2007/056504 A1 | 5/2007 |
| WO | 2007/056592 A2 | 5/2007 |
| WO | 2007/064835 A2 | 6/2007 |
| WO | 2007/066152 A2 | 6/2007 |
| WO | 2007/071255 A1 | 6/2007 |
| WO | 2007/078937 A2 | 7/2007 |
| WO | 2007/078992 A1 | 7/2007 |
| WO | 2007/141786 A1 | 12/2007 |
| WO | 2008/016621 A1 | 2/2008 |
| WO | 2008/024810 A2 | 2/2008 |
| WO | 2008/029403 A1 | 3/2008 |
| WO | 2008/073609 A2 | 6/2008 |
| WO | 2008/089184 A2 | 7/2008 |
| WO | 2008/103175 A1 | 8/2008 |
| WO | 2008/133702 A1 | 11/2008 |
| WO | 2008/134146 A1 | 11/2008 |
| WO | 2009/032402 A1 | 3/2009 |
| WO | 2009/035759 A1 | 3/2009 |
| WO | 2009/039203 A2 | 3/2009 |
| WO | 2009/045462 A1 | 4/2009 |
| WO | 2009/049252 A1 | 4/2009 |
| WO | 2009/066287 A2 | 5/2009 |
| WO | 2009/066288 A1 | 5/2009 |
| WO | 2009/098648 A2 | 8/2009 |
| WO | 2009/134380 A2 | 11/2009 |
| WO | 2010/022069 A2 | 2/2010 |
| WO | 2010/045460 A2 | 4/2010 |

(56) References Cited

FOREIGN PATENT DOCUMENTS

| | | |
|---|---|---|
| WO | 2010/053702 A1 | 5/2010 |
| WO | 2010/077279 A1 | 7/2010 |
| WO | 2010/097796 A1 | 9/2010 |
| WO | 2010/132077 A1 | 11/2010 |
| WO | 2010/138848 A1 | 12/2010 |
| WO | 2010/139793 A1 | 12/2010 |
| WO | 2010/147659 A2 | 12/2010 |
| WO | 2011/031458 A1 | 3/2011 |
| WO | 2011/075042 A1 | 6/2011 |
| WO | 2011/095483 A1 | 8/2011 |
| WO | 2011/133823 A1 | 10/2011 |
| WO | 2012/045667 A2 | 4/2012 |
| WO | 2012/073032 A1 | 6/2012 |
| WO | 2012/108959 A1 | 8/2012 |
| WO | 2012/134588 A1 | 10/2012 |
| WO | 2012/177353 A1 | 12/2012 |
| WO | 2012/178134 A1 | 12/2012 |
| WO | 2013/050535 A2 | 4/2013 |
| WO | 2013/078200 A1 | 5/2013 |
| WO | 2013/134486 A2 | 9/2013 |
| WO | 2013/149186 A1 | 10/2013 |
| WO | 2013/177565 A1 | 11/2013 |
| WO | 2013/182321 A1 | 12/2013 |
| WO | 2014/029416 A1 | 2/2014 |
| WO | 2014/035672 A2 | 3/2014 |
| WO | 2014/062399 A1 | 4/2014 |
| WO | 2014/074476 A1 | 5/2014 |
| WO | 2014/109898 A1 | 7/2014 |
| WO | 2014/110538 A1 | 7/2014 |
| WO | 2014/134459 A1 | 9/2014 |
| WO | 2014/149357 A1 | 9/2014 |
| WO | 2014/172467 A1 | 10/2014 |
| WO | 2014/179774 A1 | 11/2014 |
| WO | 2014/194183 A2 | 12/2014 |
| WO | 2015/056259 A1 | 4/2015 |
| WO | 2015/061493 A1 | 4/2015 |
| WO | 2015/073211 A1 | 5/2015 |
| WO | 2015/081337 A2 | 6/2015 |
| WO | 2015/117082 A1 | 8/2015 |
| WO | 2015/117854 A1 | 8/2015 |
| WO | 2015/167201 A1 | 11/2015 |
| WO | 2015/177082 A1 | 11/2015 |
| WO | 2015/187366 A1 | 12/2015 |
| WO | 2015/191459 A1 | 12/2015 |
| WO | 2016/004088 A1 | 1/2016 |
| WO | 2016/004210 A1 | 1/2016 |
| WO | 2016/022650 A1 | 2/2016 |
| WO | 2016/041873 A1 | 3/2016 |
| WO | 2016/089702 A1 | 6/2016 |
| WO | 2016/141082 A1 | 9/2016 |
| WO | 2016/161254 A1 | 10/2016 |
| WO | 2017/004278 A1 | 1/2017 |
| WO | 2017/091624 A1 | 6/2017 |
| WO | 2017/105600 A1 | 6/2017 |
| WO | 2017/184988 A1 | 10/2017 |
| WO | 2017/187177 A1 | 11/2017 |
| WO | 2017/205816 A1 | 11/2017 |
| WO | 2018/009614 A1 | 1/2018 |
| WO | 2018/067748 A1 | 4/2018 |
| WO | 2018/120104 A1 | 7/2018 |
| WO | 2018/136799 A1 | 7/2018 |
| WO | 2018/204568 A1 | 11/2018 |
| WO | 2019/077482 A1 | 4/2019 |
| WO | 2019/094440 A1 | 5/2019 |
| WO | 2019/213493 A1 | 11/2019 |
| WO | 2019/246381 A1 | 12/2019 |
| WO | 2020/081393 A1 | 4/2020 |
| WO | 2021/011738 A1 | 1/2021 |

OTHER PUBLICATIONS

"Minimed Inc. Introduces 407C Infusion Pump for General Medication Use" [online]. Business Wire, AllBusiness.com, Aug. 10, 1999 [retrieved on Feb. 28, 2011]. Retrieved from the Internet: <URL: http://www.allbusiness.com/company-activities-management/product-management/6734565-1.html>.

"Using the Deltec Cozmo Insulin Pump Correction Bolus Feature" believed to be publicly available before May 5, 2008, pp. 36-41.

Accu-Chek Spirit, "Pump Therapy Made for You," Roche, 2006, 6 pages.

Animas Corporation, IR1200 User Guide Manual, pp. 29-31, revised Sep. 2006.

Asante Pearl, Insulin Pump User Manual, 2012, 180 pages.

Brown et al., "CGM, Pumps, and SMBG." American Diabetes Association—71st Scientific Sessions, San Diego, CA, Jun. 24-28, 2011, 38 pages.

Collins and Lee, "Microfluidic flow transducer based on the measurement of electrical admittance," Lab Chip, 2003, 12 pages.

Copp et al., "Simultaneous Model Predictive Control and Moving Horizon Estimation for Blood Glucose Regulation in Type 1 Diabetes," Optim. Control Appl. Meth. 2016, 15 pages.

Cox et al. "Prediction of Severe Hypoglycemia." Diabetes Care, vol. 30, No. 6, Jun. 2007, 4 pages.

Dassau et al., "12-Week 24/7 Ambulatory Artificial Pancreas With Weekly Adaptation of Insulin Delivery Settings: Effect on Hemoglobin A1c and Hypoglycemia" Diabetes Care, Dec. 1, 2017, 40(12):1719-26.

Debiotech News Release, "Debiotech reveals its new miniaturized Disposable Insulin Nanopump.TM. for Diabetes therapy," available at http://www.debiotech.com/news/nw.sub.—159.html Apr. 24, 2006, 3 pages.

DOCNEWS; The latest in high-tech and convenient devices; American Diabetes Assoc.; 2(7); retrieved from the internet: (http://web.archive.org/web/20080526162751/http://docnews.diabetesjournals.org/cgi/content/full/Feb. 7, 2013?); 3 pgs.; Jul. 1, 2005.

Duden Deutsches Universaiworterbuch, Dudenveriag, Mannheim, 1989, p. 822.

Dumont, "Feedback control for clinicians," Journal of clinical monitoring and computing, Feb. 1, 2014, 28(1):5-11.

Fischer et al., "In Vivo Comparison of Different Algorithms for the Artificial Beta-Cell," Artificial organs, May 1, 1985, 9(2):173-9.

Guarnieri et al.; Flexible versus rigid catheters for chronic administration of exogenous agents into central nervous system tissues (abstract only); J Neurosc Meth; 144(2); pp. 147-152; Jun. 2005.

Insulet Corporation; Innovative New System for Managing Diabetes Receives FDA Clearance; The OmniPod (Registered) Insulin Management System (press release); retrieved from the internet: (http://phx.corporate-ir.net/phoenix.zhtml?c=209336&p=irol-newsArticle_pf&ID=988708&highlight=); 2 pgs.; Feb. 1, 2005.

Insulet Corporation; OmniPod (Registered) Insulin Management System (quick-start guide); 2 pgs.; (Copyright) 2008.

International Search Report and Written Opinion in International Application No. PCT/US2014/047023, mailed on Nov. 28, 2014, 19 pages.

Keith Hynes et al., "DiAs User Interface: A Patient-Centric Interface for Mobile Artificial Pancreas Systems," J Diabetes Sci Tech 7(6):1416-1426, Nov. 2013.

OmniPod Quick Start Guide, 2007, 2 pages.

Oxford Advanced Learners Dictionary, 4th Ed., Oxford University Press, Oxford, 1989, p. 178.

Patent Abstracts of Japan, vol. 1999, No. 04, and JP 11 010036, Apr. 30, 1999 and Jan. 19, 1999, Toray Ind. Inc., 6 pages.

Percival et al., "Closed-Loop Control and Advisory Mode Evaluation of an Artificial Pancreatic Beta Cell: Use of Proportional-Integral-Derivative Equivalent Model-Based Controllers," J Diabetes Sci Tech 2(4):636-644, Jul. 2008.

Salzsieder et al., "Estimation of individually adapted control parameters for an artificial beta cell," Biomed. Biochim. Acta, Jan. 1, 1984, 43(5):585-596.

Shiavon et al., "Quantitative Estimation of Insulin Sensitivity in Type 1 Diabetic Subjects Wearing a Sensor-Augmented Insulin Pump," Diabetes care, May 1, 2014, 37(5):1216-23.

Supplemental European Search Report in Application No. EP 14826694, dated Jul. 1, 2016, 7 pages.

(56) References Cited

OTHER PUBLICATIONS

The Content of Investigational Device Exemption (IDE) and Premarket Approval (PMA) Application for Low Glucose Suspend (LGS) Device System. Rockville, MD, Food and Drug Administration, 2011, 59 pages.
The Medtronic Diabetes Connection, 2006, 6 pages.
U.S. Appl. filed Dec. 23, 2005., U.S. Appl. No. 60/753,984.
U.S. Patent Application filed Nov. 8, 2005., U.S. Appl. No. 60/734,382.
U.S. Provisional Application filed Dec. 23, 2005., U.S. Appl. No. 60/753,684.
Walsh et al., "Guidelines for Insulin Dosing in Continuous Subcutaneious Insulin Infusion Using New Formulas from a Retrospective Study of Individuals with Optimal Glucose Levels", J. Diabetes Science and Technology, Sep. 2010, 4(5):8 pages.
Walsh et al., "Guidelines for Optimal Bolus Calculator Settings in Adults", J. Diabetes Science and Technology, Jan. 2011, 5(1):7 pages.
Xilas Temp Touch, "The latest in high-tech and convenient devices," DOCNews, vol. 2, No. 7, Jul. 1, 2005, http://docnews.diabetesioumals.ord/cgi/content/full/2/7/13, 3 pages.
Abstract of M. Guamieri et al., Flexible versus rigid catheters for chronic administration of exogenous agents into central nervous system tissues, J. Neurosc. Meth, 144, 147-152, Jun. 15, 2005.
Asante Solutions Pearl User Manual, Asante Inc., 2012, 180 pages.
Australian Examination Report for Application No. 2021204821 dated Jul. 6, 2022, 4 pages.
Collins and Lee, "Microfluidic flow transducer based on the measurement of electrical admittance," Lab Chip, 2004, 4:7-10.
Collins et al., Microfluidic flow transducer based on the measurement of electrical admittance. Lab on a Chip, (2004), 4(1), 7, 4 pages, doi:10.1039/b310282c.
Dassau et al., 12-Week 24/7 Ambulatory Artificial Pancreas With Weekly Adaptation of Insulin Delivery Settings: Effect on Hemoglobin A1c and Hypoglycemia, Diabetes Care, Oct. 13, 2017, 40(12):1719-26.
Debiotech News Release, "Debiotech reveals its new iniaturized disposable insulin Nanopump (Trademark) for diabetes therapy," available at URL <http://www.debiotech.com/news/nw_159.html>, Apr. 24, 2006, 3 pages.
Debiotech News Release, "Debiotech reveals its new miniaturized Disposable Insulin Nanopump (Trademark) for Diabetes therapy," available at http://www.debiotech.com/news/nw 159.html Apr. 24, 2006, 3 pages.
Debiotech SA; Debiotech reveals its new miniaturized Disposable Insulin Nanopump} for Diabetes therapy (news release); retrieved from the internet: (http://web.archive.org/web/20060822033820/http://www.debiotech.com/news/nw_159.html); 3 pgs.; Apr. 24, 2006.
Decision to grant received for European Patent Application No. 14826694.3, mailed on Apr. 4, 2019, 2 pages.
DOCNEWS; The latest in high-tech and convenient devices; American Diabetes Assoc.; 2(7); retrieved from the internet: (http://web.archive.Org/web/20080526162751/http://docnews.diabetesjoumals.org/cgi/content/full/Feb. 7, 13?); 3 pgs.; Jul. 1, 2005.
European Communication pursuant to Article 94(3) EPC for European Application No. 14826694.3, dated Oct. 12, 2017, 4 pages.
European Examination Report from European Application No. 17701779.5, dated Sep. 30, 2021, 8 pages.
Honan, Matthew. "Apple unveils iPhone" Jan. 9, 2007. MacCentral. Accessed Dec. 29, 2011. 2 pages.
Hornby et al.; Catheter (definition); Oxford Advanced Learners Dictionary, 4th Ed.; Oxford University Press; Oxford, UK; p. 178; Apr. 1989.
Intention to grant received for European Patent Application No. 14826694.3, mailed on Mar. 20, 2019, 4 pages.
Intention to grant received for European Patent Application No. 14826694.3, mailed on Oct. 2, 2018, 6 pages.
Kovatchev et al., "Safety of Outpatient Closed-Loop Control: First Randomized Crossover Trials of a Wearable Artificial Pancreas," Diabetes Care 37(7):1789-1796, Jul. 2014.
Medtronic News Release, "Medtronic Receives FDA Approval for World's First Insulin Pump with Real-time Continuous Glucose Monitoring," Apr. 13, 2006, 3 pages.
OmniPod Insulin Management System-Investor Relations—Press Release, Feb. 1, 2005, http://investors.insulet.com/phoenix.zhtml?c=209336&p=irol-newsArticle&ID=988708&highlight= 1 page.
OmniPod Insulin Management System-Investor Relations—Press Release, Feb. 1, 2005, http://investors.insulet.com/phoenix.zhtml?c=209336&p=irol-newsA- rdele&ID=988708&highlight= 1 page.
Patent Abstracts of Japan, vol. 1999, No. 04, and JP 11 010036, Apr. 30, 1999 and Jan. 19, 1999, Toray Ind. Inc.
Patent Abstracts of Japan, vol. 1999, No. 4, and JP 11 010036 , Apr. 30, 1999 and Jan. 19, 1999, Toray Ind. Inc.
Percival et al., "Closed-Loop Control and Advisory Mode Evaluation of an Ar Uncial Pancreatic Beta Cell: Use Of Proportional-Integral-Derivative Equivalent Model-Based Controllers," J Diabetes Sci Tech 2(4):636-644, Jul. 2008.
Supplementary European Extended Search Report and Opinion for European Application No. 14826694.3., dated Jul. 1, 2016, 7 pages.
U.S. Appl. filed Nov. 8, 2005, Mernoe, et al., U.S. Appl. No. 60/734,382.
U.S. Appl. No. 11/362,616.
Vozeh et al., "Feedback Control Methods for Drug Dosage Optimisation, Concepts, Classifications and Clinical Application," Clinical pharmacokinetics, Nov. 1, 1985, 10(6):457-76.
Walsh et al., "Guidelines for Insulin Dosing in Continuous Subcutaneous Insulin Infusion Using New Formulas from a Retrospective Study of Individuals with Optimal Glucose Levels", J. Diabetes Science and Technology, vol. 4 Issue 5, Sep. 2010 (8 pages).
Walsh et al., "Guidelines for Optimal Bolus Calculator Settings in Adults", J. Diabetes Science and Technology; vol. 5 Issue 1; Jan. 2011 (7 pages).
Which Insulin Pump is Right for Me?, Albany Medical Center, Goodman Diabetes Service, Jan. 2006, 4 pages.
Xilas Temp Touch, "The latest in high-tech and convenient devices," DOCNews, vol. 2, No. 7, Jul. 1, 2005, http;//docnews.diabetesjournals.ord/cgi/content/full/2/7/13, 3 pages.
International Search Report from International Application No. PCT/US06/43599, mailed Mar. 20, 2007, 4 pages.
International Written Opinion from International Application No. PCT/US06/43599, mailed Mar. 20, 2007, 6 pages.
Examination report No. 1 of Australian Application No. 2023203536, mailed Mar. 8, 2024, 3 pages.
First Office Action and Search Report of Chinese Patent Application No. 202111284422.2, issued Apr. 25, 2024, 16 pages with English translation.

* cited by examiner

INFUSION PUMP SYSTEM AND METHOD

CROSS-REFERENCE TO RELATED APPLICATIONS

This application is a continuation of U.S. patent application Ser. No. 15/893,145, filed Feb. 9, 2018, now U.S. Pat. No. 11,147,914, issued Oct. 19, 2021, which is a divisional of Ser. No. 15/383,176, filed on Dec. 19, 2016, now U.S. Pat. No. 10,207,047, issued on Feb. 19, 2019, which is a continuation application of and claims priority to U.S. application Ser. No. 13/946,330, filed on Jul. 19, 2013, now U.S. Pat. No. 9,561,324, issued on Feb. 7, 2017, the disclosure of each of which is hereby incorporated herein in its entirety by this reference.

TECHNICAL FIELD

This document relates to an infusion pump system, such as a portable infusion pump system for dispensing a medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Users of infusion pump devices often need to communicate with the infusion pump via a user interface to control the operations of the infusion pump in a safe and effective manner. For example, a user may press a series of buttons on the user interface to enter food intake data into the infusion pump, such as a number of grams of carbohydrates that is indicative of a recently or soon-to-be consumed meal. The food intake data can be combined by the infusion pump system with other parameters to calculate a suggested bolus dosage of insulin based on the grams of carbohydrates entered by the user. In another example, a user may enter information into the infusion pump system via a user interface that indicates that the user is going to perform a level of physical exercise. In some circumstances, the infusion pump system may reduce the amount of a planned dispensation of insulin in response to the exercise information entered by the user.

SUMMARY

Some embodiments of an infusion pump system may be configured to send and receive data communications using near field communication ("NFC") technology. By incorporating NFC technology within the infusion pump system, user communications with the pump system can be enhanced and simplified. For example, NFC can facilitate the convenient sharing of user commands or other data to an infusion pump system a NFC that is equipped with NFC functionality. In some embodiments, pre-programmed NFC communicator devices ("NFC tags") can be used to transfer data from the NFC tag to the infusion pump system via a simple hand motion or the like by the user of the infusion pump system. The data that is transferred may cause the infusion pump system to execute particular operations as defined by the data or in correspondence to the data. For example, a NFC tag can be configured to communicate a set of user input commands to an infusion pump system (e.g., user input commands that might otherwise be input via a series of menu selections and data entry steps on the user interface of the pump system) so as to rapidly indicate to the pump system that particular amount of food or carbohydrates will be consumed for a meal. In some embodiments, data can be written from the infusion pump system to a NFC tag. For example, a back-up copy of user settings that are used to configure an infusion pump system for a particular user may be downloaded using NFC from the infusion pump system and saved onto a NFC tag. In particular embodiments, the infusion pump system can be equipped with one or more accelerometers that can be used to activate the potential for NFC communications to take place when an acceleration at or above the threshold level is detected.

In particular embodiments, a medical infusion pump system may include a portable pump housing that defines a space to receive a medicine. The infusion pump system may include a pump drive system to dispense medicine from the portable housing when the medicine is received in the space. The infusion pump system may further include control circuitry that communicates control signals to the pump drive system to control dispensation of the medicine from the portable housing when the medicine is received in the space. Optionally, the infusion pump system may also include a near field communication (NFC) circuit electrically connected with the control circuitry to communicate infusion pump task data to the control circuitry. The NFC circuit can be configured to wirelessly receive the infusion pump task data from a NFC communicator device when the NFC circuit and NFC communicator device are positioned within a NFC proximity range.

In some implementations, the system may optionally include the NFC communicator device that is separate from the pump housing. For example, the NFC communicator device can be a near field communication tag storing the infusion pump task data. The infusion pump task data may comprise a unique identifier that identifies the near field communication tag, and in response to receiving the unique identifier, the control circuitry may execute user interface operations that correspond to the unique identifier. Optionally, the user interface operations may comprise user interface settings for calculating a suggested bolus dispensation of the medicine. In another option, the infusion pump system may further include an accelerometer electrically connected to the control circuitry, wherein the accelerometer may be configured to detect acceleration movement of the portable housing and to communicate the detected movement to the control circuitry. In a further option, the control circuitry is configured to compare a characteristic value of the detected movement to a threshold movement value. The control circuitry may be configured to activate near field communication with the NFC communicator device based on the comparison of the characteristic value to the threshold movement value. Optionally, the control circuitry may be housed in a controller housing that is removably attachable to the portable housing.

In some implementations described herein, the system may optionally include a remote-control device that is separate from the pump housing. The remote-control device can be configured to wirelessly communicate with a wireless communication device connected to the control circuitry (for example, a wireless communication device that is different from the aforementioned NFC circuit). Optionally, the remote-control device may further include a second NFC circuit that is configured to wirelessly receive the infusion pump task data from the NFC communicator device when the second NFC circuit and NFC communicator device are positioned within the NFC proximity range. In some cases, the NFC proximity range has a maximum working distance of less than 12 inches. The infusion pump task data may be indicative of a value of carbohydrates of a food item.

In particular embodiments, a medical infusion pump system may include a pump device and a controller device. The pump device may include a pump housing that defines a space to receive a medicine, and a drive system positioned in the pump housing to dispense the medicine from the pump device when the medicine is received in the space of the pump housing. Optionally, the controller device may be removably attachable to the pump device. For example, the controller device may be removably attachable to the pump housing so as to electrically connect with the pump device. The controller device may house control circuitry configured to communicate control signals to the drive system positioned in the pump housing to control dispensation of the medicine from the pump device. The controller device may also house a NFC circuit electrically connected with the control circuitry to communicate infusion pump task data to the control circuitry. Optionally, the NFC circuit is configured to wirelessly receive the infusion pump task data from a NFC communicator device when the NFC circuit and NFC communicator device are positioned within a NFC proximity range.

In some implementations, the system may further comprise the NFC communicator device that is separate from the pump device and the controller device. For example, the NFC communicator device may be a near field communication tag storing the infusion pump task data. Optionally, the infusion pump task data may comprise a unique identifier that identifies the near field communication tag, and in response to receiving the unique identifier, the control circuitry may execute user interface operations that correspond to the unique identifier. In one example, the user interface operations may comprise user interface settings for calculating a bolus dispensation of the medicine. Optionally, the system may further include at least one accelerometer electrically connected to the control circuitry. The accelerometer may be configured to detect acceleration movement of the portable pump housing and to communicate the detected movement to the control circuitry. The control circuitry may be configured to compare a characteristic value of the detected movement to a threshold movement value. The control circuitry may be configured to activate near field communication with the NFC communicator device based on the comparison of the characteristic value to the threshold movement value.

In various implementations of the system, the pump device may optionally be a one-time-use device equipped with one or more structures configured to prevent reuse of the pump device. Also, in some implementations, the controller device may optionally be a reusable controller device. For example, the controller device may include one or more of: a controller housing that is removably attachable to the pump housing in a fixed relationship; one or more electrical contacts disposed on the controller housing, the electrical contacts of the controller device being engageable with corresponding electrical contacts of the pump device when removably attached.

Additionally, particular embodiments described herein may include a method of controlling a portable infusion pump system. The method may include receiving input via near field communication (NFC) from a NFC tag storing data indicative of a task associated with using the portable infusion pump system. The method may optionally include controlling the portable infusion pump system to change an operation of the portable infusion pump system in based upon the data the input from the NFC tag. In some implementations, the method may further comprise prompting a user via a user interface display to confirm the operation change of the portable infusion pump system in response to receiving the input from the NFC tag. For example, the operation change to be confirmed via the user interface may include calculating or initiating a bolus dispensation of a medicine from the portable infusion pump system.

Some or all of the embodiments described herein may provide one or more of the following advantages. First, some embodiments of the infusion pump system may be configured to send and receive data communications using NFC technology. Second, some embodiments of an infusion pump system equipped with NFC technology may facilitate convenient user input of information to the infusion pump system. Third, the safety and efficacy of an infusion pump system may be enhanced because the rapid manner of inputting data to the infusion pump using NFC may facilitate more timely and complete data entry by the user. Fourth, in some circumstances, some users who may not be mentally or physically able to reliably operate a conventional user interface of an infusion pump system may be able to reliably input data to an infusion pump system using NFC communication interface. Fifth, the infusion pump system equipped with NFC equipment may be configured to be portable, wearable, and (in some circumstances) concealable. For example, a user can conveniently wear the infusion pump system on the user's skin under clothing or can carry the pump system in the user's pocket (or other portable location) while receiving the medicine dispensed from the pump device.

It should be understood from the description herein that the term "NFC" (as used herein) or "NFC" capability (as used herein) is different from traditional radio frequency identification ("RFID"). For example, NFC is a more specific version of wireless communication that can be configured for one-way or two-way communications and that operates at a maximum range of less than about 12 inches, about 8 inches or less, and preferably about 4 inches or less (e.g., unlike the much greater communication range of the traditional RFID technology that extends for many feet or more).

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference symbols in the various drawings indicate like elements.

DETAILED DESCRIPTION

Figure 1:
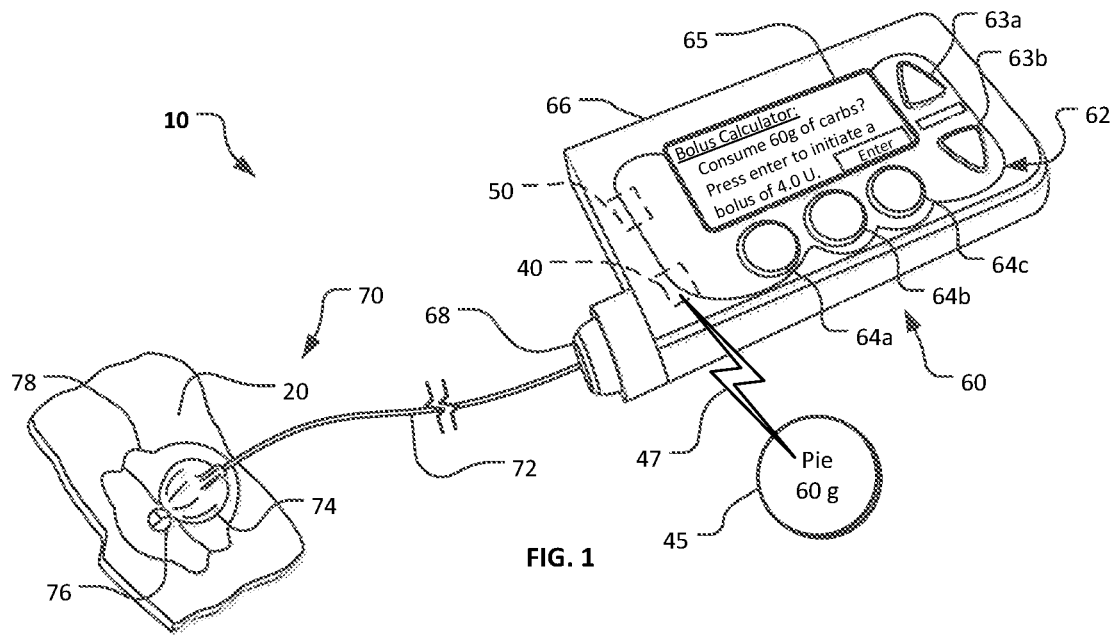
FIG. 1 is a perspective view of an infusion pump system with NFC capabilities in accordance with some embodiments.

Referring to FIG. 1, an infusion pump system 10 can include a portable pump 60 used to supply insulin or another medication to a user via, for example, an infusion set 70 (also referred to herein as infusion pump system 70). In some embodiments, the portable pump 60 includes a user interface 62 comprised of input devices such as buttons 63a, 63b, 64a, 64b, 64c and output devices such as display 65. At least a portion of the user interface 62 is coupled to a pump housing structure 66 of the portable pump 60, which houses the control circuitry for the portable pump 60. In particular embodiments, the portable pump 60 may further include a NFC circuit 40 that facilitates short-range wireless communications between the internal control circuitry of the portable pump 60 and an external device such as a NFC tag 45.

NFC can be used, for example, to rapidly input user commands or other data into the portable pump 60, thereby at least partially reducing the need to actuate the buttons 63a-63b, 64a-64c or other components of the user interface 62. As explained further herein, the data input to the portable pump 60 via NFC may cause the portable pump 60 to execute particular actions, such as automatically calculating an amount of a recommended bolus delivery of insulin (or another medication) and prompting the user with an option to confirm and initiate such a bolus delivery. By incorporating NFC equipment within the infusion pump system 10, user communications with the portable pump 60 can be enhanced and simplified. As a result, the accuracy and completeness of the data entered by the user into the portable pump 60 can be improved, and the user can experience greater convenience and time efficiency. Optionally, the portable pump 60 can further include an accelerometer 50 arranged in the pump housing structure 66. In some embodiments, the accelerometer 50 can be used to activate the NFC communications when an acceleration at or above the threshold level is detected, as explained further below.

The infusion pump system 10 is configured to controllably dispense a medicine to be infused into the tissue or vasculature of a targeted individual, such as a human or animal patient. In some embodiments, the portable pump 60 includes the pump housing structure 66 that defines a cavity in which a fluid cartridge (not shown) can be received. For example, the fluid cartridge can be a carpule that is either user-fillable or is preloaded with insulin or another medicine for use in the treatment of Diabetes (e.g., BYETTA®, SYMLIN®, or others). Such a cartridge may be supplied, for example, by Eli Lilly and Co. of Indianapolis, IN. Other examples of medicines that can be contained in the fluid cartridge include: pain relief drugs, hormone therapy, blood pressure treatments, anti-emetics, osteoporosis treatments, or other injectable medicines. The fluid cartridge may have other configurations. For example, in some embodiments the fluid cartridge may comprise a reservoir that is integral with the pump housing structure 66 (e.g., the fluid cartridge can be defined by one or more walls of the pump housing structure 66 that surround a plunger to define a reservoir in which the medicine is injected or otherwise received).

The portable pump 60 includes a cap device 68 to retain the fluid cartridge in the cavity of the pump housing structure 66 and, optionally, to penetrate a septum of the fluid cartridge for purposes of establishing fluid communication with the infusion set 70. The portable pump 60 includes a drive system (one example is described in more detail below in connection with FIG. 5) that advances a plunger in the fluid cartridge so as to dispense fluid therefrom. In some embodiments, the dispensed fluid exits the fluid cartridge, passes through a flexible tube 72 of the infusion set 70 to a cannula housing 74 retained to the user's skin 20 by a skin adhesive patch 78. The dispensed fluid can enter through the skin 20 via a cannula 76 attached to the underside of the cannula housing 74.

In some embodiments, the infusion pump system 10 can be configured to supply scheduled basal dosages of insulin (or another medication) along with user-selected bolus dosages. The basal delivery rate can be selected to maintain a user's blood glucose level in a targeted range during normal activity when the user is not consuming food items. The user-selected bolus deliveries may provide substantially larger amounts of insulin in particular circumstances in which the user's blood glucose level requires a significant correction. In some embodiments, the infusion pump system 10 can suggest a bolus dosage to the user in a manner that accounts for the user's food intake, the user's recent blood glucose level (e.g., input into the portable pump 60 by the user, from an integral blood test strip analyzer, transmitted to the portable pump 60 from an external blood glucose monitoring device, or the like), the rate of change in the user's blood glucose level, and previously delivered insulin that has not acted on the user. For example, a user can enter a carbohydrate value indicative of a meal into the portable pump 60, and in response thereto, the portable pump 60 can output a suggested bolus dosage to the user.

In some embodiments, the infusion pump system 10 may modify a bolus delivery (e.g., a bolus delivery after the user consumes a meal) in response to certain circumstances. For example, the infusion pump system 10 may decrease or otherwise modify a post-meal bolus delivery based on a rapidly falling blood glucose level, a current blood glucose level that is below a threshold limit, based on an increased level of physical activity, or the like.

The infusion pump system 10 can be configured to be portable and can be wearable and concealable. For example, a user can conveniently wear the infusion pump system 10 on the user's skin (e.g., using skin adhesive) underneath the user's clothing or carry the portable pump 60 in the user's pocket (or other portable location) while receiving the medicine dispensed from the infusion pump system 10. As such, the infusion pump system 10 can be used to deliver medicine to the tissues or vasculature of the user in a portable, concealable, and discrete manner.

Still referring to FIG. 1, the portable pump 60 includes the user interface 62 that permits a user to monitor and control the operation of the infusion pump system 10. In some embodiments, the user interface 62 includes a display 65 and the user-selectable buttons (e.g., five buttons 63a, 63b, 64a, 64b, and 64c in this embodiment) that are in electrical communication with the control circuitry of the portable pump 60. For example, the display 65 may be used to communicate a number of status indicators, alarms, settings, and/or menu options for the infusion pump system 10. In some embodiments, the user may press one or more of the buttons 63a, 63b, 64a, 64b, and 64c to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge, or the like).

In some embodiments, the user can adjust the settings or otherwise program the portable pump 60 by pressing one or more buttons 63a, 63b, 64a, 64b, and 64c of the user interface 62. For example, in embodiments of the infusion pump system 10 configured to dispense insulin, the user may press one or more of the buttons 63a, 63b, 64a, 64b, and 64c to change the dispensation rate of insulin or to request that a bolus of insulin be dispensed immediately, at a scheduled later time, over a period of time, or following a particular time-based profile. In another example, the user may use the buttons 63a, 63b, 64a, 64b, and 64c to manually input information such as the user's current blood glucose level (e.g., as measured by an external blood glucose meter), the current rate of change in the user's blood glucose level, or the like into the portable pump 60.

In some embodiments, the NFC circuit 40 is housed in the portable pump 60 to provide an additional functionality that can enhance and simplify user interactions with the portable pump 60. For instance, using NFC, the need for user activation of multiple buttons 63a, 63b, 64a, 64b, and 64c for shuffling through menus may be eliminated or otherwise reduced in some circumstances. In one example depicted in FIG. 1, the user of infusion pump system 10 has consumed, or will soon consume, a piece of pie that is estimated to include about 60 grams of carbohydrates. As such, the user desires to initiate a corresponding bolus dispensation of insulin to counteract the effects of the intake of 60 grams of carbohydrates. The bolus dispensation of insulin may be intended to cause the user's blood glucose level to remain within a target range.

To initiate the desired bolus dispensation, the user can first position the portable pump 60 containing the NFC circuit 40 in close proximity with the NFC tag 45 (e.g., preferably within a range 4 inches or less, including for example, a physical "bump" with the NFC tag 45). Wireless near field communications can thereby be established between the NFC circuit 40 and the NFC tag 45 (as signified by wireless communication symbol 47). In some embodiments, the user is provided with a notification that near field communications have been established. The notification can be visual, audible, tactile (vibratory), or a combination thereof. In response to the communication between the NFC tag 45 and the portable pump 60, the portable pump 60 provides a prompt to the user on the display 65. The prompt on the display 65 requests the user to confirm that the user desires to receive a 4.0-unit dispensation of insulin related to the intake of 60 grams of carbohydrates. To confirm and initiate the dispensation of the suggested bolus amount, the user can simply press button 64c to select "Enter." By this example, it can be appreciated that the incorporation of NFC equipment in the infusion pump system 10 can enhance and simplify user interactions with the infusion pump system 10, because in order to initiate appropriate suggested bolus dosage of insulin, the user simply bumped the NFC tag 45 with the pump housing structure 66 and then pressed a single acknowledgement button in response to the prompt on the display 65. As will be described further, in some embodiments, other techniques for user confirmation or acknowledgement can be used, and in some instances user confirmation or acknowledgement may be optional.

NFC provides short-range wireless communication. As described herein, the maximum working distance for NFC is less than 12 inches, about 8 inches or less, and about 4 inches or less in the aforementioned embodiment depicted in FIG. 1. NFC allows sharing of relatively small packets of data between a NFC tag and a device equipped with NFC functionality. In the embodiment depicted in FIG. 1, each NFC tag can store about a kilobyte of data or less, although NFC tags that store a greater quantity of data can also be used in the embodiments described herein. The NFC tags can be configured with a shape that is small and lightweight (e.g., a maximum dimension of about 1 inch or less), particular because the NFC tags described the embodiment of FIG. 1 do not have an integral power source such as a battery. Instead, a coil in the NFC tag inductively receives magnetic field energy that is emitted from a coil in NFC circuit housed in the portable infusion pump housing structure 66. Accordingly, energy and data can be wirelessly transmitted between the coils of the NCF tag and the device with NFC functionality. The wireless NFC data transmission can be a two-way wireless communication. That is, data can be transmitted from the NFC tag to the NFC circuit of the portable pump 60, and data can be transmitted to the NFC tag from the NFC circuit of the portable pump 60. In other words, the NFC circuit of the portable pump 60 can both read from and write to a NFC tag. The data stored in the NFC tag can be written in a variety of formats. One example format is called the NFC Data Exchange Format ("NDEF").

Referring again to FIG. 1, when the NFC tag 45 communicates with the NFC circuit 40, the resulting data exchange can trigger one or more automated actions by control circuitry housed in the portable pump 60. The particular actions are at least in part defined by particular computer program script that is initiated in response to the communications between the NFC tag 45 and NFC circuit 40. In some arrangements, the particular computer program script is stored on the NFC tag. In such arrangements, when the communications between the NFC tag 45 and NFC circuit 40 are established, the particular computer program script is transferred from the NFC tag 45 to the control circuitry of the portable pump 60 via the NFC circuit 40. The control circuitry then executes the particular computer program script and can cause the portable pump 60 to automatically perform an action or actions in accordance with the script.

In alternative arrangements, the particular computer program script to be executed in correspondence to the NFC tag 45 can be stored within the internal control circuitry of the portable pump 60. In such arrangements, the NFC tag 45 can transfer a unique identifier such as a serial number to the NFC circuit 40. Upon receipt of the unique identifier, the portable pump 60 can execute the particular computer program script that corresponds to the identifier. In some embodiments, a combination of both arrangements can be used. In any case, from the description herein it can be appreciated that a particular NCF tag (e.g., NFC tag 45) can be used to automatically trigger a corresponding particular action or change in operation of the portable pump 60. As such, a variety of NFC tags can be conveniently used with an infusion pump system 10 so as to enhance and simplify user interactions with the infusion pump system 10 in regard to a variety of scenarios and user desires.

In some embodiments, an accelerometer 50 can be optionally positioned in the portable pump 60 and connected to the control circuitry inside the pump housing structure 66. In particular embodiments, more than one accelerometer 50 can be included in the housing structure 66. The accelerometer 50 can operate in conjunction with control circuitry and the NFC circuit 40 to supplement the criteria for activating communications between the NFC circuit 40 and the NFC tag 45. In other words, while in some embodiments, communications between the NFC circuit 40 and the NFC tag 45 are activated based merely on the proximity therebetween, in other embodiments a threshold movement of the pump housing structure 66 (as detected by the accelerometer 50) is used (at least as a factor) in activating the NFC circuit 40 for communication with the nearby NFC tag 45. For example, in some embodiments the accelerometer 50 can serve to require that the user "bump" or otherwise tap the portable pump 60 onto the NFC tag 45 or another object before the NFC circuit 40 is activated. An objective for including this feature can be to more clearly ascertain that the user desires to activate NFC when the NFC tag 45 is within the required proximity with the NFC circuit 40. That is, by requiring the user to tap the portable pump 60 onto the NFC tag 45, the user's intentions for activating NFC can be confirmed with a greater level of confidence.

In some embodiments, this optional feature of using the accelerometer 50 in conjunction with the NFC circuit 40 can function as follows. When a movement is detected by accelerometer 50, the characteristics of the movement can be compared by the control circuitry to a predetermined threshold value (e.g., a threshold movement indicative of the aforementioned "bump" or tap movement). If the detected movement is greater than or equal to the threshold value, the NFC circuit 40 can potentially be activated. But, if no movement that is greater than or equal to the threshold value is detected, the NFC circuit 40 is not activated (even if the NFC circuit 40 is within the required proximity of the NFC tag 45 such that NFC communications can potentially be performed). Therefore, in some embodiments this feature operates to enable NFC when the following two conditions are simultaneously met, or are both met within an establish time interval: (i) an acceleration or an acceleration profile that is greater than or equal to a threshold value is detected (indicating, e.g., a tap or other "bump" action between the portable pump 60 and the NFC tag 45), and (ii) the NFC circuit 40 is in proximity with the NFC tag 45 such that communications therebetween using NFC can occur. In some embodiments, the feature provided by the accelerometer 50 can be activated or deactivated based on a user's or clinician's selection of the feature via the configuration parameters of the portable pump 60. In some embodiments, the accelerometer 50 can be used in conjunction with the NFC circuit 40 in other ways so as to include the detection of a movement into the process for activating or completing changes to the portable pump 60 that correspond to the NFC tag 45.

In some embodiments, the portable pump 60 can be configured to respond differently when the acceleration threshold value is detected by the accelerometer 50 as compared to when the acceleration threshold value is not detected. For example, as described previously, in response to the detection of the NFC tag 45 by the NFC circuit 40 the user may be asked to confirm via the user interface 62 whether to initiate a change to the portable pump 60, such as initiating a bolus of insulin. However, if an acceleration that meets or exceeds the established threshold is detected by accelerometer 50, and the NFC tag 45 is simultaneously detected (or detected within a threshold time limit) by the NFC circuit 40, in some cases the portable pump 60 may initiate a bolus without requiring additional user confirmation. Still, in some cases additional user confirmation may nevertheless be required before the bolus is initiated.

Figure 2:
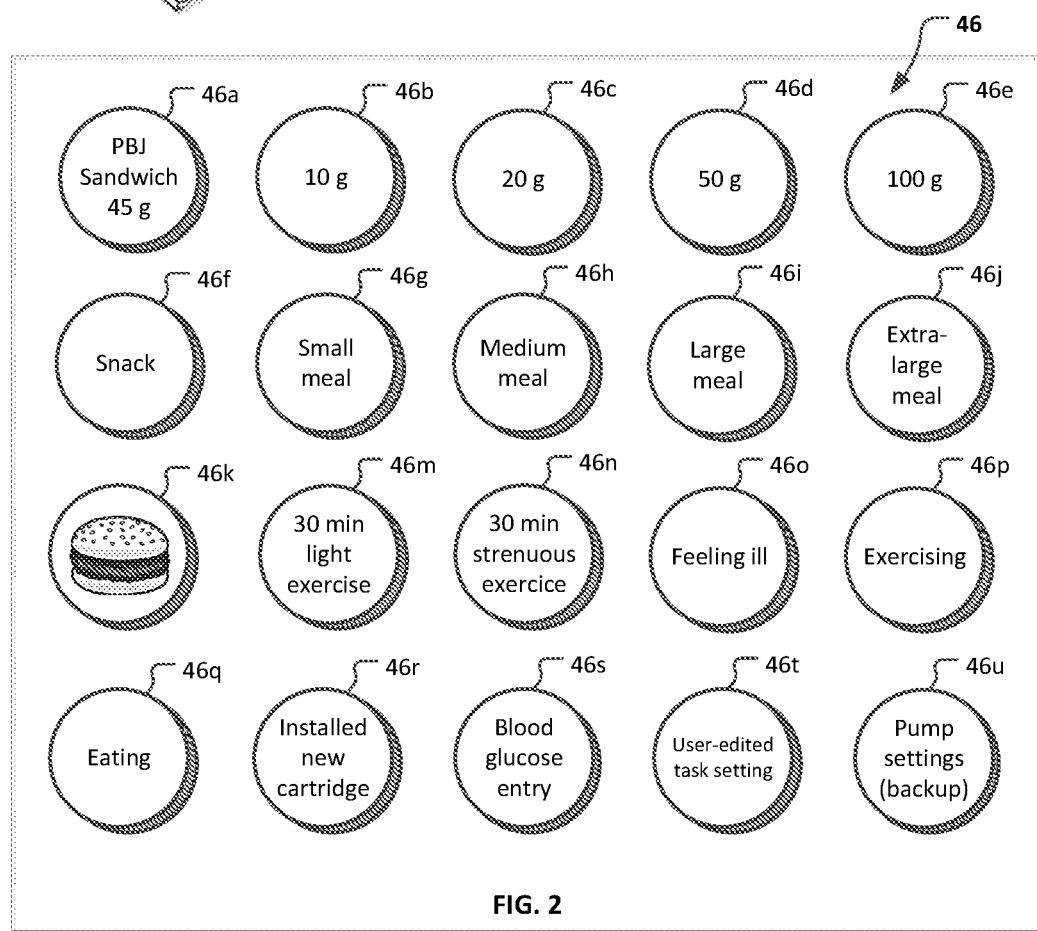
FIG. 2 depicts an assortment of example NFC tags that can be used with the infusion pump systems described herein.

Referring now to FIGS. 1 and 2, a set of example NFC tags 46 can be employed for communicating with the portable pump 60 as needed by the user of the infusion pump system 10. For example, some or all of the set of NFC tags 46 can be selected to correspond with the user's commonly performed tasks associated with using the infusion pump system 10. The NFC tags 46 can be distinctly labeled with text, numbers, graphics, colors, textures, braille, photos, symbols, icons, and the like (and combinations thereof) to assist the user to properly and conveniently distinguish between the various types of NFC tags 46. In some embodiments, the NFC tags 46 can have different physical sizes and shapes, and such sizes and shapes can correspond to an amount of carbohydrates associated with the NFC tags 46. In particular embodiments, an assortment of multiple NFC tags 46 can be included on a sheet of flexible plastic film or paper, in a pocket-sized book, on a key ring, in a container, and in many other convenient storage and handling configurations.

In one example, a parent may pack a lunch for a diabetic child to take to school, and one or more NFC tags 46 corresponding to the particular lunch food can be packed along with the lunch. Or, the NFC tags 46 can be carried by the child (e.g., in a pocket, worn on a necklace or article of clothing). At the school lunchroom, the child can simply tap the child's infusion pump to the NFC tags 46 in order to command the pump to deliver an appropriate bolus dispensation of insulin in correspondence to the food consumed. Thus, as this example shows, using the NFC tags 46 the user can efficiently, accurately, and conveniently initiate commands to the infusion pump system 10 by activating NFC communications between the infusion pump system 10 and the NFC tags 46 (and, optionally, without the need to input a series of menu selections or other more complex user interface actions). In addition, as will be described further, particular NFC tags 46 can be used to receive and store data from the infusion pump system 10.

Some people often eat the same types of foods on a relatively regular basis. A user of the infusion pump system 10 can therefore obtain or make NFC tags that correspond to the food items that the user commonly consumes. For example, the NFC tag 46a (FIG. 2) for a peanut butter and jelly sandwich could be readily used by a user that regularly consumes such sandwich. As described previously, NFC tag 46a can have associated with it (either on the NFC tag 46a, or in the control circuitry of the portable pump 60 in association with a unique identifier of the NFC tag 46a) data such as the grams of carbohydrates of the food represented by the NFC tag 46a. In addition to the grams of carbohydrates, the user's preferred way to deliver a corresponding bolus can be included in the data associated with the NFC tag 46a. For example, the preferred delivery schedule of insulin for the user to counteract the consumption of a peanut butter and jelly sandwich may be 40% of the bolus insulin amount delivered immediately and 60% spread over the next three hours. Of course, a different user may have a different preferred delivery schedule that can be used in correspondence with NFC tags used by the different user. For another type of food item, the preferred delivery schedule of insulin for the user may be other than 40% immediately and 60% spread over the next three hours. For example, for a piece of pie, as represented by the NFC tag 45, the preferred delivery schedule of insulin for the user may be 50% immediately and 50% spread over the next two hours. As such, the data associated with NFC tag 45 can include the corresponding preferred delivery schedule of insulin of 50% immediately and 50% spread over the next two hours.

Still further, other data, in addition to grams of carbohydrates and preferred insulin delivery schedules, can be associated with the NFC tags 46. For example, in some embodiments the fat content, type of fat content, fiber content, protein content, and the like, of the food represented by the NFC tags 46 can be associated with the NFC tags. In some embodiments, such data can be incorporated into a recommended insulin dispensation for the user as calculated by the control circuitry of the portable pump 60. For example, in some instances meals with increased fat can lead to delayed absorption of the carbohydrates, and thus a bolus determined based on other food contents beyond just carbohydrates, (e.g., fat and protein) may be beneficial.

While a user of the infusion pump system 10 may consume certain foods like a peanut butter and jelly sandwich fairly regularly, in some circumstances, the user may consume a food item for which the user does not have a dedicated NFC tag 46. In those circumstances, NFC tags 46b, 46c, 46d, and 46e can be used if the user so desires. To use the NFC tags 46b, 46c, 46d, and 46e, the user will estimate the carbohydrate content of the foods that the user has or will soon consume. If, for example, the user will consume food having a carbohydrate content of about 10 grams, the user can activate NFC between the portable pump 60 and the NFC tag 46b (where the NFC tag 46b corresponds to 10 grams of carbohydrates). In response, the portable pump 60 may determine a recommended bolus of insulin and either initiate the dispensation of the bolus or prompt the user to confirm via the user interface 62 the initiation of the recommended bolus of insulin. The NFC tags 46c, 46d, and 46e can be similarly used in situations where about 20, 50, or 100 grams of carbohydrates, respectively, have been or will soon be consumed. Of course, the carbohydrate quantities of 10, 20, 50, and 100 grams associated with NFC tags 46b, 46c, 46d, and 46e are merely illustrative, as NFC tags 46 having any other quantities of carbohydrates (and other data content) can be created and used in accordance with the systems and methods provided herein.

In another example that is relevant to the use of NFC tags 46b, 46c, 46d, and 46e, it may be determined that the user has or will consume food having a carbohydrate content of about 30 grams. In a first example for handling such a scenario, in some embodiments the portable pump 60 can be configured to add together successive NFC tag data entries to input the total carbohydrate quantity desired by the user. For example, to input 30 grams of carbohydrates, the user may first activate NFC between the portable pump 60 and the NFC tag 46b to input 10 grams of carbohydrates. Before confirming a bolus dispensation corresponding to the 10 grams, the user can then activate NFC between the portable pump 60 and the NFC tag 46c to input an additional 20 grams of carbohydrates, for 30 total grams of carbohydrates. In other words, the portable pump 60 can add the first NFC input of 10 grams of carbohydrates and the second NFC input of 20 grams of carbohydrates together to arrive at a total of 30 grams of carbohydrates. The portable pump 60 can then present to the user via the display 65 a prompt that asks the user to confirm the input of 30 grams of carbohydrates to be consumed, and to confirm the acceptance of the associated recommended bolus dispensation of insulin. For example, in the example portable pump 60 provided, the user can confirm the acceptance of such information by activating the button 64c. In other examples, other techniques for confirming acceptance can be used, as described further herein.

While the first example immediately above used NFC tags 46b and 46c to enter a total of 30 grams of carbohydrates into portable pump 60, in a second example technique for entering 30 grams of carbohydrates, the single NFC tag 46b (10 grams of carbohydrates) can be used to activate NFC circuit 40 three times to cause three successive data entries of 10 grams of carbohydrates each. The three successive data entries of 10 grams of carbohydrates each can be added together by portable pump 60 in the manner described above, resulting in a total entry of 30 grams of carbohydrates. The user can then confirm the entry of 30 grams and accept the recommended bolus using the user interface 62. By way of these examples, it should be appreciated that by combining successive data entries using various NFC tags 46, such as NFC tags 46b, 46c, 46d, and 46e, any desired amount of grams of carbohydrates can be entered into portable pump 60 using NFC technology. While in these examples the portable pump 60 was configured to add together successive NFC data entries, in some embodiments the portable pump 60 can alternatively be configured to not add such successive entries together. In some embodiments, the user (or another individual such as a parent or clinician) can selectively configure the portable pump 60 to either add successive entries together or to not add successive entries together.

Still referring to FIGS. 1 and 2, NFC tags 46f, 46g, 46h, 46i, and 46j are examples of NFC tags that can be conveniently used to enter an estimated quantity of carbohydrates (and optionally other nutritional and operational data) in correspondence to an amount of food consumed, or soon to be consumed, by the user. In general, the NFC tags 46f, 46g, 46h, 46i, and 46j can be used as an alternative to counting carbohydrates and entering into the portable pump 60 (via the user interface 62 or via the NFC tags 46b, 46c, 46d, and 46e) the numerical carbohydrate intake quantity to be consumed (e.g., 10, 20, or 30 grams, etc.). As shown, the NFC tags 46f, 46g, 46h, 46i, and 46j can be graduated in relation to an approximate amount of food consumed (e.g., "snack," "small meal," "medium meal," "large meal," and "extra-large meal"). Such approximations may be appropriate for use by some infusion pump system 10 users or in some situations of using the infusion pump system 10. Accordingly, when the user presents the NFC tag 46f (corresponding to a "snack") to portable pump 60 to activate NFC between the NFC tag 46f and the portable pump 60, a lesser quantity of carbohydrates will be input to portable pump 60 in comparison to when the user presents the NFC tag 46i ("large meal") to the portable pump 60. Of course, the NFC tags 46f, 46g, 46h, 46i, and 46j can be configured to correspond to different levels of carbohydrates for different users. For example, a "large meal" for a male may typically include a greater quantity of carbohydrates than a "large meal" for a female. Therefore, in one example a male user of portable pump 60 may configure (program) NFC tag 46i to correspond to 200 grams of carbohydrates, while a female user may configure NFC tag 46i to correspond to 150 grams of carbohydrates. It should be appreciated that the quantity of carbohydrates (and other such data) associated with the NFC tags 46f, 46g, 46h, 46i, and 46j can be individualized for the particular user of the infusion pump system 10.

NFC tag 46k is an example of a NFC tag that includes an iconic identifier on a surface of the NFC tag 46k. In this example, an icon of a hamburger is printed on the NFC tag 46k. Using icons, symbols, and other types of non-text identifiers can be advantageous for some users. For example, certain users of the NFC tags 46 may not have fluency in the language printed on the NFC tags 46. Or, a user of the NFC tags 46 may be illiterate, a child, or have poor eyesight. In another example, the NFC tags 46 can include Braille or other raised patterns or shapes for use by blind users or users with limited vision.

NFC tags 46m and 46n are examples of NFC tags that correspond to an exercise activity to be performed by the user of the infusion pump system 10. Diabetic individuals typically experience a blood sugar reduction in response to the performance of exercise. Therefore, to maintain the user's blood sugar level within a target range it can be beneficial to temporarily reduce the user's basal rate to an extent that correlates to the level of physical exertion performed or to be performed. When reducing basal insulin, the appropriate extent of reduction will depend on factors such as intensity, duration, the individual, and mode of exercise. A basal rate can be reduced prior to, during, and after exercise depending on the situation. For example, in response to performing light exercise over a 30-minute period, the user may present NFC tag 46m to the user's portable pump 60. The NFC tag 46m, for example, may be associated with a command for a 50% reduction of the basal insulin dosages over the next 6 hours. In another example, in response to performing 30 minutes of strenuous exercise, the user may present NFC tag 46n to the user's portable pump 60. The NFC tag 46n may, for example, be associated with a command for a 50% reduction of basal insulin over the next 10 hours. Such factors can be individualized for the particular user, and the particular user's NFC tags 46m and 46n can be programmed accordingly. In some embodiments, the NFC tags 46m and 46n can be used in combinations to additively arrive at other levels of exertion or duration in a manner analogous to that described above in reference to NFC tags 46b-46e.

NFC tags 46o, 46p, 46q, and 46r are examples of NFC tags that can be used to automate the entry and time-based archival of event occurrences into the portable pump 60. In other words, the NFC tags 46o-46r can be used to add descriptive information to the data that is stored within the portable pump 60. Such labeling of data is also known as data tagging or the creation of metadata. For example, if the user is feeling ill, the user can present the NFC tag 46o to the user's portable pump 60. Upon the activation of NFC between the NFC tag 46o and the NFC circuit 40, a command is executed that causes the portable pump 60 to store metadata identifying that the user feels ill at the time that the NFC was activated. In other examples, when the user is exercising, eating, or has installed a new medicine cartridge, the user can present the NFC tags 46p, 46q, or 46r, respectively, to the user's portable pump 60. Upon the activation of NFC between the NFC tags 46p, 46q, or 46r and the NFC circuit 40, a command is executed that causes the portable pump 60 to store metadata identifying that the user is exercising, eating, or has installed a new medicine cartridge at that time. In another example (not shown in FIG. 2), a NFC tag can be used to indicate when the user has changed the infusion site on the user's body. Accordingly, the presentation of such a NFC tag to the user's portable pump 60 will cause metadata to be stored that identifies that the user changed infusion sites about at the time that NFC was activated between the NFC tag and the NFC circuit 40.

NFC tags 46 can also be used to automatically enter other types of commands to the portable pump 60. NFC tags 46 can thereby reduce the need for using buttons 63a-63b and 64a-64c of the user interface 62 to shuffle through various menus. One example of a type of command that can be automated is the entry of a blood glucose reading using a NFC tag 46s. For example, the user may periodically measure the user's blood glucose level using a blood glucose meter that analyzes a sample of the user's blood using a test strip. The numerical results provided by such a test can then be entered into the user's portable pump 60 to provide the portable pump 60 with the user's actual current blood glucose level. The NFC tag 46s can be used to "key-up" the portable pump 60 for the entry of the numeric blood glucose level. For example, when the user presents the NFC tag 46s to the portable pump 60 and NFC is established therebetween, a command is executed that causes the portable pump 60 to get ready to receive the blood glucose data with no other preliminary button pushing required. In such fashion, the user can save time and can operate the infusion pump system 10 with greater convenience using the NFC tag 46s. Of course, many other types of commands for the portable pump 60 can be similarly automated using the NFC tags 46.

NFC tag 46t is an example of a "blank" NFC tag that can be programmed or scripted and thereafter used to input a variety of commands to the portable pump 60. In some embodiments, the NFC tag 46t can be programmed by the portable pump 60. In particular embodiments, the NFC tag 46t can be programmed by another device that has NFC functionality (e.g., a smart phone, tablet computer, personal computer, and the like). In some embodiments, the NFC tag 46t can be written to only once, and thereafter the NFC tag 46t becomes a read-only NFC tag. In other embodiments, the NFC tag 46t can be written to, and re-written to, multiple times.

The programmable NFC tag 46t can be utilized in a variety of advantageous ways. For instance, as described above a user of the infusion pump system 10 can program the NFC tag 46t to be associated with data corresponding to a certain type of food that the user consumes (e.g., a large apple having 30 carbs, etc.). In another category of examples, the user can configure the NFC tag 46t to be used to initiate a particular operation by the portable pump 60. For example, when changing an infusion set 70 or a medicine cartridge, the user may first want to pause the portable pump 60. Accordingly, the programmable NFC tag 46t can be programmed to pause the portable pump 60 if the portable pump 60 is in the run mode at the time that NFC is activated between the programmed NFC tag 46t and the portable pump 60. Then, after changing the infusion set 70 or the medicine cartridge, the user may desire to prime the infusion set 70 and begin normal operations of the infusion pump system 70. Therefore, the programmable NFC tag 46t can be programmed to prime and thereafter start the portable pump 60 if the portable pump 60 is in the pause mode at the time that NFC is activated between the programmed NFC tag 46t and the portable pump 60. In accordance with the examples provided above, it can be appreciated that programmable NFC tag 46t provides a versatile and customizable functionality whereby users of infusion pump system 10 can enhance and simplify interactions with the user interface 62 and operational capabilities of the portable pump 60.

It should be understood from the description herein that a multitude of other beneficial uses for the NFC tags are envisioned for use in combination with a medical infusion pump system. Here, the infusion pump system 70 performs a variety of tasks receives various types of user entry associated with operating the infusion pump system 70. Any one of these tasks or types of user entry associated with operating the infusion pump system 70 can be communicated to the control circuitry of the portable pump 60 via the NFC circuit 40 using the corresponding NFC tag. For example, a NFC tag can be used to confirm a user input or pump parameter setting. A NFC tag of this type can be used in conjunction with other NFC tags or input methods to eliminate the need for entering a confirmation using the user interface 62. In another example, a NFC tag can be used to enter a task command to calibrate a glucose sensor. That is, for example, a NFC tag can trigger the portable pump 60 to use the last blood glucose value entered by the user to calibrate a continuous glucose monitor that is in communication with the infusion pump system 70. In another example, in some circumstances, such as when the infusion pump system 70 is used by a child or when the infusion pump system 70 is used during sports activities, it may be desirable to temporarily deactivate the functionality of the buttons 63a, 63b, 64a, 64b, and 64c of the user interface 62. In such circumstances, NFC tags can be used to lock, and subsequently unlock, the buttons 63a, 63b, 64a, 64b, and 64c of the user interface 62. In still another example, a NFC tag can be used to stop or pause the portable pump 60, such as when the user has disconnected the portable pump 60 from the infusion set 70 to bathe. NFC tags can also be used to enter a task or user command to change to a different basal pattern. Such changes may be beneficial during weekends versus weekdays, during menses versus the rest of the month, and so on. It should be understood that the example uses for NFC tags provided herein are non-limiting, and that other uses for the NFC tags are also envisioned.

NFC tag 46u is an example of another use for a "blank" NFC tag that can be written to. In this example, the NFC tag 46u is used to store the user configuration settings for the user's portable pump 60. Using the NFC tag 46u in this manner can provide a way to create a back-up copy of the user's configuration settings. Having a back-up copy of the user's configuration settings can be advantageous in a variety of circumstances. For example, if the user's portable pump 60 is damaged such that a repair is necessitated, the NFC tag 46u containing the user's settings can be used to conveniently reprogram the repaired portable pump 60 by presenting the NFC tag 46u to the repaired portable pump 60. Or, if the user's portable pump 60 is damaged beyond repair, the user's settings can be conveniently uploaded to a replacement portable pump 60 by presenting the NFC tag 46u to the replacement portable pump 60. Or, if the user desires different settings for different situations, such NFC tags comprising user settings can conveniently be used to change the settings.

Figure 3:
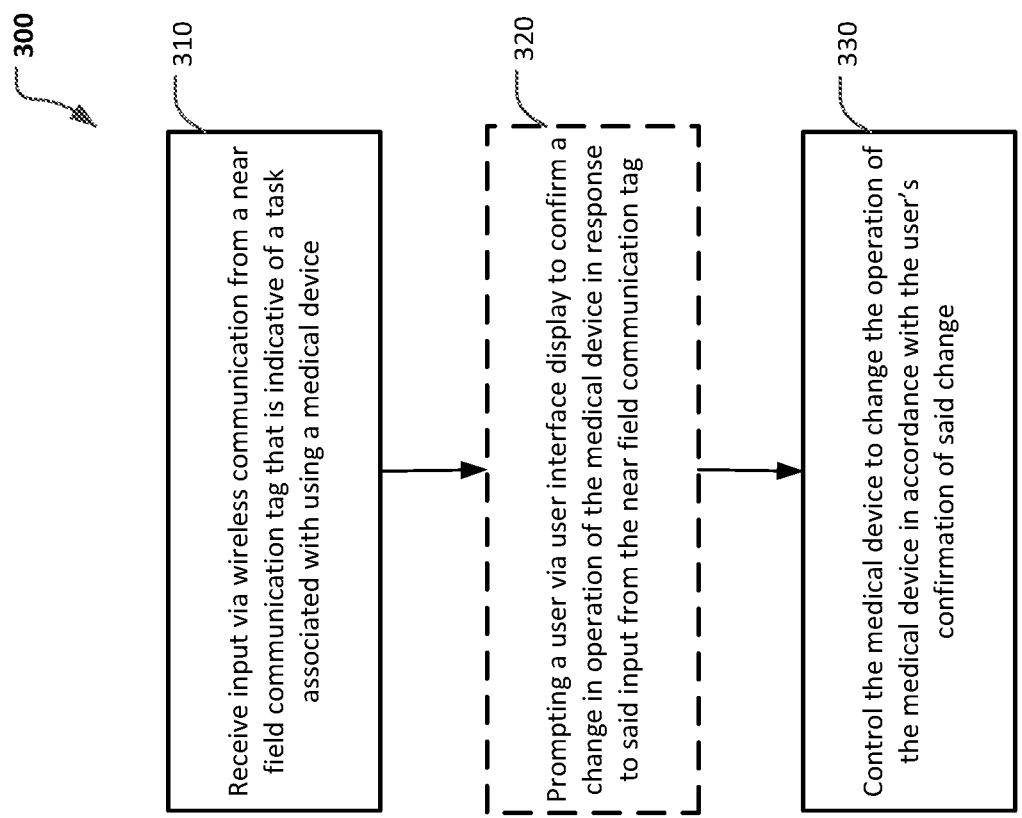
FIG. 3 is a flowchart describing a process of using an infusion pump system equipped with NFC capabilities in accordance with some embodiments.

Referring now to FIG. 3, the control circuitry of a medical device (e.g., a portable infusion pump in this embodiment) that includes NFC equipment can implement a process 300 of receiving commands from a NFC tag and controlling the medical device in accordance with the commands. Such a process 300, for example, can be implemented by the control circuitry housed in the portable pump 60 of the infusion pump system 10 (FIG. 1), and other embodiments of infusion pump systems provided herein (e.g., FIGS. 4, 5, 6, and 7).

In operation 310, the control circuitry of a medical device can receive input via wireless communication from a NFC tag. The input can be indicative of a task associated with using the medical device. A medical device that can perform operation 310 is exemplified in FIG. 1, where the infusion pump system 10 includes a NFC circuit 40 that is in electrical communication with the control circuitry of the infusion pump system 10. As explained, the NFC circuit 40 can function to send and receive communications from the NFC tag 45 when NFC is activated by placing the NFC tag 45 within the requisite proximity with the portable pump 60 such that NFC communications are activated.

In some embodiments, NFC tags can be scripted with executable code that can be transferred to the medical device's control circuitry via the NFC circuit in communication with the control circuitry. In those embodiments, the control circuitry can execute the code as received from the NFC tag. In other embodiments, the NFC tag can communicate a unique identifier, such as a serial number, to the control circuitry via the NFC circuit. In response to the receipt of such a unique identifier by the control circuitry, the control circuitry can execute certain coded operations that are associated with the particular unique identifier received.

An example of operation 310 is provided in FIG. 1, where the NFC tag 45 is presented to the NFC circuit 40 of the portable pump 60. In response, the control circuitry of the portable pump 60 executed commands indicative of an entry by the user of an intent to initiate a bolus dispensation to counteract the consumption of 60 grams of carbohydrates.

In operation 320, the control circuitry optionally provides a prompt via the user interface display to confirm a change in operation of the medical device in response to said input from the near field communication tag. Such a prompt may be advantageously used to confirm the user's intent to change the operation of the medical device before the control circuitry actually implements the change.

An example of operation 320 is provided in FIG. 1, where the control circuitry of the portable pump 60 generated the illustrated textual prompt on the display 65. The prompt provides a description of the potential change in operation ("Consume 60 g of carbs? Press enter to initiate a bolus of 4.0 U."). By pressing button 64c the user can confirm the user's intent to implement a change in the operation of the infusion pump system 10. Alternatively or additionally, other techniques can be used to confirm the user's intent to change the operation of the medical device before the control circuitry actually implements the change. For example, in some embodiments the user can be required to present the same NFC tag to the NFC circuit multiple times within a limited period of time (e.g., two quick taps, three taps within a period of two second, or the like) to confirm the user's intent. In particular embodiments, the user can be required to make contact (e.g., by tapping or otherwise bumping, or the like) between the pump device and the NFC tag, and such contact can be considered to be sufficient user confirmation. In such embodiments, one or more accelerometers in the pump device may be used to detect the requisite contact(s). In other embodiments, some types of tasks entered using a NFC tag require user confirmation while other types of tasks entered using a NFC tag do not require user confirmation. In still other embodiments, a particular task that is entered using a NFC tag will require a user confirmation in some circumstances, but not in other circumstances. An infusion pump system may be configurable to select between the use of these types of alternative techniques for user confirmation. In some embodiments, such various alternatives can be combined for use with various types of tasks associated with a single pump system. In particular embodiments, the infusion pump system can be configured to not require user confirmation for some, or all, tasks and commands entered using NFC tags.

In operation 330, after receiving confirmation from the user to implement the change associated with the input from the NFC tag, the control circuitry can control the medical device to change the operation of the medical device in accordance with the user's confirmation of the change.

Again, in regard to the example of FIG. 1, when the user confirms by pressing button 64c the change to the infusion pump system 10 related to the user's consumption of 60 grams of carbohydrates, the control circuitry can thereafter control the portable pump 60 to deliver the corresponding bolus dispensation of insulin.

Figure 4:
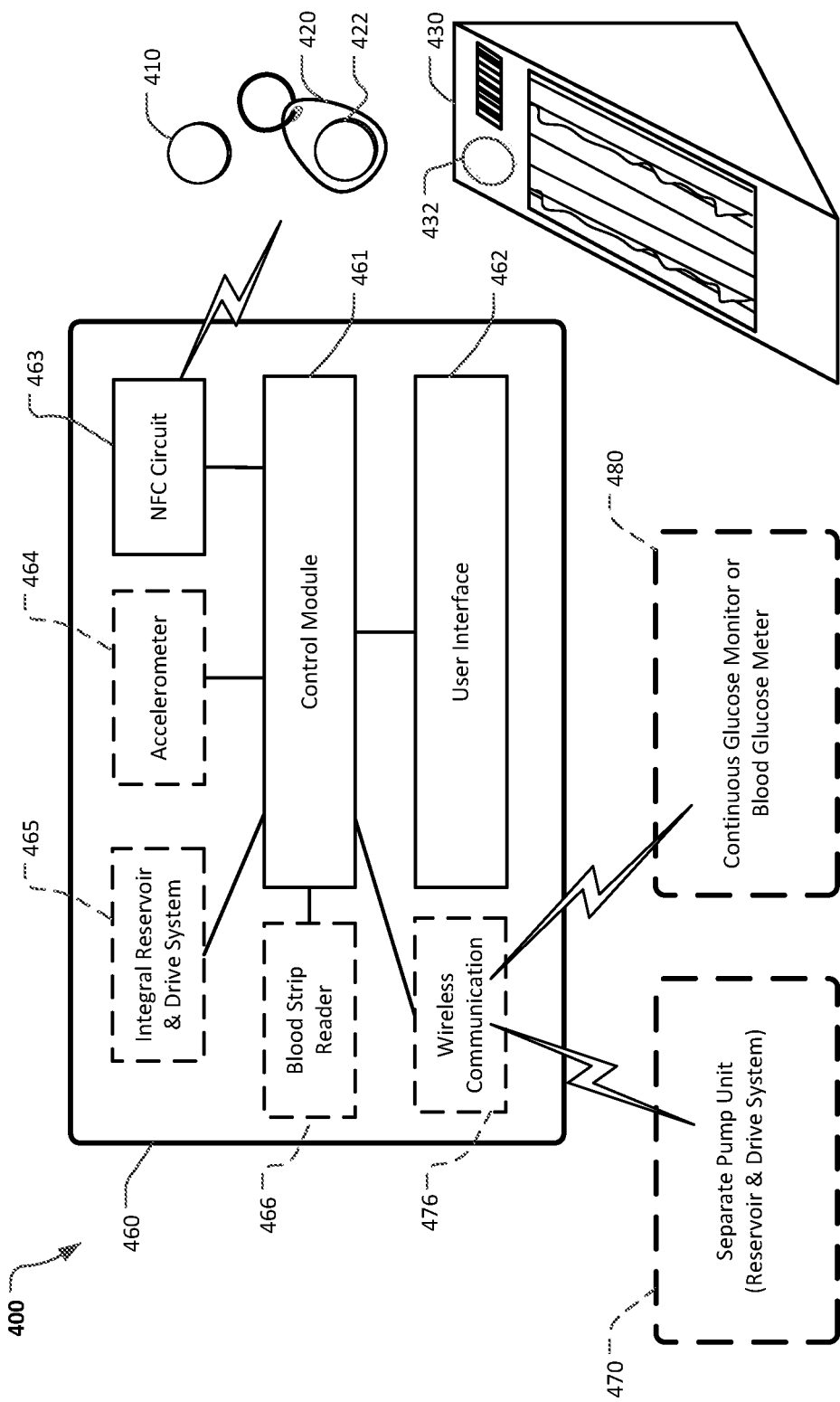
FIG. 4 is a schematic diagram of an infusion pump system with NFC capabilities in accordance with some embodiments.

Now referring to FIG. 4, a schematically represented example portable infusion pump system 400 can include a pump controller device 460 that is equipped with a NFC circuit 463 for providing NFC capabilities. The NFC circuit 463 can be used by the portable infusion pump system 400 to communicate with example NFC tags 410, 422, and 432. Certain items of the portable infusion pump system 400 are shown with dashed lines to indicate that they are optional or alternative items, as explained below.

The pump controller device 460 includes a control module 461 that can be made up of one or more components. In this embodiment, the control module 461 is configured to communicate control or power signals to the other components of the portable infusion pump system 400, and to receive inputs and signals therefrom. In some embodiments, the control circuitry can include a main processor board that is in communication with a power supply board. The control circuitry can include at least one processor that coordinates the electrical communication to and from the control module 461 and other components of the portable infusion pump system 400. For example, the user interface 462 of the pump controller device 460 can include input components and output components that are electrically connected to the control circuitry of the control module 461. In some embodiments, the control module 461 can receive input commands from a user's button selections (e.g., buttons as shown in FIG. 1, 5, 6, or 7), and thereby cause the display device of the user interface 462 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge, the amount of battery life remaining, or the like).

The processor of the control module 461 can be arranged on a main processor circuit board of the control module 461 along with a number of other electrical components such as computer-readable memory devices. The control circuitry can be programmable in that the user or a clinician may provide one or more instructions to adjust a number of settings for the operation of the portable infusion pump system 400. Such settings may be stored in the memory devices of the control module 461. Furthermore, the control module 461 may include one or more dedicated memory devices that store executable software instructions for the processor. The control module 461 may include other components, such as sensors, that are electrically connected to the main processor board. A rechargeable battery pack (not shown) may provide electrical energy to the control module 461, and to other components of the pump controller device 460 (e.g., user interface 462, NFC circuit 463, and others).

The user interface 462 of the pump controller device 460 permits a user to monitor and control the operation of the pump controller device 460. For example, the user interface 462 can include a display device having an active area that outputs information to a user, and buttons (e.g., actuatable buttons as shown in FIG. 1, 5, 6, or 7 or touchscreen buttons defined on the display device) that the user can use to provide input. The display device can be used to communicate a number of settings or menu options for the portable infusion pump system 400. The display may include an active area in which numerals, text, symbols, images, or a combination thereof can be displayed (refer, for example, to FIG. 1). For example, the user may press one or more buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge, or the like). In some embodiments, the user can adjust the settings or otherwise program the control module 461 via the user interface 462. For example, in embodiments of the portable infusion pump system 400 configured to dispense insulin, the user may press one or more of the buttons of the user interface 462 to change the dispensation rate of insulin or to request that a bolus of insulin be dispensed immediately or at a scheduled, later time.

The pump controller device 460 also includes the NFC circuit 463 in electrical communication with the control module 461, such that power and signal data can be transferred between the NFC circuit 463 and the control module 461. The NFC circuit 463 in this embodiment includes a NFC transceiver circuit that is coupled to a loop inductor (e.g., coil) that serves as an antenna for wirelessly communicating with external NFC tags (e.g., NFC tags 410, 422, and 432). The NFC circuit 463 can act as an interface to facilitate the transfer of data between the example NFC tags 410, 422, and 432 and the control module 461 using NFC protocols. The coil of the NFC circuit 463 inductively supplies electrical power to the NFC tags 410, 422, and 432 by way of secondary coils located in the NFC tags 410, 422, and 432 themselves. The respective coils of the NFC circuit 463 and the NFC tags 410, 422, and 432 can also wirelessly exchange two-way data transmissions using the same inductive coupling between the coils.

The example NFC tags 410, 422, and 432 depict some additional advantageous ways of configuring NFC tags to be used in conjunction with the portable infusion pump system 400. In general, NFC tags 410, 422, and 432 include a coil and a microchip. The NFC tags 410, 422, and 432 act as passive listening devices. But when the NFC circuit 463 is located in the requisite proximity to the NFC tags 410, 422, or 432, the coil of the NFC tags 410, 422, or 432 inductively couples with a coil of the NFC circuit 463. When the coils are inductively coupled, electrical power is supplied to the NFC tags 410, 422, or 432 and data can be exchanged between the NFC tags 410, 422, or 432 and the NFC circuit 463. In some embodiments, about a kilobyte of data or more can be stored in the NFC tags 410, 422, and 432 and transferred to the control module 461 via the NFC circuit 463.

The NFC tag 410 is an example of a compact and versatile NFC tag. In some embodiments, NFC tag 410 is about the size of a quarter and is flexible. NFC tag 410 can have an adhesive coating on one surface. In some embodiments, the NFC tag 410 can be incorporated into configurations such as pendants, tiles, chips, stickers, and the like.

The NFC tag 422 is an example of a NFC tag that has been conveniently incorporated onto a keychain 420. In one example use of such a configuration, the keychain 420 can be attached to a gym bag and the NFC tag 422 can be programmed like the NFC tags 46m or 46n of FIG. 2, that indicate that the user is going to perform 30 minutes of light or strenuous exercise respectively. Then, in conjunction with the user's exercise, the user can simply present the NFC tag 422 on the keychain 420 to the user's pump controller device 460 (e.g., tapping the pump controller device 460 against the NFC tag 432 or in proximity to the tag 432) to enter a command corresponding to the performance of the exercise.

The NFC tag 432 in an example of a NFC tag that has been conveniently incorporated onto a food package 430. In this example, the food package 430 is a sandwich container like those commonly available from a vending machine or convenience store. As shown, the NFC tag 432 can be adhered to or otherwise incorporated directly on the exterior of the food package 430. The NFC tag 432 can be preprogrammed with data corresponding to the contents of the food package 430. For example, the NFC tag 432 can be programmed with the number of grams of carbohydrates in the sandwich contained in the food package 430. The user of the portable infusion pump system 400 can conveniently present the NFC tag 432 to the NFC circuit 463 of the pump controller device 460 (e.g., tapping the pump controller device 460 against the NFC tag 432 or in proximity to the NFC tag 432) to enter a command corresponding to the consumption of the sandwich inside of the food package 430.

The pump controller device 460 can also optionally include an accelerometer 464 in electrical communication with the control module 461. In some embodiments, more than one accelerometer 464 can be optionally included. Embodiments of the pump controller device 460 that include the optional accelerometer 464 can utilize the functionality of the accelerometer 464 in conjunction with the NFC circuit 463. That is, the accelerometer 464 can operate in conjunction with the control module 461 and the NFC circuit 463 to supplement the criteria for activating or completing communications between the NFC circuit 463 and the NFC tags 410, 422, or 432. In other words, while in some embodiments, communications between the NFC circuit 463 and the NFC tags 410, 422, or 432 are activated solely based on the proximity therebetween, in other embodiments a threshold acceleration, as determined by the accelerometer 464, must also be detected. An objective for including this feature can be to more clearly ascertain that the user intends to activate NFC when a NFC tag 410, 422, or 432 is within the required proximity with the NFC circuit 463. That is, for example, by requiring the user to tap the pump controller device 460 and the NFC tag 410, 422, or 432 together, the user's intentions for activating NFC may be ascertained with a greater level of confidence.

This optional feature using the accelerometer 464 can function as follows. When motion of the pump controller device 460 is detected by accelerometer 464, a characteristic value of the detected motion can be compared by the control module 461 to a predetermined threshold movement value. If the characteristic value of the detected movement is greater than the threshold value, the NFC circuit 463 can potentially be activated. But, if the characteristic value of the detected movement is not greater than the threshold value, the NFC circuit 463 is not activated (even if the NFC circuit 463 is within the required proximity of the NFC tags 410, 422, or 432 such that NFC communications can be performed). Therefore, in some embodiments this feature operates to enable NFC when the following two conditions are simultaneously met, or are both met within an establish time interval: (i) a characteristic value of the detected movement (e.g., acceleration value) that is greater than a threshold value is detected (indicating, for example, a tap), and (ii) the NFC circuit 463 is in proximity with the NFC tags 410, 422, or 432 such that communications therebetween using NFC can occur.

Still referring to FIG. 4, in some embodiments the pump controller device 460 may also serve as the pump unit for the portable infusion pump system 400, thereby dispensing medicine from the same housing that contains the control module 461 and other components. In those particular embodiments, the pump controller device 460 can be optionally equipped with an integral medicine reservoir and pump drive system 465 in electrical communication with the control module 461. For example, the portable pump 60 depicted in the embodiment of FIG. 1 is an example of this type of configuration. Such embodiments of the portable infusion pump system 400 can employ a reusable pump apparatus (rather than a disposable pump device as will be described below, for example, in connection with FIG. 5). Therefore, in those embodiments, the portable infusion pump system 400 may optionally serve as a reusable device that houses the control module 461 and the integral reservoir and pump drive system 465 within a single housing construct. In those circumstances, the pump controller device 460 can be adapted to receive a medicine cartridge in the form of a carpule that is preloaded with insulin or another medicine. The pump drive system 465 can act upon the fluid cartridge to controllably dispense medicine through an infusion set and into the user's tissue or vasculature. In this embodiment, the user can wear the pump controller device 460 on the user's skin under clothing or in the user's pocket while receiving the medicine dispensed through the infusion set. In some embodiments of the pump controller device 460 that include the optional integral reservoir and pump drive system 465, a refillable medicine reservoir can be incorporated in the pump controller device 460 as an alternative to a medicine cartridge.

Still referring to FIG. 4, as an alternative to the integral medicine reservoir and pump drive system 465, the portable infusion pump system 400 can include a separate pump device 470 (including a reservoir and a drive system) that is in electrical communication with the pump controller device 460. In these embodiments, the separate pump device 470 can be configured as a disposable and non-reusable pump component while the controller device 460 is configured to be reused with a series of the pump devices 470. In the depicted embodiment shown in FIG. 4, wireless communications are used between the separate pump device 470 and the pump controller device 460, using a wireless communication module 476 in the pump controller device 460. The wireless communications of the wireless communication module 476 can utilize any of a variety of wireless communication technologies that have a greater maximum working range than the aforementioned NFC equipment. For example, the wireless communication module 476 can employ BLUETOOTH®, RF (radio frequency), infrared, ultrasonic, electromagnetic induction, and the like, and combinations thereof. Optionally, in some embodiments, the wireless communications of the wireless communication module 476 can utilize NFC equipment. Alternatively, a releasable electrical connection can be used between the separate pump device 470 and the pump controller device 460 so as to provide hardwired electrical communication between the control module 461 of the controller device 460 and the drive system of the pump device 470. One such embodiment of a separate pump device 470 that is removably attachable with the controller device 460 separate pump device 470 is depicted, for example, in FIG. 5 (as described below).

In brief, in embodiments of the portable infusion pump system 400 that include the separate pump device 470, the pump controller device 460 may be configured as a reusable component that provides electronics and a user interface to control the operation of the infusion pump system 400, and the separate pump device 470 can be a disposable component that is discarded after a single use. For example, the separate pump device 470 can be a "one time use" component that is thrown away after the fluid cartridge therein is exhausted. Thereafter, the user can wirelessly connect or removably mount a new separate pump device 470 to the reusable pump controller device 460 for the dispensation of a new supply of medicine from the new separate pump device 470. Accordingly, the user is permitted to reuse the pump controller device 460 (which may include complex or valuable electronics) while disposing of the relatively low-cost separate pump device 470 after each use. Such a portable infusion pump system 400 can provide enhanced user safety as a new separate pump device 470 is employed with each new fluid cartridge.

Still referring to FIG. 4, the pump controller device 460 can also optionally include an integral blood strip reader 466 mounted therein and being in electrical communication with the control module 461. In such embodiments of the pump controller device 460, test strips (e.g., blood test strips) containing a sample of the user's blood can be inserted into the blood strip reader 466 portion of the pump controller device 460, to be tested for characteristics of the user's blood. The results of the analysis can be used to affect the dosage or schedule of medicine dispensations from the pump controller device 460 to the user as determined by the control module 461. As an alternative to or in addition to the internal blood strip reader 466 housed in the pump controller device 460, the pump controller device 460 can be configured to communicate with an external blood glucose monitor 480, such as a continuous glucose monitor or a handheld blood glucose meter. For example, the test strips (e.g., glucose test strips) containing a sample of the user's blood can be inserted into external handheld blood glucose meter 480, which then analyzes the characteristics of the user's blood and communicates the information (via a wired or wireless connection) to the pump controller device 460. In other embodiments, the user interface 462 of the pump controller device 460 can be employed by the user to manually enter the user's blood glucose information as reported on a screen of a handheld blood glucose meter 480. In still other embodiments, the portable infusion pump system 400 can include a continuous blood glucose monitor 480 (as an alternative to or in addition to the internally housed blood strip reader 466) that can continuously monitor characteristics of the user's blood and communicate the information (via a wired or wireless connection) to the pump controller device 460. One example of this configuration is described below in connection with FIG. 6.

Figure 5:
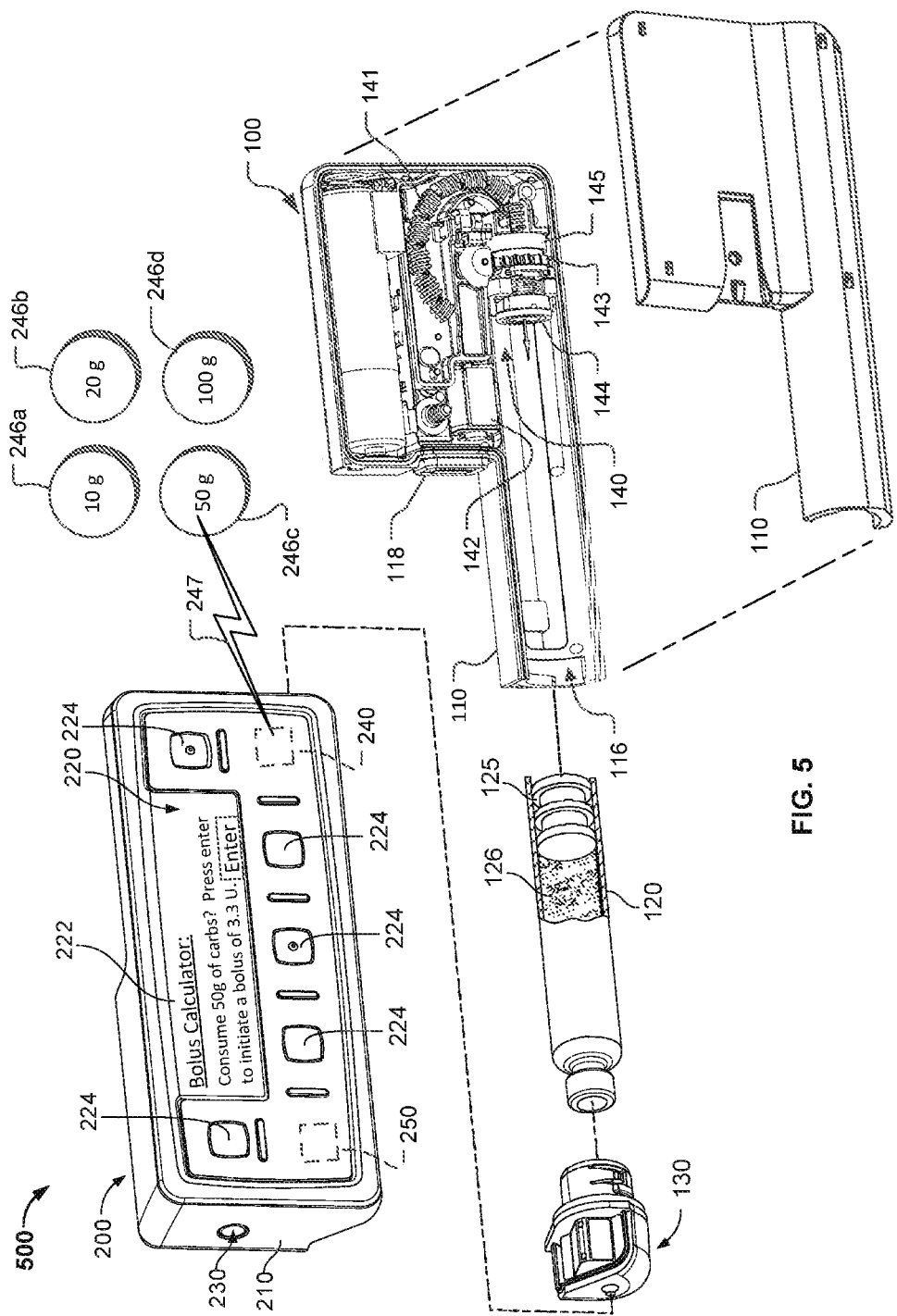
FIG. 5 is an exploded perspective view of another infusion pump system with NFC capabilities in accordance with some embodiments.

Referring now to FIG. 5, some embodiments of an infusion pump system 500 equipped with NFC capabilities can include a removable pump device 100 (shown in an exploded view) and a controller device 200 that communicates with the pump device 100. The pump device 100 in this embodiment includes a pump housing structure 110 that defines a cavity 116 in which a fluid cartridge 120 can be received. The pump device 100 can also include a cap device 130 to retain the fluid cartridge 120 in the cavity 116 of the pump housing structure 110. The pump device 100 can include a drive system 140 that advances a plunger 125 in the fluid cartridge 120 so as to dispense fluid 126 therefrom.

In some embodiments, the controller device 200 communicates with the pump device 100 to control the operation of the drive system 140. When the controller device 200, the pump device 100 (including the cap device 130), and the fluid cartridge 120 are assembled together, the user can (in some embodiments) conveniently wear the infusion pump system 500 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device 100 (having a new fluid cartridge 120) to the reusable controller device 200 for the dispensation of fluid from a new fluid cartridge 120. Accordingly, the user is permitted to reuse the controller device 200 (which may include complex or valuable electronics, as well as a rechargeable battery) while disposing of the relatively low-cost pump device 100 after each use. Such an infusion pump system 500 can provide enhanced user safety as a new pump device 100 (and drive system therein) is employed with each new fluid cartridge 120.

Briefly, in use, the pump device 100 is configured to removably attach to the controller device 200 in a manner that provides a secure fitting, an overall compact size, and a reliable electrical connection that can be resistant to water migration. For example, the controller device 200 can include a controller housing 210 having a number of features that mate with complementary features of the pump housing structure 110. In such circumstances, the controller device 200 can removably attach with the pump device 100 in a generally side-by-side configuration. The compact size permits the infusion pump system 500 to be discrete and portable. Moreover, at least one of the pump device 100 or the controller device 200 can include a release member that facilitates an easy-to-use detachment and replacement process.

As shown in FIG. 5, the pump device 100 can include an electrical connector 118 (e.g., having conductive pads, pins, and the like) that is exposed to the controller device 200 and that mates with a complementary electrical connector (not shown) on the adjacent face of the controller device 200. The electrical connection between the pump device 100 and the controller device 200 provides the electrical communication between the control circuitry housed in the controller device 200 and at least a portion of the drive system 140 or other components of the pump device 100. For example, in some embodiments, the electrical connection between the pump device 100 and the controller device 200 can permit the transmission of electrical control signals to the pump device 100 and the reception of feedback signals (e.g., sensor signals) from particular components within the pump device 100. The electrical connection between the pump device 100 and the controller device 200 may similarly facilitate transmission of one or more power signals for sharing electrical power therebetween.

The pump device 100 may include a drive system 140 that is controlled by the removable controller device 200. Accordingly, the drive system 140 can accurately and incrementally dispense fluid from the pump device 100 in a controlled manner. The drive system 140 may include a flexible piston rod 141 that is incrementally advanced toward the fluid cartridge 120 so as to dispense the medicine from the pump device 100. At least a portion of the drive system 140 is mounted, in this embodiment, to the pump housing structure 110. In some embodiments, the drive system 140 may include a number of components, such as an electrically powered actuator (e.g., reversible motor 142 or the like), a drive wheel 143, a bearing 145, the flexible piston rod 141, and a plunger engagement device 144. In this embodiment, the reversible motor 142 drives a gear system to cause the rotation of the drive wheel 143 that is coupled with the bearing 145. The drive wheel 143 may include a central aperture with an internal thread pattern, which mates with an external thread pattern on the flexible piston rod 141. The interface of the threaded portions of the drive wheel 143 and flexible piston rod 141 may be used to transmit force from the drive wheel to the flexible piston rod 141. Accordingly, in the embodiment of FIG. 5, the drive wheel 143 is the driver while the flexible piston rod 141 is the driven member. The rotation of the drive wheel 143 can drive the flexible piston rod 141 forward in a linear longitudinal direction to cause the plunger engagement device 144 to nudge the plunger 125 within the fluid cartridge 120 so as to dispense fluid 126 therefrom.

Still referring to FIG. 5, the controller device 200 can include a user interface 220 that permits a user to monitor and control the operation of the pump device 100. In some embodiments, the user interface 220 can include a display device 222 and one or more user-selectable buttons (e.g., several buttons 224 are shown in the embodiment of FIG. 5). The display device 222 can include an active area in which numerals, text, symbols, images, or a combination thereof can be displayed. For example, the display device 222 can be used to communicate a number of settings or menu options for the infusion pump system 500. In this embodiment, the user may press one or more of the buttons 224 to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the fluid cartridge 120, or the like). In some embodiments, the user can adjust the settings or otherwise program the controller device 200 by pressing one or more buttons 224 of the user interface 220. For example, in embodiments of the infusion pump system 500 configured to dispense insulin, the user may press one or more of the buttons 224 to change the dispensation rate of insulin or to request that a bolus of insulin be dispensed immediately or at a scheduled, later time. In some implementations, the display device 222 may also be used to communicate information regarding remaining battery life.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas. The inspection light device 230 can also be used to notify the user to an alert condition of the infusion pump system 500. An activation of the inspection light device 230 can thereby provide a visual notification (as an alternative to, or in addition to, the visual notification provided on the display device 222) to the user that attention to the infusion pump system 500 is warranted.

The controller device 200 of the infusion pump system 500 also includes a NFC circuit 240. The NFC circuit 240 can wirelessly communicate with external NFC tags, such as example NFC tags 246a, 246b, 246c, and 246d. As described previously, such wireless communications using NFC technology can enhance and simplify user interactions with the infusion pump system 500. For instance, using NFC, the need for user activation of buttons 224 for shuffling through menus may be reduced in some circumstances. FIG. 5 depicts an example scenario to illustrate this principle. In this example scenario, the user of infusion pump system 500 has consumed, or will soon consume, about 50 grams of carbohydrates. As such, the user desires to schedule or initiate a corresponding bolus dispensation of insulin to counteract the effects of the intake of 50 grams of carbohydrates. The bolus dispensation of insulin is intended to cause the user's blood glucose level to remain within a target range. To schedule or initiate the desired bolus dispensation, the user first positions the controller device 200 containing the NFC circuit 240 in close proximity with the NFC tag 246c (which is programmed to correspond to 50 grams of carbohydrates). Wireless NFC communications can thereby be established between the NFC circuit 240 and the NFC tag 246c (as signified by wireless communication symbol 247). In some embodiments, the user is provided with a notification that NFC communications have been established. The notification can be visual, audible, tactile, and a combination thereof. In response to the communication from the NFC tag 246c to the controller device 200, the controller device 200 provides a prompt to the user on the display device 222. In this example, the prompt on the display device 222 requests the user to confirm that the user desires to receive a 3.3 Unit dispensation of insulin because of the intake of 50 grams of carbohydrates. To confirm the dispensation of the suggested bolus amount, the user can simply press the button 224 directly below the word "Enter." By this example, it can be appreciated that the incorporation of NFC technology in the infusion pump system 500 can enhance and simplify user interactions with the infusion pump system 500, because to initiate an appropriate bolus dosage of insulin the user simply had to present a NFC tag 246c to the NFC circuit 240 and then press button 224 in response to the prompt on the display device 222.

Optionally, the controller device 200 can further include at least one accelerometer 250. In some embodiments, the accelerometer 250 can be used as a criteria to activate or complete the NFC communications when a characteristic value of a detected movement of the controller device 200 is at or above the threshold level, as previously described above in connection with FIGS. 1 and 4. In such circumstances, the control circuitry housed in the controller device 200 can be configured to determine when the controller housing 210 is "bumped" against one of the NFC tags 246a-246d so as to activate the NFC transmission via the NFC circuit 240.

Figure 6:
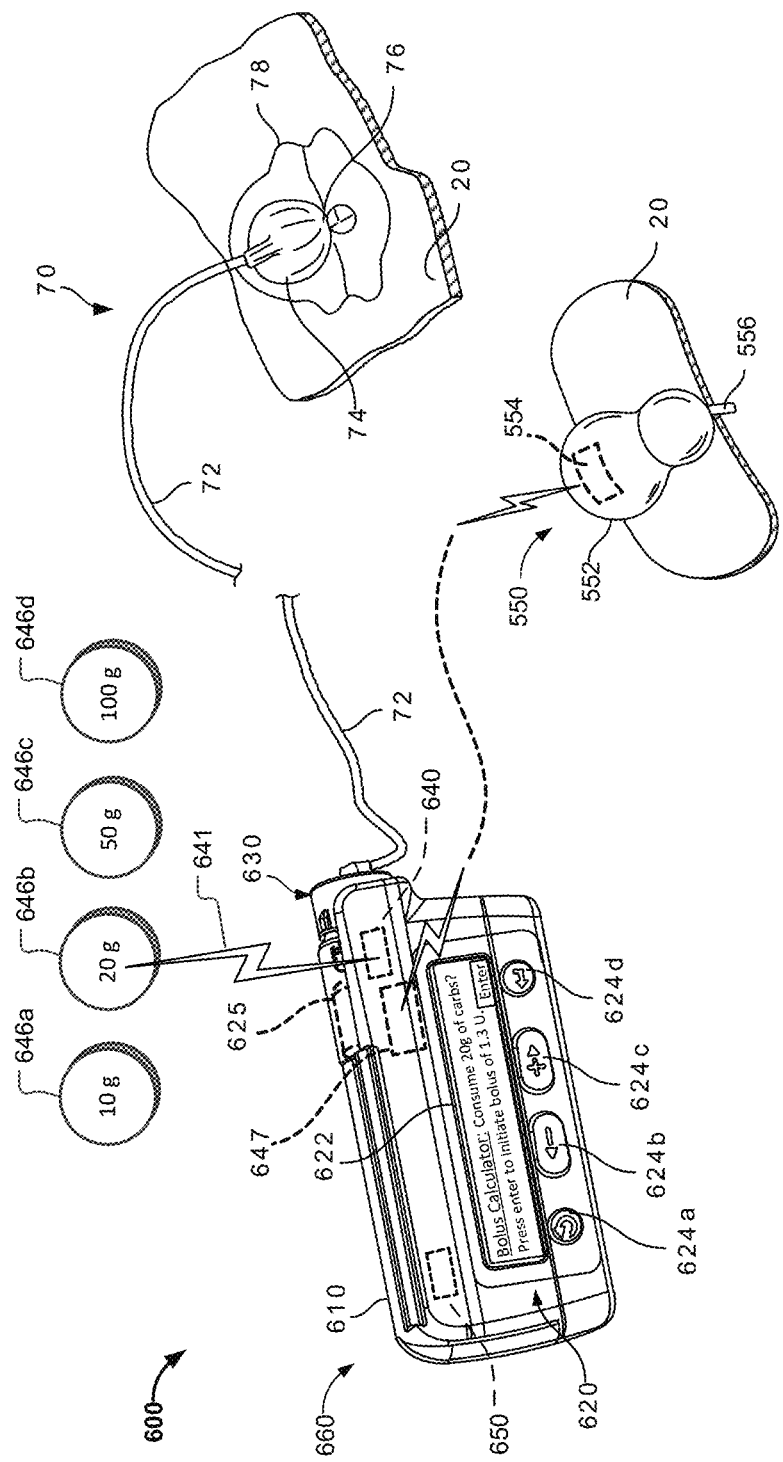
FIG. 6 is a perspective view of another infusion pump system with NFC capabilities in accordance with some embodiments.

Referring now to FIG. 6, some embodiments of an infusion pump system 600 configured to communicate with NFC tags can also be configured to wirelessly communicate with a continuous glucose monitoring device 550. For example, in this embodiment, the infusion pump system 600 can include an infusion pump assembly 660 used to supply insulin or another medication to a user via, for example, an infusion set 70. The glucose monitoring device 550 communicates with the infusion pump assembly 660 for the purpose of supplying data indicative of a user's blood glucose level to a control circuitry included in the infusion pump assembly 660. The infusion pump system 600 can utilize the data indicative of a user's blood glucose level in the calculation of a bolus dosage.

In this embodiment, the infusion pump assembly 660 includes a housing structure 610 that defines a cavity in which a fluid cartridge 625 can be received. The infusion pump assembly 660 also includes a cap device 630 to retain the fluid cartridge 625 in the cavity of the housing structure 610. The infusion pump assembly 660 includes a drive system (e.g., described in more detail in connection with FIG. 5) that advances a plunger in the fluid cartridge 625 so as to dispense fluid therefrom. In some embodiments, the dispensed fluid exits the fluid cartridge 625, passes through a flexible tube 72 of the infusion set 70 to a cannula housing 74. The dispensed fluid can enter through the skin 20 via a cannula 76 attached to the underside of the cannula housing 74.

Still referring to FIG. 6, the glucose monitoring device 550 can include a housing 552, a wireless communication device 554, and a sensor shaft 556. The wireless communication device 554 can be contained within the housing 552 and the sensor shaft 556 can extend outward from the housing 552. In use, the sensor shaft 556 can penetrate the skin 20 of a user to make measurements indicative of characteristics of the user's blood (e.g., the user's blood glucose level or the like). In response to the measurements made by the sensor shaft 556, the glucose monitoring device 550 can employ the wireless communication device 554 to transmit data to the control circuitry of the infusion pump assembly 660.

In some embodiments, the glucose monitoring device 550 may include a circuit that permits sensor signals (e.g., data from the sensor shaft 556) to be communicated to the wireless communication device 554. The wireless communication device 554 can transfer the collected data to the infusion pump assembly 660 (e.g., by wireless communication to a communication device 647 arranged in the pump assembly 660). In some embodiments, the glucose monitoring device 550 can employ other methods of obtaining information indicative of a user's blood characteristics and transferring that information to the infusion pump assembly 660. For example, an alternative monitoring device may employ a micropore system in which a laser porator creates tiny holes in the uppermost layer of a user's skin, through which interstitial glucose is measured using a patch. Alternatively, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some embodiments, the glucose monitoring device 550 can be in communication with the infusion pump assembly 660 via a wired connection. In other embodiments of the infusion pump system 600, test strips (e.g., blood test strips) containing a sample of the user's blood can be inserted into a strip reader portion of the infusion pump assembly 660 to be tested for characteristics of the user's blood. Alternatively, the test strips (e.g., glucose test strips) containing a sample of the user's blood can be inserted into a glucose meter device (not shown in FIG. 6), which then analyzes the characteristics of the user's blood and communicates the information (via a wired or wireless connection) to the pump assembly 660. In still other embodiments, characteristics of the user's blood glucose information can be entered directly into the infusion pump assembly 660 via a user interface 620 on the infusion pump assembly 660.

Still referring to FIG. 6, the infusion pump assembly 660 includes the user interface 620 that permits a user to monitor the operation of the infusion pump assembly 660. In some embodiments, the user interface 620 includes a display 622 and one or more user-selectable buttons (e.g., four buttons 624a, 624b, 624c, and 624d in this embodiment, a different arrangement of buttons in other embodiments, or touch-screen buttons in still other embodiments). The display 622 may include an active area in which numerals, text, symbols, images, or a combination thereof can be displayed. For example, the display 622 may be used to communicate a number of status indicators, alarms, settings, and/or menu options for the infusion pump system 600. In some embodiments, the display 622 can indicate inform the user of the amount of a suggested bolus dosage, the user's blood glucose level, an indication that the user's blood glucose level is rising or falling, an indication that the bolus dosage suggestion includes a correction for the rate of change in the user's blood glucose level, and the like.

In some embodiments, the user may press one or more of the buttons 624a, 624b, 624c, and 624d to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the fluid cartridge 625, or the like). In some embodiments, the user can adjust the settings or otherwise program the infusion pump assembly 660 by pressing one or more buttons 624a, 624b, 624c, and 624d of the user interface 620. For example, in embodiments of the infusion pump system 600 configured to dispense insulin, the user may press one or more of the buttons 624a, 624b, 624c, and 624d to change the dispensation rate of insulin or to request that a bolus of insulin be dispensed immediately or at a scheduled, later time. In another example, the user may use the buttons 624a-624d to manually input information such as the user's current blood glucose level (e.g., as measured by an external blood glucose meter), the current rate of change in the user's blood glucose level, or the like into the infusion pump system 600.

The infusion pump assembly 660 also includes a NFC circuit 640. The NFC circuit 640 can wirelessly communicate with external NFC tags, such as example NFC tags 646a, 646b, 646c, and 646d. As described previously, such wireless communications using NFC technology can enhance and simplify user interactions with the infusion pump system 600. For instance, using NFC, the need for user activation of buttons 624a-d for shuffling through menus may be reduced in some circumstances. FIG. 6 depicts an example scenario to illustrate this operational concept. In this example scenario, the user of infusion pump system 600 has consumed, or will soon consume, about 20 grams of carbohydrates. As such, the user desires to initiate a corresponding bolus dispensation of insulin to counteract the effects of the intake of 20 grams of carbohydrates. The bolus dispensation of insulin is intended to cause the user's blood glucose level to remain within a target range. To initiate the desired bolus dispensation, the user first positions the infusion pump assembly 660 containing the NFC circuit 640 in close proximity with the NFC tag 646b (which is programmed to correspond to 20 grams of carbohydrates). Wireless NFC communications can thereby be established between the NFC circuit 640 and the NFC tag 646b (as signified by wireless communication symbol 641). In some embodiments, the user is provided with a notification that NFC communications have been established. The notification can be visual, audible, tactile, and a combination thereof. In some embodiments, in response to the communication from the NFC tag 646b to the infusion pump assembly 660, the infusion pump assembly 660 provides a prompt to the user on the display 622. In this example, the prompt on the display device 622 requests the user to confirm that the user desires to receive a 1.3-unit dispensation of insulin because of the intake of 20 grams of carbohydrates. To confirm the dispensation of the suggested bolus amount, the user can simply press the button 624d directly below the word "Enter." By this example, it can be appreciated that the incorporation of NFC technology in the infusion pump system 600 can enhance and simplify user interactions with the infusion pump system 600, because to initiate an appropriate bolus dosage of insulin the user simply had to present a NFC tag 646b to the NFC circuit 640 and then press button 624d in response to the prompt on the display 622.

Optionally, the infusion pump assembly 660 can further include at least one accelerometer 650. In some embodiments, the accelerometer 650 can be used to activate or complete the NFC communications when a characteristic value of a detected movement of the infusion pump assembly 660 is at or above the threshold level, as previously described above in connection with FIGS. 1 and 4. In such circumstances, the control circuitry housed in the infusion pump assembly 660 be configured to determine when the housing structure 610 is "bumped" against one of the NFC tags 646a-646d so as to activate the NFC transmission via the NFC circuit 640.

Figure 7:
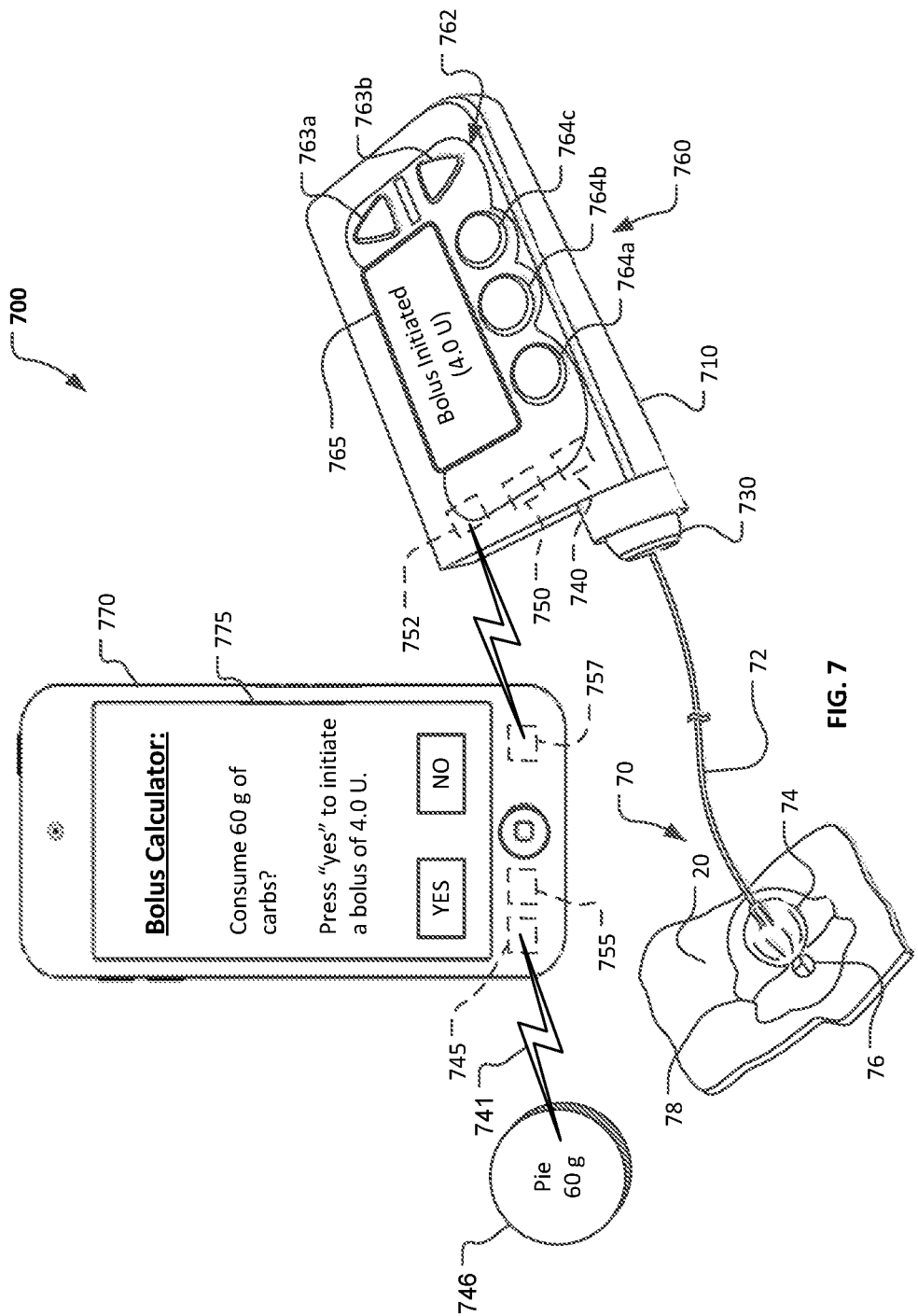
FIG. 7 is a perspective view of another infusion pump system with NFC capabilities in accordance with some embodiments.

Referring now to FIG. 7, some embodiments of an infusion pump system 700 can include an ancillary remote-control device 770 configured to communicate with NFC tags 746 and with an infusion pump assembly 760. In this example embodiment, the remote control device 770 is a smartphone. In other embodiments, the remote-control device 770 can be other types of devices such as a tablet computer, laptop computer, a PDA, a custom remote device manufactured specifically for interfacing with the infusion pump assembly 760, and the like. In this example embodiment, the pump assembly 760 is a single-piece pump unit (similar to the embodiment described above in connection with FIG. 1). In other embodiments of the infusion pump system 700, the infusion pump assembly 760 can be configured as a two-piece pump assembly such as the example depicted in FIG. 5.

In general, the remote-control device 770 includes a control system for controlling the infusion pump assembly 760, including user interface components such as touch-screen user interface 775 for allowing a user to receive and provide instructions relative to the infusion pump assembly 760. The remote-control device 770 also includes a wireless interface 757 for communicating with a wireless interface 752 of the infusion pump assembly 760. The wireless interfaces 752 and 757 for communicating between the infusion pump assembly 760 and the remote-control device 770 can utilize any of a variety of wireless communication technologies, such as BLUETOOTH®, WiFi®, RF, infrared, ultrasonic, electromagnetic induction, NFC, or combinations thereof. The infusion pump assembly 760 can be used to dispense insulin or another medication to a user via, for example, an infusion set 70 as described in regard to other infusion pump system embodiments herein.

In this embodiment, the infusion pump assembly 760 includes a housing structure 710 that defines a cavity in which a fluid cartridge (e.g., an insulin carpule or other medicine cartridge) can be received. The infusion pump assembly 760 also includes a cap device 730 to retain the fluid cartridge in the cavity of the housing structure 710. The infusion pump assembly 760 includes a drive system (e.g., described in more detail in connection with FIG. 5) that advances a plunger in the fluid cartridge so as to dispense fluid therefrom. In some embodiments, the dispensed fluid exits the fluid cartridge, passes through a flexible tube 72 of the infusion set 70 to a cannula housing 74. The dispensed fluid can enter through the skin 20 via a cannula 76 attached to the underside of the cannula housing 74.

In some embodiments, the infusion pump system 700 can be configured to supply scheduled basal dosages of insulin (or another medication) along with user-selected bolus dosages. The basal delivery rate can be selected to maintain a user's blood glucose level in a targeted range during normal activity when the user is not consuming food items. The user-selected bolus deliveries may provide substantially larger amounts of insulin in particular circumstances, such as when the user consumes food items, when the user's blood glucose level increases beyond a safe limit, when the user's blood glucose level rises faster than a threshold rate, or other scenarios in which the blood glucose level requires a significant correction. In some embodiments, the infusion pump system 700 may modify a bolus delivery (e.g., a bolus delivery after the user consumes a meal) in response to certain circumstances. For example, the infusion pump system 700 may decrease or otherwise modify a post-meal bolus delivery based on a rapidly falling blood glucose level, a current blood glucose level that is below a threshold limit, a detection of a high level of physical activity, or the like.

Still referring to FIG. 7, in this embodiment, the infusion pump assembly 760 includes the user interface 762 that permits a user to monitor the operation of the infusion pump assembly 760. In some embodiments, the user interface 762 includes a user interface display 765 and one or more user-selectable buttons (e.g., five buttons 764a, 764b, 764c, 763a, and 763b in this embodiment). The user interface display 765 may include an active area in which numerals, text, symbols, images, or a combination thereof can be displayed. For example, the user interface display 765 may be used to communicate a number of status indicators, alarms, settings, and/or menu options for the infusion pump system 700. In some embodiments, the user interface display 765 can indicate inform the user of the amount of a suggested bolus dosage, the user's blood glucose level, an indication that the user's blood glucose level is rising or falling, an indication that the bolus dosage suggestion includes a correction for the rate of change in the user's blood glucose level, and the like.

In some embodiments, the user may press one or more of the buttons 764a, 764b, 764c, 763a, and 763b to shuffle through a number of menus or program screens that show particular status indicators, settings, and/or data (e.g., review data that shows the medicine dispensing rate, the amount of medicine delivered during the last bolus, the delivery time of the last bolus, the total amount of medicine dispensed in a given time period, the amount of medicine scheduled to be dispensed at a particular time or date, the approximate amount of medicine remaining in the cartridge, or the like). In some embodiments, the user can adjust the settings or otherwise program the infusion pump assembly 760 by pressing one or more buttons 764a, 764b, 764c, 763a, and 763b of the user interface 762. For example, in embodiments of the infusion pump system 700 configured to dispense insulin, the user may press one or more of the buttons 764a, 764*b*, 764*c*, 763*a*, and 763*b* to change the dispensation rate of insulin or to request that a bolus of insulin be dispensed immediately or at a scheduled, later time. In another example, the user may use the buttons 764*a*, 764*b*, 764*c*, 763*a*, and 763*b* to manually input information such as the user's current blood glucose level (e.g., as measured by an external blood glucose meter), the current rate of change in the user's blood glucose level, or the like into the infusion pump system 700.

As an alternative to, or in addition to, using user interface 762 to control the infusion pump assembly 760, the remote-control device 770 can be used to control the infusion pump assembly 760 in this embodiment. Such an arrangement may be convenient, for example, if the user is wearing the infusion pump assembly 760 in a concealed location under clothing. The remote-control device 770 can wirelessly communicate with the pump assembly 760 via the wireless interfaces 757 and 752. The wireless communications between the infusion pump assembly 760 and the remote-control device 770 can utilize any of a variety of wireless communication technologies, such as BLUETOOTH®, WiFi®, RF, infrared, ultrasonic, electromagnetic induction, NFC, and the like, and combinations thereof. Using remote-control device 770, a user can enter and receive information whereby the user can control the infusion pump assembly 760 using the touchscreen user interface 775 of the remote-control device 770 as an alternative to, or in addition to, using the user interface 762 of the infusion pump assembly 760. In some alternative embodiments, the infusion pump assembly 760 may be configured without a user interface display 765 or other user interface components for purposes of reducing manufacturing costs, in which case the touchscreen user interface 775 of the remote-control device 770 would serve as the user interface for the infusion pump system 700.

The remote-control device 770 also includes a NFC circuit 745. The NFC circuit 745 can wirelessly communicate with external NFC tags, such as the example NFC tag 746. As described previously, such wireless communications using NFC technology can enhance and simplify user interactions with the infusion pump system 700. For instance, using NFC, the need for user activation of buttons 764*a*, 764*b*, 764*c*, 763*a*, and 763*b*, or for using user the touchscreen user interface 775, for shuffling through menus may be reduced in some circumstances. FIG. 7 depicts an example scenario to illustrate this principle. In this example scenario, the user of infusion pump system 700 has consumed, or will soon consume, about 60 grams of carbohydrates by eating a piece of pie. As such, the user desires to initiate a corresponding bolus dispensation of insulin to counteract the effects of the intake of 60 grams of carbohydrates. The bolus dispensation of insulin is intended to cause the user's blood glucose level to remain within a target range. To initiate the desired bolus dispensation, the user first positions the remote-control device 770 containing the NFC circuit 745 in close proximity with the NFC tag 746 (which is programmed to correspond to 60 grams of carbohydrates). Wireless NFC communications can thereby be established between the NFC circuit 745 and the NFC tag 746 (as signified by wireless communication symbol 741). In some embodiments, the user is provided with a notification that NFC communications have been established. The notification can be visual, audible, tactile, and a combination thereof.

In response to the communication from the NFC tag 746 to the remote-control device 770, the remote-control device 770 can provide a prompt to the user on the touchscreen user interface 775. In this example, the prompt on the touchscreen user interface 775 requests the user to confirm whether the user desires to receive a 4.0 Unit dispensation of insulin because of the intake of 60 grams of carbohydrates. To confirm the dispensation of the suggested bolus amount, the user can simply touch the portion of the touchscreen user interface 775 that is labeled "YES." Or, the user can decline the dispensation of the suggested bolus amount by touching the portion of the touchscreen user interface 775 that is labeled "NO." By this example, it can be appreciated that the incorporation of NFC technology in the infusion pump system 700 can enhance and simplify user interactions with the infusion pump system 700, because to initiate an appropriate bolus dosage of insulin the user simply had to present a NFC tag 746 to the NFC circuit 745 of the remote-control device 770 and then touch the portion of the touchscreen user interface 775 that is labeled "YES."

Optionally, the remote-control device 770 can further include at least one accelerometer 755. In some embodiments, the accelerometer 755 can be used to activate the NFC communications when a characteristic value of a detected movement of the remote-control device 770 is at or above the threshold level, as previously described above in connection with FIGS. 1 and 4. In such circumstances, the control circuitry housed in remote-control device 770 be configured to determine when the remote-control device 770 is "bumped" against one of the NFC tags 746 so as to activate the NFC transmission via the NFC circuit 745.

While the infusion pump system 700 includes the remote-control device 770 that includes NFC circuit 745, in some embodiments the infusion pump assembly 760 can also include a NFC circuit 740. Therefore, the user can alternatively present NFC tags to the infusion pump assembly 760 to input information to the infusion pump assembly 760. Similarly, the pump assembly 760 can optionally include at least one accelerometer 750 that can be used to activate the NFC communications when a characteristic value of a detected movement of the infusion pump assembly 760 is at or above the threshold level, as previously described above in connection with FIGS. 1 and 4. In such circumstances, the control circuitry housed in infusion pump assembly 760 can be configured to determine when the infusion pump assembly 760 is "bumped" against one of the NFC tags 746 so as to activate the NFC transmission via the NFC circuit 740.

A number of embodiments of the invention have been described. Nevertheless, it will be understood that various modifications may be made without departing from the spirit and scope of the invention. Accordingly, other embodiments are within the scope of the following claims.

What is claimed is:

1. An insulin delivery system, comprising:
   an insulin delivery device;
   a near field communication (NFC) device to store and transmit data regarding insulin therapy; and
   a mobile device comprising:
      a display;
      at least one processor; and
      at least one non-transitory computer-readable storage medium storing instructions thereon that, when executed by the at least one processor, cause the mobile device to:
         responsive to the mobile device being tapped or bumped adjacent to or against the NFC device, receive the data regarding insulin therapy from the NFC device;
         responsive to receiving the data regarding insulin therapy from the NFC device, determine a suggested bolus dosage of insulin based at least partially on the data regarding insulin therapy; and cause a prompt for a user to confirm or deny the suggested bolus dosage of insulin be displayed on the display.

2. The insulin delivery system of claim 1, wherein the instructions, when executed by the at least one processor, cause the mobile device to:

responsive to a user interaction confirming the suggested bolus dosage of insulin, transmit insulin delivery instructions reflecting the suggested bolus dosage of insulin to the insulin delivery device.

3. The insulin delivery system of claim 1, wherein responsive to the insulin delivery device being tapped or bumped adjacent to or against the NFC device, receive insulin delivery instructions from the NFC device; and deliver insulin to a the user according to the received insulin delivery instructions.

4. The insulin delivery system of claim 1, wherein the instructions, when executed by the at least one processor, cause the mobile device to:

responsive to a user interaction confirming the suggested bolus dosage of insulin, writing new data regarding insulin therapy to the NFC device.

5. The insulin delivery system of claim 1, wherein the NFC device comprises an NFC tag.

6. The insulin delivery system of claim 5, wherein the NFC tag stores data regarding a meal item.

7. The insulin delivery system of claim 1, wherein the mobile device comprises an accelerometer.

8. The insulin delivery system of claim 7, wherein the instructions, when executed by the at least one processor, cause the mobile device to:

detect acceleration of the mobile device; and determine whether a movement value of the detected acceleration of the mobile device meets or exceeds a threshold movement value.

9. The insulin delivery system of claim 8, wherein the instructions, when executed by the at least one processor, cause the mobile device to:

responsive to determining that the movement value of the detected acceleration of the mobile device meets or exceeds the threshold movement value and detecting a proximity of the NFC device, initiating communication with the NFC device.

10. The insulin delivery system of claim 9, wherein the insulin delivery device comprises:

a portable housing defining a space to receive the insulin; and a drive system for dispensing the insulin from the portable housing.

* * * * *

UNITED STATES PATENT AND TRADEMARK OFFICE
CERTIFICATE OF CORRECTION

| | | |
|---|---|---|
| PATENT NO. | : 12,064,591 B2 | Page 1 of 1 |
| APPLICATION NO. | : 17/445819 | |
| DATED | : August 20, 2024 | |
| INVENTOR(S) | : Mark C. Estes | |

It is certified that error appears in the above-identified patent and that said Letters Patent is hereby corrected as shown below:

In the Specification

| | | |
|---|---|---|
| Column 8, | Line 15, | change "particular because" to --particularly because-- |
| Column 9, | Line 1, | change "in the housing" to --in the pump housing-- |
| Column 14, | Line 63, | change "of tasks receives" to --of tasks or receives-- |
| Column 19, | Line 3, | change "to the tag 432)" to --to the NFC tag 432)-- |
| Column 20, | Line 40, | change "the controller" to --the pump controller-- |
| Column 20, | Line 41, | change "of the pump" to --of the separate pump-- |
| Column 20, | Line 59, | change "of the controller" to --of the pump controller-- |
| Column 20, | Line 60, | change "the pump device" to --the separate pump device-- |
| Column 20, | Line 62, | change "the controller" to --the pump controller-- |
| Column 21, | Line 2, | change "the infusion" to --the portable infusion-- |
| Column 25, | Line 32, | change "in the pump" to --in the infusion pump-- |
| Column 25, | Line 63, | change "to the pump" to --to the infusion pump-- |
| Column 26, | Line 51, | change "buttons 624*a-d* for" to --buttons 624*a-624*d for-- |
| Column 27, | Line 8, | change "on the display device 622 requests" to --on the display 622 requests-- |
| Column 27, | Line 37, | change "the remote control" to --the remote-control-- |
| Column 27, | Line 43, | change "the pump assembly" to --the infusion pump assembly-- |
| Column 30, | Line 35, | change "the pump assembly" to --the infusion pump assembly-- |

In the Claims

| | | | |
|---|---|---|---|
| Claim 3, | Column 31, | Line 17, | change "deliver insulin to a user" to --deliver insulin to the user-- |

Signed and Sealed this
Twenty-ninth Day of April, 2025

Coke Morgan Stewart
*Acting Director of the United States Patent and Trademark Office*